(12) United States Patent
Raemakers-Franken et al.

(10) Patent No.: US 8,673,599 B2
(45) Date of Patent: Mar. 18, 2014

(54) PREPARATION OF 6-AMINOCAPROIC ACID FROM 5-FORMYLVALERIC ACID

(75) Inventors: Petronella Catharina Raemakers-Franken, Budel (NL); Martin Schurmann, Jülich (DE); Axel Christoph Trefzer, Leidschendam (NL); Stefaan Marie Andre De Wildeman, Maasmechelen (BE)

(73) Assignee: DSM IP Assets B.V., Heerlen (NL)

( * ) Notice: Subject to any disclaimer, the term of this patent is extended or adjusted under 35 U.S.C. 154(b) by 375 days.

(21) Appl. No.: 12/921,733

(22) PCT Filed: Mar. 11, 2009

(86) PCT No.: PCT/NL2009/050117
§ 371 (c)(1),
(2), (4) Date: Dec. 21, 2010

(87) PCT Pub. No.: WO2009/113855
PCT Pub. Date: Sep. 17, 2009

(65) Prior Publication Data
US 2011/0171699 A1 Jul. 14, 2011

(30) Foreign Application Priority Data
Mar. 11, 2008 (EP) .................................... 08152584

(51) Int. Cl.
*C12P 13/00* (2006.01)
*C12N 1/21* (2006.01)
*C12N 1/15* (2006.01)
*C07C 227/06* (2006.01)
*C07D 223/10* (2006.01)

(52) U.S. Cl.
USPC ................... 435/128; 435/254.3; 435/254.5; 435/254.21; 435/254.23; 435/243; 536/23.2

(58) Field of Classification Search
None
See application file for complete search history.

(56) References Cited

FOREIGN PATENT DOCUMENTS

WO 2005/068643 7/2005
WO WO/2005/068643 A * 7/2006

OTHER PUBLICATIONS

International Search Report for PCT/NL2009/050117, mailed Oct. 26, 2009.
Reddy et al., "Expression, Purification, and Crystallization of Meso-Diaminopimelate Dehydrogenase from *Corynebacterium glutamicum*", Proteins: Structure, Function and Genetics, vol. 25, No. 4, Jan. 1, 1996, pp. 514-516, XP001063203.
Ohshima et al., "Thermostable Amino Acid Dehydrogenases: Applications and Gene Cloning", Trends in Biotechnology, Elsevier Publications, Cambridge, GB, vol. 7, No. 8, Aug. 1, 1989, pp. 210-214, XP000037533.

* cited by examiner

*Primary Examiner* — Kagnew H Gebreyesus
(74) *Attorney, Agent, or Firm* — Nixon & Vanderhye P.C.

(57) ABSTRACT

The invention relates to a method for preparing 6-aminocaproic acid (hereinafter also referred to as '6-ACA') using a biocatalyst. The invention further relates to a method for preparing e-caprolactam (hereafter referred to as 'caprolactam') by cyclising such 6-ACA. The invention further relates to a host cell, a micro-organism, or a polynucleotide which may be used in the preparation of 6-ACA or caprolactam.

3 Claims, No Drawings

SEQUENCE LISTING

<160> NUMBER OF SEQ ID NOS: 83

<210> SEQ ID NO 1
<211> LENGTH: 1362
<212> TYPE: DNA
<213> ORGANISM: Vibrio fluvialis
<220> FEATURE:
<221> NAME/KEY: CDS
<222> LOCATION: (1)..(1362)

<400> SEQUENCE: 1

```
atg aac aaa ccg caa agc tgg gaa gcc cgg gcc gag acc tat tcg ctc      48
Met Asn Lys Pro Gln Ser Trp Glu Ala Arg Ala Glu Thr Tyr Ser Leu
1               5                   10                  15 tat ggt ttc acc gac atg cct tcg ctg cat cag cgc ggc acg gtc gtc      96
Tyr Gly Phe Thr Asp Met Pro Ser Leu His Gln Arg Gly Thr Val Val
            20                  25                  30 gtg acc cat ggc gag gga ccc tat atc gtc gat gtg aat ggc cgg cgt     144
Val Thr His Gly Glu Gly Pro Tyr Ile Val Asp Val Asn Gly Arg Arg
        35                  40                  45 tat ctg gac gcc aac tcg ggc ctg tgg aac atg gtc gcg ggc ttt gac     192
Tyr Leu Asp Ala Asn Ser Gly Leu Trp Asn Met Val Ala Gly Phe Asp
    50                  55                  60 cac aag ggg ctg atc gac gcc gcc aag gcc caa tac gag cgt ttt ccc     240
His Lys Gly Leu Ile Asp Ala Ala Lys Ala Gln Tyr Glu Arg Phe Pro
65                  70                  75                  80 ggt tat cac gcc ttt ttc ggc cgc atg tcc gat cag acg gta atg ctg     288
Gly Tyr His Ala Phe Phe Gly Arg Met Ser Asp Gln Thr Val Met Leu
                85                  90                  95 tcg gaa aag ctg gtc gag gtg tcg ccc ttt gat tcg ggc cgg gtg ttc     336
Ser Glu Lys Leu Val Glu Val Ser Pro Phe Asp Ser Gly Arg Val Phe
            100                 105                 110 tat aca aac tcg ggg tcc gag gcg aat gac acc atg gtc aag atg cta     384
Tyr Thr Asn Ser Gly Ser Glu Ala Asn Asp Thr Met Val Lys Met Leu
        115                 120                 125 tgg ttc ctg cat gca gcc gag ggc aaa ccg caa aag cgc aag atc ctg     432
Trp Phe Leu His Ala Ala Glu Gly Lys Pro Gln Lys Arg Lys Ile Leu
    130                 135                 140 acc cgc tgg aac gcc tat cac ggc gtg acc gcc gtt tcg gcc agc atg     480
Thr Arg Trp Asn Ala Tyr His Gly Val Thr Ala Val Ser Ala Ser Met
145                 150                 155                 160 acc ggc aag ccc tat aat tcg gtc ttt ggc ctg ccg ctg ccg ggc ttt     528
Thr Gly Lys Pro Tyr Asn Ser Val Phe Gly Leu Pro Leu Pro Gly Phe
                165                 170                 175 gtg cat ctg acc tgc ccg cat tac tgg cgc tat ggc gaa gag ggc gaa     576
Val His Leu Thr Cys Pro His Tyr Trp Arg Tyr Gly Glu Glu Gly Glu
```

```
                       180                 185                 190
acc gaa gag cag ttc gtc gcc cgc ctc gcc cgc gag ctg gag gaa acg     624
Thr Glu Glu Gln Phe Val Ala Arg Leu Ala Arg Glu Leu Glu Glu Thr
                   195                 200                 205 atc cag cgc gag ggc gcc gac acc atc gcc ggt ttc ttt gcc gaa ccg     672
Ile Gln Arg Glu Gly Ala Asp Thr Ile Ala Gly Phe Phe Ala Glu Pro
            210                 215                 220 gtg atg ggc gcg ggc ggc gtg att ccc ccg gcc aag ggc tat ttc cag     720
Val Met Gly Ala Gly Gly Val Ile Pro Pro Ala Lys Gly Tyr Phe Gln
225                 230                 235                 240 gcg atc ctg cca atc ctg cgc aaa tat gac atc ccg gtc atc tcg gac     768
Ala Ile Leu Pro Ile Leu Arg Lys Tyr Asp Ile Pro Val Ile Ser Asp
                245                 250                 255 gag gtg atc tgc ggt ttc gga cgc acc ggt aac acc tgg ggc tgc gtg     816
Glu Val Ile Cys Gly Phe Gly Arg Thr Gly Asn Thr Trp Gly Cys Val
            260                 265                 270 acc tat gac ttt aca ccc gat gca atc atc tcg tcc aag aat ctt aca     864
Thr Tyr Asp Phe Thr Pro Asp Ala Ile Ile Ser Ser Lys Asn Leu Thr
        275                 280                 285 gcg ggc ttt ttc ccc atg ggg gcg gtg atc ctt ggc ccg gaa ctt tcc     912
Ala Gly Phe Phe Pro Met Gly Ala Val Ile Leu Gly Pro Glu Leu Ser
    290                 295                 300 aaa cgg ctg gaa acc gca atc gag gcg atc gag gaa ttc ccc cat ggc     960
Lys Arg Leu Glu Thr Ala Ile Glu Ala Ile Glu Glu Phe Pro His Gly
305                 310                 315                 320 ttt acc gcc tcg ggc cat ccg gtc ggc tgt gct att gcg ctg aaa gca    1008
Phe Thr Ala Ser Gly His Pro Val Gly Cys Ala Ile Ala Leu Lys Ala
                325                 330                 335 atc gac gtg gtg atg aat gaa ggg ctg gct gag aac gtc cgc cgc ctt    1056
Ile Asp Val Val Met Asn Glu Gly Leu Ala Glu Asn Val Arg Arg Leu
            340                 345                 350 gcc ccc cgt ttc gag gaa agg ctg aaa cat atc gcc gag cgc ccg aac    1104
Ala Pro Arg Phe Glu Glu Arg Leu Lys His Ile Ala Glu Arg Pro Asn
        355                 360                 365 atc ggt gaa tat cgc ggc atc ggc ttc atg tgg gcg ctg gag gct gtc    1152
Ile Gly Glu Tyr Arg Gly Ile Gly Phe Met Trp Ala Leu Glu Ala Val
    370                 375                 380 aag gac aag gca agc aag acg ccg ttc gac ggc aac ctg tcg gtc agc    1200
Lys Asp Lys Ala Ser Lys Thr Pro Phe Asp Gly Asn Leu Ser Val Ser
385                 390                 395                 400 gag cgt atc gcc aat acc tgc acc gat ctg ggg ctg att tgc cgg ccg    1248
Glu Arg Ile Ala Asn Thr Cys Thr Asp Leu Gly Leu Ile Cys Arg Pro
                405                 410                 415 ctt ggt cag tcc gtc gtc ctt tgt ccg ccc ttt atc ctg acc gag gcg    1296
Leu Gly Gln Ser Val Val Leu Cys Pro Pro Phe Ile Leu Thr Glu Ala
            420                 425                 430 cag atg gat gag atg ttc gat aaa ctc gaa aaa gcc ctt gat aag gtc    1344
Gln Met Asp Glu Met Phe Asp Lys Leu Glu Lys Ala Leu Asp Lys Val
        435                 440                 445 ttt gcc gag gtt gcc tga                                            1362
Phe Ala Glu Val Ala
    450

<210> SEQ ID NO 2
<211> LENGTH: 453
<212> TYPE: PRT
<213> ORGANISM: Vibrio fluvialis

<400> SEQUENCE: 2

Met Asn Lys Pro Gln Ser Trp Glu Ala Arg Ala Glu Thr Tyr Ser Leu
1               5                   10                  15
```

-continued

Tyr Gly Phe Thr Asp Met Pro Ser Leu His Gln Arg Gly Thr Val Val
            20                  25                  30

Val Thr His Gly Glu Gly Pro Tyr Ile Val Asp Val Asn Gly Arg Arg
            35                  40                  45

Tyr Leu Asp Ala Asn Ser Gly Leu Trp Asn Met Val Ala Gly Phe Asp
            50                  55                  60

His Lys Gly Leu Ile Asp Ala Ala Lys Ala Gln Tyr Glu Arg Phe Pro
 65                  70                  75                  80

Gly Tyr His Ala Phe Phe Gly Arg Met Ser Asp Gln Thr Val Met Leu
                    85                  90                  95

Ser Glu Lys Leu Val Glu Val Ser Pro Phe Asp Ser Gly Arg Val Phe
                   100                 105                 110

Tyr Thr Asn Ser Gly Ser Glu Ala Asn Asp Thr Met Val Lys Met Leu
                   115                 120                 125

Trp Phe Leu His Ala Ala Glu Gly Lys Pro Gln Lys Arg Lys Ile Leu
                   130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                   165                 170                 175

Val His Leu Thr Cys Pro His Tyr Trp Arg Tyr Gly Glu Glu Gly Glu
                   180                 185                 190

Thr Glu Glu Gln Phe Val Ala Arg Leu Ala Arg Glu Leu Glu Glu Thr
                   195                 200                 205

Ile Gln Arg Glu Gly Ala Asp Thr Ile Ala Gly Phe Phe Ala Glu Pro
                   210                 215                 220

Val Met Gly Ala Gly Gly Val Ile Pro Ala Lys Gly Tyr Phe Gln
225                 230                 235                 240

Ala Ile Leu Pro Ile Leu Arg Lys Tyr Asp Ile Pro Val Ile Ser Asp
                   245                 250                 255

Glu Val Ile Cys Gly Phe Gly Arg Thr Gly Asn Thr Trp Gly Cys Val
                   260                 265                 270

Thr Tyr Asp Phe Thr Pro Asp Ala Ile Ile Ser Ser Lys Asn Leu Thr
                   275                 280                 285

Ala Gly Phe Phe Pro Met Gly Ala Val Ile Leu Gly Pro Glu Leu Ser
                   290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
                   325                 330                 335

Ile Asp Val Val Met Asn Glu Gly Leu Ala Glu Asn Val Arg Arg Leu
                   340                 345                 350

Ala Pro Arg Phe Glu Glu Arg Leu Lys His Ile Ala Glu Arg Pro Asn
                   355                 360                 365

Ile Gly Glu Tyr Arg Gly Ile Gly Phe Met Trp Ala Leu Glu Ala Val
                   370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
                   405                 410                 415

Leu Gly Gln Ser Val Val Leu Cys Pro Pro Phe Ile Leu Thr Glu Ala
                   420                 425                 430

Gln Met Asp Glu Met Phe Asp Lys Leu Glu Lys Ala Leu Asp Lys Val

Phe Ala Glu Val Ala
    450

<210> SEQ ID NO 3
<211> LENGTH: 1362
<212> TYPE: DNA
<213> ORGANISM: Artificial
<220> FEATURE:
<223> OTHER INFORMATION: Vibrio fluvialis JS17 omega-aminotransferase
      codon optimised gene

<400> SEQUENCE: 3

```
atgaataaac cacagtcttg ggaagctcgt gctgaaacct atagcctgta cggctttacc      60
gatatgccgt ctctgcacca gcgtggtact gtagtggtaa cgcacggtga gggcccgtac     120
atcgtggacg ttaatggccg ccgttacctg gatgcaaaca gcggcctgtg gaacatggtt     180
gcgggcttcg accacaaagg cctgatcgat gccgcaaaag cgcagtacga acgcttcccg     240
ggttatcacg cgttctttgg ccgtatgagc gaccagactg tgatgctgag cgaaaaactg     300
gttgaagtgt ccccgttcga tagcggtcgt gtcttttaca ctaactctgg cagcgaggct     360
aacgatacca tggttaagat gctgtggttc ctgcacgcag cggaaggcaa acctcagaaa     420
cgtaaaattc tgacccgttg gaacgcttat acggtgtgat ctgctgtttc cgcatctatg     480
accggtaaac cgtataacag cgtgttcggt ctgccgctgc ctggcttcgt gcatctgacc     540
tgcccgcact actggcgtta tggtgaggaa ggcgaaactg aggaacagtt cgtggcgcgt     600
ctggctcgtg aactggaaga aaccattcaa cgcgaaggtg cagatactat cgcgggcttc     660
tttgcggagc ctgttatggg tgccggcggt gtgattccgc cggcgaaggg ctatttccag     720
gcaatcctgc cgatcctgcg caagtacgac attccggtta tttctgacga agtgatctgc     780
ggcttcggcc gcaccggtaa cacctggggc tgcgtgacgt atgacttcac tccggacgca     840
atcattagct ctaaaaacct gactgcgggt ttcttcccta tgggcgccgt aatcctgggc     900
ccagaactgt ctaagcgcct ggaaaccgcc atcgaggcaa tcgaagagtt cccgcacggt     960
ttcactgcta gcggccatcc ggtaggctgc gcaatcgcgc tgaaggcgat cgatgttgtc    1020
atgaacgagg gcctggcgga aaacgtgcgc cgcctggcgc cgcgttttga gaacgtctg    1080
aaacacattg ctgagcgccc gaacattggc gaatatcgcg gcatcggttt catgtgggcc    1140
ctggaagcag ttaaagataa agctagcaag accccgttcg acggcaacct gtccgtgagc    1200
gaacgtatcg ctaatacctg tacgacctgg gtctgatct gccgtccgct gggtcagtcc    1260
gtagttctgt gcccaccatt tatcctgacc gaagcgcaga tggatgaaat gttcgataaa    1320
ctggagaaag ctctggataa agtgttcgct gaagtcgcgt aa                       1362
```

<210> SEQ ID NO 4
<211> LENGTH: 1350
<212> TYPE: DNA
<213> ORGANISM: Bacillus weihenstephanensis
<220> FEATURE:
<221> NAME/KEY: CDS
<222> LOCATION: (1)..(1350)

<400> SEQUENCE: 4

```
gtg caa gcg acg gag caa aca caa agt ttg aaa aaa aca gat gaa aag       48
Val Gln Ala Thr Glu Gln Thr Gln Ser Leu Lys Lys Thr Asp Glu Lys
1               5                   10                  15 tac ctt tgg cat gcg atg aga gga gca gcc cct agt cca acg aat tta       96
Tyr Leu Trp His Ala Met Arg Gly Ala Ala Pro Ser Pro Thr Asn Leu
            20                  25                  30
```

-continued

| | |
|---|---|
| att atc aca aaa gca gaa ggg gca tgg gtg acg gat att gat gga aac<br>Ile Ile Thr Lys Ala Glu Gly Ala Trp Val Thr Asp Ile Asp Gly Asn<br>         35                         40                     45 | 144 |
| cgt tat tta gac ggt atg tcc ggt ctt tgg tgc gtg aat gtt ggg tat<br>Arg Tyr Leu Asp Gly Met Ser Gly Leu Trp Cys Val Asn Val Gly Tyr<br>  50                         55                        60 | 192 |
| ggt cga aaa gaa ctt gca aga gcg gcg ttt gaa cag ctt gaa gaa atg<br>Gly Arg Lys Glu Leu Ala Arg Ala Ala Phe Glu Gln Leu Glu Glu Met<br>65                      70                        75                    80 | 240 |
| ccg tat ttc cct ctg act caa agt cat gtt cct gct att aaa tta gca<br>Pro Tyr Phe Pro Leu Thr Gln Ser His Val Pro Ala Ile Lys Leu Ala<br>                      85                        90                    95 | 288 |
| gaa aaa ttg aat gaa tgg ctt gat gat gaa tac gtc att ttc ttt tct<br>Glu Lys Leu Asn Glu Trp Leu Asp Asp Glu Tyr Val Ile Phe Phe Ser<br>              100                      105                  110 | 336 |
| aac agt gga tcg gaa gcg aat gaa aca gca ttt aaa att gct cgt caa<br>Asn Ser Gly Ser Glu Ala Asn Glu Thr Ala Phe Lys Ile Ala Arg Gln<br>              115                      120                  125 | 384 |
| tat cat caa caa aaa ggt gat cat gga cgc tat aag ttt att tcc cgc<br>Tyr His Gln Gln Lys Gly Asp His Gly Arg Tyr Lys Phe Ile Ser Arg<br>130                      135                      140 | 432 |
| tac cgc gct tat cac ggt aac tca atg gga gct ctt gca gca aca ggt<br>Tyr Arg Ala Tyr His Gly Asn Ser Met Gly Ala Leu Ala Ala Thr Gly<br>145                      150                      155                  160 | 480 |
| caa gca cag cga aag tat aaa tat gaa cca ctc ggg caa gga ttc ctg<br>Gln Ala Gln Arg Lys Tyr Lys Tyr Glu Pro Leu Gly Gln Gly Phe Leu<br>                      165                      170                  175 | 528 |
| cat gta gca ccg cct gat acg tat cga aat cca gag gat gtt cat aca<br>His Val Ala Pro Pro Asp Thr Tyr Arg Asn Pro Glu Asp Val His Thr<br>                  180                      185                  190 | 576 |
| ctg gca agt gct gag gaa atc gat cgt gtc atg aca tgg gag tta agc<br>Leu Ala Ser Ala Glu Glu Ile Asp Arg Val Met Thr Trp Glu Leu Ser<br>              195                      200                  205 | 624 |
| caa aca gta gcc ggt gtg att atg gag cca atc att act ggg ggc gga<br>Gln Thr Val Ala Gly Val Ile Met Glu Pro Ile Ile Thr Gly Gly Gly<br>          210                      215                      220 | 672 |
| att tta atg cct cct gat gga tat atg gga aaa gta aaa gaa att tgc<br>Ile Leu Met Pro Pro Asp Gly Tyr Met Gly Lys Val Lys Glu Ile Cys<br>225                      230                      235                  240 | 720 |
| gag aag cac ggt gcg ttg ctc att tgt gat gaa gtt ata tgt gga ttt<br>Glu Lys His Gly Ala Leu Leu Ile Cys Asp Glu Val Ile Cys Gly Phe<br>                  245                      250                  255 | 768 |
| ggc cgg aca ggg aag cca ttt gga ttt atg aat tat ggc gtc aaa cca<br>Gly Arg Thr Gly Lys Pro Phe Gly Phe Met Asn Tyr Gly Val Lys Pro<br>              260                      265                  270 | 816 |
| gat atc att aca atg gca aaa ggt att aca agt gcg tat ctt cct ttg<br>Asp Ile Ile Thr Met Ala Lys Gly Ile Thr Ser Ala Tyr Leu Pro Leu<br>            275                      280                  285 | 864 |
| tca gca aca gca gtt aga cga gag gtt tat gag gca ttc gta ggt agt<br>Ser Ala Thr Ala Val Arg Arg Glu Val Tyr Glu Ala Phe Val Gly Ser<br>          290                      295                  300 | 912 |
| gat gat tat gat cgc ttc cgc cat gta aat acg ttc gga ggg aat cct<br>Asp Asp Tyr Asp Arg Phe Arg His Val Asn Thr Phe Gly Gly Asn Pro<br>305                      310                      315                  320 | 960 |
| gct gct tgc gct tta gct ttg aag aat tta gaa att atg gag aat gag<br>Ala Ala Cys Ala Leu Ala Leu Lys Asn Leu Glu Ile Met Glu Asn Glu<br>                  325                      330                  335 | 1008 |
| aaa ctc att gaa cgt tcc aaa gaa ttg ggt gaa cga ctg tta tat gag<br>Lys Leu Ile Glu Arg Ser Lys Glu Leu Gly Glu Arg Leu Leu Tyr Glu<br>              340                      345                  350 | 1056 |

```
cta gag gat gta aaa gag cat cca aac gta ggg gat gtt cgc gga aag      1104
Leu Glu Asp Val Lys Glu His Pro Asn Val Gly Asp Val Arg Gly Lys
            355                 360                 365 ggc ctt ctt tta ggc att gaa cta gtg gaa gat aag caa aca aaa gaa      1152
Gly Leu Leu Leu Gly Ile Glu Leu Val Glu Asp Lys Gln Thr Lys Glu
370                 375                 380 ccg gct tcc att gaa aag atg aac aaa gtc atc aat gct tgt aaa gaa      1200
Pro Ala Ser Ile Glu Lys Met Asn Lys Val Ile Asn Ala Cys Lys Glu
385                 390                 395                 400 aaa ggt cta att att ggt aaa aat ggt gac act gtc gca ggt tac aat      1248
Lys Gly Leu Ile Ile Gly Lys Asn Gly Asp Thr Val Ala Gly Tyr Asn
                405                 410                 415 aat att ttg cag ctt gca cct cca tta agc atc aca gag gaa gac ttt      1296
Asn Ile Leu Gln Leu Ala Pro Pro Leu Ser Ile Thr Glu Glu Asp Phe
            420                 425                 430 act ttt atc gtt aaa aca atg aaa gaa tgt tta tcc cgc att aac ggg      1344
Thr Phe Ile Val Lys Thr Met Lys Glu Cys Leu Ser Arg Ile Asn Gly
        435                 440                 445 cag taa                                                              1350
Gln
```

<210> SEQ ID NO 5
<211> LENGTH: 449
<212> TYPE: PRT
<213> ORGANISM: Bacillus weihenstephanensis

<400> SEQUENCE: 5

```
Val Gln Ala Thr Glu Gln Thr Gln Ser Leu Lys Lys Thr Asp Glu Lys
1               5                   10                  15

Tyr Leu Trp His Ala Met Arg Gly Ala Ala Pro Ser Pro Thr Asn Leu
            20                  25                  30

Ile Ile Thr Lys Ala Glu Gly Ala Trp Val Thr Asp Ile Asp Gly Asn
        35                  40                  45

Arg Tyr Leu Asp Gly Met Ser Gly Leu Trp Cys Val Asn Val Gly Tyr
    50                  55                  60

Gly Arg Lys Glu Leu Ala Arg Ala Ala Phe Glu Gln Leu Glu Glu Met
65                  70                  75                  80

Pro Tyr Phe Pro Leu Thr Gln Ser His Val Pro Ala Ile Lys Leu Ala
                85                  90                  95

Glu Lys Leu Asn Glu Trp Leu Asp Asp Glu Tyr Val Ile Phe Phe Ser
            100                 105                 110

Asn Ser Gly Ser Glu Ala Asn Glu Thr Ala Phe Lys Ile Ala Arg Gln
        115                 120                 125

Tyr His Gln Gln Lys Gly Asp His Gly Arg Tyr Lys Phe Ile Ser Arg
    130                 135                 140

Tyr Arg Ala Tyr His Gly Asn Ser Met Gly Ala Leu Ala Ala Thr Gly
145                 150                 155                 160

Gln Ala Gln Arg Lys Tyr Lys Tyr Glu Pro Leu Gly Gln Gly Phe Leu
                165                 170                 175

His Val Ala Pro Pro Asp Thr Tyr Arg Asn Pro Glu Asp Val His Thr
            180                 185                 190

Leu Ala Ser Ala Glu Glu Ile Asp Arg Val Met Thr Trp Glu Leu Ser
        195                 200                 205

Gln Thr Val Ala Gly Val Ile Met Glu Pro Ile Ile Thr Gly Gly Gly
    210                 215                 220

Ile Leu Met Pro Pro Asp Gly Tyr Met Gly Lys Val Lys Glu Ile Cys
225                 230                 235                 240
```

```
Glu Lys His Gly Ala Leu Leu Ile Cys Asp Glu Val Ile Cys Gly Phe
                245                 250                 255
Gly Arg Thr Gly Lys Pro Phe Gly Phe Met Asn Tyr Gly Val Lys Pro
            260                 265                 270
Asp Ile Ile Thr Met Ala Lys Gly Ile Thr Ser Ala Tyr Leu Pro Leu
        275                 280                 285
Ser Ala Thr Ala Val Arg Arg Glu Val Tyr Glu Ala Phe Val Gly Ser
    290                 295                 300
Asp Asp Tyr Asp Arg Phe Arg His Val Asn Thr Phe Gly Gly Asn Pro
305                 310                 315                 320
Ala Ala Cys Ala Leu Ala Leu Lys Asn Leu Glu Ile Met Glu Asn Glu
                325                 330                 335
Lys Leu Ile Glu Arg Ser Lys Glu Leu Gly Glu Arg Leu Leu Tyr Glu
            340                 345                 350
Leu Glu Asp Val Lys Glu His Pro Asn Val Gly Asp Val Arg Gly Lys
        355                 360                 365
Gly Leu Leu Leu Gly Ile Glu Leu Val Glu Asp Lys Gln Thr Lys Glu
    370                 375                 380
Pro Ala Ser Ile Glu Lys Met Asn Lys Val Ile Asn Ala Cys Lys Glu
385                 390                 395                 400
Lys Gly Leu Ile Ile Gly Lys Asn Gly Asp Thr Val Ala Gly Tyr Asn
                405                 410                 415
Asn Ile Leu Gln Leu Ala Pro Pro Leu Ser Ile Thr Glu Glu Asp Phe
            420                 425                 430
Thr Phe Ile Val Lys Thr Met Lys Glu Cys Leu Ser Arg Ile Asn Gly
        435                 440                 445
Gln

<210> SEQ ID NO 6
<211> LENGTH: 1350
<212> TYPE: DNA
<213> ORGANISM: Artificial
<220> FEATURE:
<223> OTHER INFORMATION: B. weihenstephanensis KBAB4 aminotransferase
      codon-optimised gene

<400> SEQUENCE: 6
atgcaggcta ccgaacaaac ccaatctctg aaaaagactg acgaaaaata tctgtggcac    60
gcgatgcgcg gtcagctcc gtctccgacc aacctgatta ttaccaaagc tgaaggcgcg   120
tgggtgaccg acattgacgg taaccgttat ctggatggca tgagcggcct gtggtgtgtt   180
aatgtcggtt atggccgtaa ggagctggcg cgcgcggcat tgaacaact ggaagaaatg   240 ccgtacttcc gctgactca aagccatgtg ccggctatca aactggcgga aaaactgaac   300
gaatggctgg acgacgaata cgtgattttc ttctctaatt ctggctccga agcaaacgaa   360
accgcattca aaatcgcccg tcaatatcac cagcagaaag gtgaccacgg ccgctataaa   420
ttcatcagcc gttatcgtgc ataccatggt aattctatgg gtgcgctggc tgctaccggt   480
caggctcagc gcaaatacaa gtacgaaccg ctgggtcagg ttttctgca cgttgcacca   540 ccggatacct accgtaaccc ggaagacgtc cacaccctgg cttctgccga gaaatcgat   600 cgtgttatga cctgggagct gtcccagact gttgcgggtg ttatcatgga acctattatt   660
accggtggtg gcattctgat gccgccggac ggttatatgg gtaaagtcaa ggaaatctgc   720
gaaaaacacg gcgcgctgct gatctgcgat gaagttatct gtggcttcgg tcgcaccggc   780
aaaccatttg gcttcatgaa ttatggcgta aaacctgaca ttattaccat ggctaaaggc   840
```

-continued

```
attacttccg cttatctgcc gctgagcgcg accgcagttc gccgcgaagt ttatgaagcg     900
tttgttggtt ctgatgatta cgaccgtttc cgtcatgtaa acacgtttgg cggtaaccca     960
gcggcatgtg cgctggcgct gaaaaacctg gaaatcatgg aaaacgaaaa gctgatcgaa    1020
cgtagcaaag aactgggtga acgtctgctg tacgaactgg aagatgtcaa agaacacccg    1080
aacgtgggcg atgttcgcgg taaaggcctg ctgctgggta ttgaactggt tgaagacaaa    1140
cagaccaagg aaccggcttc cattgaaaag atgaacaaag tgattaacgc gtgcaaagag    1200
aaaggcctga tcattggtaa gaacggtgat accgtggcag gttataacaa cattctgcag    1260
ctggcgccgc tctgagcat cactgaagaa gatttcacct tcatcgtcaa aactatgaag    1320
gagtgcctga gccgcatcaa tggtcagtaa                                    1350
```

<210> SEQ ID NO 7
<211> LENGTH: 1371
<212> TYPE: DNA
<213> ORGANISM: Pseudomonas aeruginosa
<220> FEATURE:
<221> NAME/KEY: CDS
<222> LOCATION: (1)..(1371)

<400> SEQUENCE: 7

```
atg aac agc caa atc acc aac gcc aag acc cgt gag tgg cag gcg ttg      48
Met Asn Ser Gln Ile Thr Asn Ala Lys Thr Arg Glu Trp Gln Ala Leu
1               5                   10                  15 agc cgc gac cac cat ctg ccg ccg ttc acc gac tac aag cag ttg aac      96
Ser Arg Asp His His Leu Pro Pro Phe Thr Asp Tyr Lys Gln Leu Asn
                20                  25                  30 gag aag ggc gcg cgg atc atc acc aag gcc gaa ggc gtc tat atc tgg    144
Glu Lys Gly Ala Arg Ile Ile Thr Lys Ala Glu Gly Val Tyr Ile Trp
            35                  40                  45 gac agc gag ggc aac aag atc ctc gat gcg atg gcc ggc ctc tgg tgc    192
Asp Ser Glu Gly Asn Lys Ile Leu Asp Ala Met Ala Gly Leu Trp Cys
        50                  55                  60 gtc aac gtc ggc tac ggc cgc gag gag ctg gtc cag gcc gcc acc cgg    240
Val Asn Val Gly Tyr Gly Arg Glu Glu Leu Val Gln Ala Ala Thr Arg
65                  70                  75                  80 cag atg cgc gag ttg ccg ttc tac aac ctg ttc ttc cag acc gcc cac    288
Gln Met Arg Glu Leu Pro Phe Tyr Asn Leu Phe Phe Gln Thr Ala His
                85                  90                  95 ccg ccg gtg gtc gag ctg gcc aag gcg atc gcc gac gtc gct ccg gaa    336
Pro Pro Val Val Glu Leu Ala Lys Ala Ile Ala Asp Val Ala Pro Glu
                100                 105                 110 ggc atg aac cac gtg ttc ttc acc ggc tcc ggc tcc gag gcc aac gac    384
Gly Met Asn His Val Phe Phe Thr Gly Ser Gly Ser Glu Ala Asn Asp
            115                 120                 125 acc gtg ctg cgt atg gtc cgc cac tat tgg gcg acc aag ggc cag ccg    432
Thr Val Leu Arg Met Val Arg His Tyr Trp Ala Thr Lys Gly Gln Pro
        130                 135                 140 cag aag aaa gtg gtg atc ggc cgc tgg aac ggc tac cac ggc tcc acc    480
Gln Lys Lys Val Val Ile Gly Arg Trp Asn Gly Tyr His Gly Ser Thr
145                 150                 155                 160 gtc gcc ggc gtc agc ctg ggc ggc atg aag gcg ttg cat gag cag ggt    528
Val Ala Gly Val Ser Leu Gly Gly Met Lys Ala Leu His Glu Gln Gly
                165                 170                 175 gat ttc ccc atc ccg ggc atc gtc cac atc gcc cag ccc tac tgg tac    576
Asp Phe Pro Ile Pro Gly Ile Val His Ile Ala Gln Pro Tyr Trp Tyr
                180                 185                 190 ggc gag ggc ggc gac atg tcg ccg gac gag ttc ggc gtc tgg gcc gcc    624
Gly Glu Gly Gly Asp Met Ser Pro Asp Glu Phe Gly Val Trp Ala Ala
```

|  |  |  |  |  |  |  |  |  |  |  |  |  |  |  |  | |
|---|---|---|---|---|---|---|---|---|---|---|---|---|---|---|---|---|
|  |  | 195 |  |  |  | 200 |  |  |  |  | 205 |  |  |  |  | |
| gag | cag | ttg | gag | aag | aag | att | ctc | gaa | gtg | ggc | gag | gaa | aac | gtc | gcc | 672 |
| Glu | Gln | Leu | Glu | Lys | Lys | Ile | Leu | Glu | Val | Gly | Glu | Glu | Asn | Val | Ala | |
|  | 210 |  |  |  |  | 215 |  |  |  |  | 220 |  |  |  |  | |
| gcc | ttc | atc | gcc | gag | ccg | atc | cag | ggc | gcc | ggc | ggc | gtg | atc | gtc | ccg | 720 |
| Ala | Phe | Ile | Ala | Glu | Pro | Ile | Gln | Gly | Ala | Gly | Gly | Val | Ile | Val | Pro | |
| 225 |  |  |  |  | 230 |  |  |  |  | 235 |  |  |  |  | 240 | |
| ccg | gac | acc | tac | tgg | ccg | aag | atc | cgc | gag | atc | ctc | gcc | aag | tac | gac | 768 |
| Pro | Asp | Thr | Tyr | Trp | Pro | Lys | Ile | Arg | Glu | Ile | Leu | Ala | Lys | Tyr | Asp | |
|  |  |  |  | 245 |  |  |  |  | 250 |  |  |  |  | 255 |  | |
| atc | ctg | ttc | atc | gcc | gac | gaa | gtg | atc | tgc | ggc | ttc | ggc | cgt | acc | ggc | 816 |
| Ile | Leu | Phe | Ile | Ala | Asp | Glu | Val | Ile | Cys | Gly | Phe | Gly | Arg | Thr | Gly | |
|  |  |  | 260 |  |  |  |  | 265 |  |  |  |  | 270 |  |  | |
| gag | tgg | ttc | ggc | agc | cag | tac | tac | ggc | aac | gcc | ccg | gac | ctg | atg | ccg | 864 |
| Glu | Trp | Phe | Gly | Ser | Gln | Tyr | Tyr | Gly | Asn | Ala | Pro | Asp | Leu | Met | Pro | |
|  |  | 275 |  |  |  |  | 280 |  |  |  |  | 285 |  |  |  | |
| atc | gcc | aag | ggc | ctc | acc | tcc | ggc | tac | atc | ccc | atg | ggc | ggg | gtg | gtg | 912 |
| Ile | Ala | Lys | Gly | Leu | Thr | Ser | Gly | Tyr | Ile | Pro | Met | Gly | Gly | Val | Val | |
|  | 290 |  |  |  |  | 295 |  |  |  |  | 300 |  |  |  |  | |
| gtg | cgc | gac | gag | atc | gtc | gaa | gtg | ctc | aac | cag | ggc | ggc | gag | ttc | tac | 960 |
| Val | Arg | Asp | Glu | Ile | Val | Glu | Val | Leu | Asn | Gln | Gly | Gly | Glu | Phe | Tyr | |
| 305 |  |  |  |  | 310 |  |  |  |  | 315 |  |  |  |  | 320 | |
| cac | ggc | ttc | acc | tat | tcc | ggt | cac | ccg | gtg | gcg | gcc | gcc | gtg | gcc | ctg | 1008 |
| His | Gly | Phe | Thr | Tyr | Ser | Gly | His | Pro | Val | Ala | Ala | Ala | Val | Ala | Leu | |
|  |  |  |  | 325 |  |  |  |  | 330 |  |  |  |  | 335 |  | |
| gag | aac | atc | cgc | atc | ctg | cgc | gaa | gag | aag | atc | atc | gag | aag | gtg | aag | 1056 |
| Glu | Asn | Ile | Arg | Ile | Leu | Arg | Glu | Glu | Lys | Ile | Ile | Glu | Lys | Val | Lys | |
|  |  |  | 340 |  |  |  |  | 345 |  |  |  |  | 350 |  |  | |
| gcg | gaa | acg | gca | ccg | tat | ttg | cag | aaa | cgc | tgg | cag | gag | ctg | gcc | gac | 1104 |
| Ala | Glu | Thr | Ala | Pro | Tyr | Leu | Gln | Lys | Arg | Trp | Gln | Glu | Leu | Ala | Asp | |
|  |  | 355 |  |  |  |  | 360 |  |  |  |  | 365 |  |  |  | |
| cac | ccg | ttg | gtg | ggc | gaa | gcg | cgc | ggg | gtc | ggc | atg | gtc | gcc | gcc | ctg | 1152 |
| His | Pro | Leu | Val | Gly | Glu | Ala | Arg | Gly | Val | Gly | Met | Val | Ala | Ala | Leu | |
|  | 370 |  |  |  |  | 375 |  |  |  |  | 380 |  |  |  |  | |
| gag | ctg | gtc | aag | aac | aag | aag | acc | cgc | gag | cgt | ttc | acc | gac | aag | ggc | 1200 |
| Glu | Leu | Val | Lys | Asn | Lys | Lys | Thr | Arg | Glu | Arg | Phe | Thr | Asp | Lys | Gly | |
| 385 |  |  |  |  | 390 |  |  |  |  | 395 |  |  |  |  | 400 | |
| gtc | ggg | atg | ctg | tgc | cgg | gaa | cat | tgt | ttc | cgc | aac | ggt | ttg | atc | atg | 1248 |
| Val | Gly | Met | Leu | Cys | Arg | Glu | His | Cys | Phe | Arg | Asn | Gly | Leu | Ile | Met | |
|  |  |  |  | 405 |  |  |  |  | 410 |  |  |  |  | 415 |  | |
| cgc | gcg | gtg | ggc | gac | act | atg | att | atc | tcg | ccg | ccg | ctg | gtg | atc | gat | 1296 |
| Arg | Ala | Val | Gly | Asp | Thr | Met | Ile | Ile | Ser | Pro | Pro | Leu | Val | Ile | Asp | |
|  |  |  | 420 |  |  |  |  | 425 |  |  |  |  | 430 |  |  | |
| ccg | tcg | cag | atc | gat | gag | ttg | atc | acc | ctg | gcg | cgc | aag | tgc | ctc | gat | 1344 |
| Pro | Ser | Gln | Ile | Asp | Glu | Leu | Ile | Thr | Leu | Ala | Arg | Lys | Cys | Leu | Asp | |
|  |  | 435 |  |  |  |  | 440 |  |  |  |  | 445 |  |  |  | |
| cag | acc | gcc | gcc | gcc | gtc | ctg | gct | tga |  |  |  |  |  |  |  | 1371 |
| Gln | Thr | Ala | Ala | Ala | Val | Leu | Ala |  |  |  |  |  |  |  |  | |
|  | 450 |  |  |  |  | 455 |  |  |  |  |  |  |  |  |  | |

<210> SEQ ID NO 8
<211> LENGTH: 456
<212> TYPE: PRT
<213> ORGANISM: Pseudomonas aeruginosa

<400> SEQUENCE: 8

| Met | Asn | Ser | Gln | Ile | Thr | Asn | Ala | Lys | Thr | Arg | Glu | Trp | Gln | Ala | Leu |
|---|---|---|---|---|---|---|---|---|---|---|---|---|---|---|---|
| 1 |  |  |  | 5 |  |  |  |  | 10 |  |  |  |  | 15 |  |

| Ser | Arg | Asp | His | His | Leu | Pro | Pro | Phe | Thr | Asp | Tyr | Lys | Gln | Leu | Asn |
|---|---|---|---|---|---|---|---|---|---|---|---|---|---|---|---|
|  |  | 20 |  |  |  |  | 25 |  |  |  |  | 30 |  |  |  |

-continued

Glu Lys Gly Ala Arg Ile Ile Thr Lys Ala Glu Gly Val Tyr Ile Trp
         35                  40                  45

Asp Ser Glu Gly Asn Lys Ile Leu Asp Ala Met Ala Gly Leu Trp Cys
 50                  55                  60

Val Asn Val Gly Tyr Gly Arg Glu Glu Leu Val Gln Ala Ala Thr Arg
 65                  70                  75                  80

Gln Met Arg Glu Leu Pro Phe Tyr Asn Leu Phe Gln Thr Ala His
                 85                  90                  95

Pro Pro Val Val Glu Leu Ala Lys Ala Ile Ala Asp Val Ala Pro Glu
                100                 105                 110

Gly Met Asn His Val Phe Phe Thr Gly Ser Gly Ser Glu Ala Asn Asp
                115                 120                 125

Thr Val Leu Arg Met Val Arg His Tyr Trp Ala Thr Lys Gly Gln Pro
130                 135                 140

Gln Lys Lys Val Val Ile Gly Arg Trp Asn Gly Tyr His Gly Ser Thr
145                 150                 155                 160

Val Ala Gly Val Ser Leu Gly Gly Met Lys Ala Leu His Glu Gln Gly
                165                 170                 175

Asp Phe Pro Ile Pro Gly Ile Val His Ile Ala Gln Pro Tyr Trp Tyr
                180                 185                 190

Gly Glu Gly Gly Asp Met Ser Pro Asp Glu Phe Gly Val Trp Ala Ala
                195                 200                 205

Glu Gln Leu Glu Lys Lys Ile Leu Glu Val Gly Glu Asn Val Ala
210                 215                 220

Ala Phe Ile Ala Glu Pro Ile Gln Gly Ala Gly Gly Val Ile Val Pro
225                 230                 235                 240

Pro Asp Thr Tyr Trp Pro Lys Ile Arg Glu Ile Leu Ala Lys Tyr Asp
                245                 250                 255

Ile Leu Phe Ile Ala Asp Glu Val Ile Cys Gly Phe Gly Arg Thr Gly
                260                 265                 270

Glu Trp Phe Gly Ser Gln Tyr Tyr Gly Asn Ala Pro Asp Leu Met Pro
                275                 280                 285

Ile Ala Lys Gly Leu Thr Ser Gly Tyr Ile Pro Met Gly Gly Val Val
290                 295                 300

Val Arg Asp Glu Ile Val Glu Val Leu Asn Gln Gly Gly Glu Phe Tyr
305                 310                 315                 320

His Gly Phe Thr Tyr Ser Gly His Pro Val Ala Ala Val Ala Leu
                325                 330                 335

Glu Asn Ile Arg Ile Leu Arg Glu Glu Lys Ile Ile Glu Lys Val Lys
                340                 345                 350

Ala Glu Thr Ala Pro Tyr Leu Gln Lys Arg Trp Gln Glu Leu Ala Asp
                355                 360                 365

His Pro Leu Val Gly Glu Ala Arg Gly Val Gly Met Val Ala Ala Leu
                370                 375                 380

Glu Leu Val Lys Asn Lys Lys Thr Arg Glu Arg Phe Thr Asp Lys Gly
385                 390                 395                 400

Val Gly Met Leu Cys Arg Glu His Cys Phe Arg Asn Gly Leu Ile Met
                405                 410                 415

Arg Ala Val Gly Asp Thr Met Ile Ile Ser Pro Pro Leu Val Ile Asp
                420                 425                 430

Pro Ser Gln Ile Asp Glu Leu Ile Thr Leu Ala Arg Lys Cys Leu Asp
                435                 440                 445

Gln Thr Ala Ala Ala Val Leu Ala
450                 455

```
<210> SEQ ID NO 9
<211> LENGTH: 70
<212> TYPE: DNA
<213> ORGANISM: Artificial
<220> FEATURE:
<223> OTHER INFORMATION: primer

<400> SEQUENCE: 9
ggggacaagt ttgtacaaaa aagcaggcta ggaggaatta accatgaaca gccaaatcac    60
caacgccaag                                                           70

<210> SEQ ID NO 10
<211> LENGTH: 49
<212> TYPE: DNA
<213> ORGANISM: Artificial
<220> FEATURE:
<223> OTHER INFORMATION: primer

<400> SEQUENCE: 10
ggggaccact ttgtacaaga aagctgggtt caagccagga cggcggcgg              49

<210> SEQ ID NO 11
<211> LENGTH: 1365
<212> TYPE: DNA
<213> ORGANISM: Pseudomonas syringae
<220> FEATURE:
<221> NAME/KEY: CDS
<222> LOCATION: (1)..(1365)

<400> SEQUENCE: 11
```

| | | | | | | | | | | | | | | | | |
|---|---|---|---|---|---|---|---|---|---|---|---|---|---|---|---|---|
| atg | agt | gcc | aac | aac | ccg | caa | acc | ctc | gaa | tgg | cag | gcc | ctg | agc | agc | 48 |
| Met | Ser | Ala | Asn | Asn | Pro | Gln | Thr | Leu | Glu | Trp | Gln | Ala | Leu | Ser | Ser | |
| 1 | | | | 5 | | | | | 10 | | | | | 15 | | |
| gag | cat | cac | ctg | gca | ccg | ttc | agc | gac | tac | aaa | caa | ctg | aaa | gag | aaa | 96 |
| Glu | His | His | Leu | Ala | Pro | Phe | Ser | Asp | Tyr | Lys | Gln | Leu | Lys | Glu | Lys | |
| | | | 20 | | | | | 25 | | | | | 30 | | | |
| ggc | ccg | cgc | atc | atc | acc | cgt | gcc | gag | ggc | gtt | tat | ctg | tgg | gac | agc | 144 |
| Gly | Pro | Arg | Ile | Ile | Thr | Arg | Ala | Glu | Gly | Val | Tyr | Leu | Trp | Asp | Ser | |
| | | 35 | | | | | 40 | | | | | 45 | | | | |
| gag | ggc | aac | aag | atc | ctc | gat | ggc | atg | tcc | ggc | ctg | tgg | tgc | gtg | gcc | 192 |
| Glu | Gly | Asn | Lys | Ile | Leu | Asp | Gly | Met | Ser | Gly | Leu | Trp | Cys | Val | Ala | |
| | 50 | | | | | 55 | | | | | 60 | | | | | |
| atc | ggt | tat | ggc | cgc | gaa | gaa | ctg | gcc | gac | gca | gcc | agc | aaa | cag | atg | 240 |
| Ile | Gly | Tyr | Gly | Arg | Glu | Glu | Leu | Ala | Asp | Ala | Ala | Ser | Lys | Gln | Met | |
| 65 | | | | | 70 | | | | | 75 | | | | | 80 | |
| cgc | gag | ctg | ccg | tac | tac | aac | ctg | ttc | ttc | cag | acc | gcc | cac | ccg | ccg | 288 |
| Arg | Glu | Leu | Pro | Tyr | Tyr | Asn | Leu | Phe | Phe | Gln | Thr | Ala | His | Pro | Pro | |
| | | | | 85 | | | | | 90 | | | | | 95 | | |
| gtg | ctg | gaa | ctg | gcc | aag | gcc | atc | tcc | gac | atc | gct | ccc | gag | ggc | atg | 336 |
| Val | Leu | Glu | Leu | Ala | Lys | Ala | Ile | Ser | Asp | Ile | Ala | Pro | Glu | Gly | Met | |
| | | | | 100 | | | | | 105 | | | | | 110 | | |
| aac | cat | gtg | ttc | ttc | acc | ggt | tca | ggc | tct | gaa | ggc | aat | gac | acg | atg | 384 |
| Asn | His | Val | Phe | Phe | Thr | Gly | Ser | Gly | Ser | Glu | Gly | Asn | Asp | Thr | Met | |
| | | | 115 | | | | | 120 | | | | | 125 | | | |
| ctg | cgc | atg | gtt | cgt | cat | tac | tgg | gcg | ctg | aaa | ggc | cag | ccg | aac | aag | 432 |
| Leu | Arg | Met | Val | Arg | His | Tyr | Trp | Ala | Leu | Lys | Gly | Gln | Pro | Asn | Lys | |
| | | 130 | | | | | 135 | | | | | 140 | | | | |
| aaa | acc | atc | atc | agc | cgc | gtc | aat | ggc | tac | cac | ggc | tcc | acc | gtc | gcc | 480 |
| Lys | Thr | Ile | Ile | Ser | Arg | Val | Asn | Gly | Tyr | His | Gly | Ser | Thr | Val | Ala | |
| 145 | | | | | 150 | | | | | 155 | | | | | 160 | |
| ggt | gcc | agc | ctg | ggt | ggc | atg | acc | tac | atg | cac | gaa | cag | ggc | gac | ctg | 528 |
| Gly | Ala | Ser | Leu | Gly | Gly | Met | Thr | Tyr | Met | His | Glu | Gln | Gly | Asp | Leu | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 165 |     |     |     |     | 170 |     |     |     |     | 175 |     |      |
| ccg | atc | ccg | ggg | gtg | gtg | cac | att | cca | cag | cct | tac | tgg | ttc | ggc | gaa | 576  |
| Pro | Ile | Pro | Gly | Val | Val | His | Ile | Pro | Gln | Pro | Tyr | Trp | Phe | Gly | Glu |      |
|     |     |     | 180 |     |     |     |     | 185 |     |     |     |     | 190 |     |     |      |
| ggc | ggc | gac | atg | acg | ccg | gac | gag | ttc | ggc | atc | tgg | gcg | gcc | gag | caa | 624  |
| Gly | Gly | Asp | Met | Thr | Pro | Asp | Glu | Phe | Gly | Ile | Trp | Ala | Ala | Glu | Gln |      |
|     |     |     | 195 |     |     |     |     | 200 |     |     |     |     | 205 |     |     |      |
| ctg | gaa | aag | aaa | att | ctc | gag | ctg | ggc | gtc | gag | aac | gtc | ggt | gcg | ttc | 672  |
| Leu | Glu | Lys | Lys | Ile | Leu | Glu | Leu | Gly | Val | Glu | Asn | Val | Gly | Ala | Phe |      |
|     | 210 |     |     |     |     | 215 |     |     |     |     | 220 |     |     |     |     |      |
| att | gcc | gag | cca | atc | cag | ggc | gcg | ggc | ggt | gtg | att | gtc | ccg | cct | gat | 720  |
| Ile | Ala | Glu | Pro | Ile | Gln | Gly | Ala | Gly | Gly | Val | Ile | Val | Pro | Pro | Asp |      |
| 225 |     |     |     |     | 230 |     |     |     |     | 235 |     |     |     |     | 240 |      |
| tcc | tac | tgg | ccg | aag | atc | aag | gaa | atc | ctt | tcc | cgc | tac | gac | atc | ctg | 768  |
| Ser | Tyr | Trp | Pro | Lys | Ile | Lys | Glu | Ile | Leu | Ser | Arg | Tyr | Asp | Ile | Leu |      |
|     |     |     |     | 245 |     |     |     |     | 250 |     |     |     |     | 255 |     |      |
| ttc | gcc | gcc | gat | gag | gtg | att | tgt | ggc | ttc | ggg | cgt | acc | agt | gag | tgg | 816  |
| Phe | Ala | Ala | Asp | Glu | Val | Ile | Cys | Gly | Phe | Gly | Arg | Thr | Ser | Glu | Trp |      |
|     |     |     | 260 |     |     |     |     | 265 |     |     |     |     | 270 |     |     |      |
| ttc | ggt | agc | gat | ttc | tat | ggc | ctc | agg | ccg | gac | atg | atg | acc | atc | gcc | 864  |
| Phe | Gly | Ser | Asp | Phe | Tyr | Gly | Leu | Arg | Pro | Asp | Met | Met | Thr | Ile | Ala |      |
|     |     | 275 |     |     |     |     | 280 |     |     |     |     | 285 |     |     |     |      |
| aaa | ggc | ctg | acc | tcc | ggt | tac | gta | ccg | atg | ggc | ggc | ctg | atc | gtg | cgc | 912  |
| Lys | Gly | Leu | Thr | Ser | Gly | Tyr | Val | Pro | Met | Gly | Gly | Leu | Ile | Val | Arg |      |
|     | 290 |     |     |     |     | 295 |     |     |     |     | 300 |     |     |     |     |      |
| gat | gaa | atc | gtt | gcg | gtg | ctc | aat | gag | ggt | ggc | gat | ttc | aat | cac | ggc | 960  |
| Asp | Glu | Ile | Val | Ala | Val | Leu | Asn | Glu | Gly | Gly | Asp | Phe | Asn | His | Gly |      |
| 305 |     |     |     |     | 310 |     |     |     |     | 315 |     |     |     |     | 320 |      |
| ttt | acc | tac | tcc | ggg | cac | ccg | gtg | gcg | gcc | gcg | gtt | gcg | ctg | gag | aac | 1008 |
| Phe | Thr | Tyr | Ser | Gly | His | Pro | Val | Ala | Ala | Ala | Val | Ala | Leu | Glu | Asn |      |
|     |     |     |     | 325 |     |     |     |     | 330 |     |     |     |     | 335 |     |      |
| atc | cgt | atc | ctg | cgc | gaa | gaa | aag | atc | gtc | gaa | cgg | gtc | agg | tcg | gaa | 1056 |
| Ile | Arg | Ile | Leu | Arg | Glu | Glu | Lys | Ile | Val | Glu | Arg | Val | Arg | Ser | Glu |      |
|     |     |     | 340 |     |     |     |     | 345 |     |     |     |     | 350 |     |     |      |
| acg | gca | ccg | tat | ttg | caa | aag | cgt | ttg | cgt | gag | ttg | agc | gat | cat | ccg | 1104 |
| Thr | Ala | Pro | Tyr | Leu | Gln | Lys | Arg | Leu | Arg | Glu | Leu | Ser | Asp | His | Pro |      |
|     |     | 355 |     |     |     |     | 360 |     |     |     |     | 365 |     |     |     |      |
| ctg | gtg | ggc | gaa | gtc | cgg | ggt | gtc | ggg | ctg | ctc | ggg | gcc | att | gag | ctg | 1152 |
| Leu | Val | Gly | Glu | Val | Arg | Gly | Val | Gly | Leu | Leu | Gly | Ala | Ile | Glu | Leu |      |
|     | 370 |     |     |     |     | 375 |     |     |     |     | 380 |     |     |     |     |      |
| gtg | aag | gac | aag | acc | acc | cgc | gag | cgc | tat | acc | gac | aag | ggc | gcg | gga | 1200 |
| Val | Lys | Asp | Lys | Thr | Thr | Arg | Glu | Arg | Tyr | Thr | Asp | Lys | Gly | Ala | Gly |      |
| 385 |     |     |     |     | 390 |     |     |     |     | 395 |     |     |     |     | 400 |      |
| atg | atc | tgt | cga | acc | ttc | tgc | ttc | gac | aat | ggc | ctg | atc | atg | cgg | gct | 1248 |
| Met | Ile | Cys | Arg | Thr | Phe | Cys | Phe | Asp | Asn | Gly | Leu | Ile | Met | Arg | Ala |      |
|     |     |     |     | 405 |     |     |     |     | 410 |     |     |     |     | 415 |     |      |
| gtg | ggc | gat | acc | atg | atc | att | gcg | ccg | cca | ctg | gtg | atc | agt | ttt | gcg | 1296 |
| Val | Gly | Asp | Thr | Met | Ile | Ile | Ala | Pro | Pro | Leu | Val | Ile | Ser | Phe | Ala |      |
|     |     |     | 420 |     |     |     |     | 425 |     |     |     |     | 430 |     |     |      |
| caa | atc | gat | gag | ctg | gta | gag | aag | gcg | cgc | acg | tgt | ctg | gat | ctg | acg | 1344 |
| Gln | Ile | Asp | Glu | Leu | Val | Glu | Lys | Ala | Arg | Thr | Cys | Leu | Asp | Leu | Thr |      |
|     |     | 435 |     |     |     |     | 440 |     |     |     |     | 445 |     |     |     |      |
| ctg | gcg | gtg | ttg | cag | ggc | tga |     |     |     |     |     |     |     |     |     | 1365 |
| Leu | Ala | Val | Leu | Gln | Gly |     |     |     |     |     |     |     |     |     |     |      |
|     | 450 |     |     |     |     |     |     |     |     |     |     |     |     |     |     |      |

```
<210> SEQ ID NO 12
<211> LENGTH: 454
<212> TYPE: PRT
<213> ORGANISM: Pseudomonas syringae
```

<400> SEQUENCE: 12

```
Met Ser Ala Asn Asn Pro Gln Thr Leu Glu Trp Gln Ala Leu Ser Ser
1               5                  10                  15

Glu His His Leu Ala Pro Phe Ser Asp Tyr Lys Gln Leu Lys Glu Lys
            20                  25                  30

Gly Pro Arg Ile Ile Thr Arg Ala Glu Gly Val Tyr Leu Trp Asp Ser
        35                  40                  45

Glu Gly Asn Lys Ile Leu Asp Gly Met Ser Gly Leu Trp Cys Val Ala
    50                  55                  60

Ile Gly Tyr Gly Arg Glu Glu Leu Ala Asp Ala Ala Ser Lys Gln Met
65                  70                  75                  80

Arg Glu Leu Pro Tyr Tyr Asn Leu Phe Phe Gln Thr Ala His Pro Pro
                85                  90                  95

Val Leu Glu Leu Ala Lys Ala Ile Ser Asp Ile Ala Pro Glu Gly Met
            100                 105                 110

Asn His Val Phe Phe Thr Gly Ser Gly Ser Glu Gly Asn Asp Thr Met
        115                 120                 125

Leu Arg Met Val Arg His Tyr Trp Ala Leu Lys Gly Gln Pro Asn Lys
    130                 135                 140

Lys Thr Ile Ile Ser Arg Val Asn Gly Tyr His Gly Ser Thr Val Ala
145                 150                 155                 160

Gly Ala Ser Leu Gly Gly Met Thr Tyr Met His Glu Gln Gly Asp Leu
                165                 170                 175

Pro Ile Pro Gly Val Val His Ile Pro Gln Pro Tyr Trp Phe Gly Glu
            180                 185                 190

Gly Gly Asp Met Thr Pro Asp Glu Phe Gly Ile Trp Ala Ala Glu Gln
        195                 200                 205

Leu Glu Lys Lys Ile Leu Glu Leu Gly Val Glu Asn Val Gly Ala Phe
    210                 215                 220

Ile Ala Glu Pro Ile Gln Gly Ala Gly Gly Val Ile Val Pro Pro Asp
225                 230                 235                 240

Ser Tyr Trp Pro Lys Ile Lys Glu Ile Leu Ser Arg Tyr Asp Ile Leu
                245                 250                 255

Phe Ala Ala Asp Glu Val Ile Cys Gly Phe Gly Arg Thr Ser Glu Trp
            260                 265                 270

Phe Gly Ser Asp Phe Tyr Gly Leu Arg Pro Asp Met Met Thr Ile Ala
        275                 280                 285

Lys Gly Leu Thr Ser Gly Tyr Val Pro Met Gly Gly Leu Ile Val Arg
    290                 295                 300

Asp Glu Ile Val Ala Val Leu Asn Glu Gly Gly Asp Phe Asn His Gly
305                 310                 315                 320

Phe Thr Tyr Ser Gly His Pro Val Ala Ala Val Ala Leu Glu Asn
                325                 330                 335

Ile Arg Ile Leu Arg Glu Glu Lys Ile Val Glu Arg Val Arg Ser Glu
            340                 345                 350

Thr Ala Pro Tyr Leu Gln Lys Arg Leu Arg Glu Leu Ser Asp His Pro
        355                 360                 365

Leu Val Gly Glu Val Arg Gly Val Gly Leu Leu Gly Ala Ile Glu Leu
    370                 375                 380

Val Lys Asp Lys Thr Thr Arg Glu Arg Tyr Thr Asp Lys Gly Ala Gly
385                 390                 395                 400

Met Ile Cys Arg Thr Phe Cys Phe Asp Asn Gly Leu Ile Met Arg Ala
                405                 410                 415
```

```
Val Gly Asp Thr Met Ile Ile Ala Pro Pro Leu Val Ile Ser Phe Ala
            420                 425                 430

Gln Ile Asp Glu Leu Val Glu Lys Ala Arg Thr Cys Leu Asp Leu Thr
        435                 440                 445

Leu Ala Val Leu Gln Gly
    450

<210> SEQ ID NO 13
<211> LENGTH: 1365
<212> TYPE: DNA
<213> ORGANISM: Artificial
<220> FEATURE:
<223> OTHER INFORMATION: Pseudomonas syringae codon optimised
      aminotransferase gene

<400> SEQUENCE: 13
atgtctgcta acaatccaca aactctggaa tggcaggcac tgagctccga acatcacctg      60
gctccgttct ccgactacaa caactgaaa gagaaaggcc cgcgtatcat tacccgcgct     120
gaaggtgtgt acctgtggga ttctgaaggc aacaaaattc tggacggtat gagcggcctg     180
tggtgcgtag caatcggtta tggccgtgaa gaactggctg acgcggcgag caaacagatg     240
cgtgaactgc gtattataa cctgttcttc aaaccgcac acccgccggt tctggaactg     300
gctaaagcta tcagcgatat cgcaccggag ggcatgaatc acgtcttctt cactggttcc     360
ggtagcgaag caacgacac gatgctgcgc atggtacgtc actattgggc gctgaagggc     420
cagccgaaca gaaaacgat tatcagccgt gtaaacggtt atcacggcag caccgttgcg     480
ggtgcgagcc tgggcggtat gacctacatg cacgaacagg gtgacctgcc gatcccgggt     540
gtagtgcaca ttccgcagcc gtattggttc ggtgaaggcg gtgacatgac gccggacgaa     600
ttcggcatct gggcggcaga gcagctggaa aagaaaatcc tggaactggg cgtggaaaac     660
gtcggcgcgt tcatcgcgga accgattcag ggcgcgggcg cgtaattgt tccgccggac     720
agctactggc aaaaaatcaa agagatcctg tctcgttacg acatcctgtt cgccgcagac     780
gaagtgatct gcggttttgg ccgcacctct gaatggttcg ctccgacttc tacggtctg      840
cgtccggaca tgatgaccat cgccaaaggc ctgacctccg ttatgttcc tatgggtggc     900
ctgatcgtgc gcacgaaat tgttgcggtt ctgaacgaag cggcgattt caaccacggc     960
ttcacctatt ccggtcaccc agttgctgct gctgtagcac tggaaaacat ccgcatcctg    1020
cgtgaagaaa agatcgtaga acgcgtacgt tccgaaaccg caccttacct gcagaagcgc    1080
ctgcgcgaac tgagcgacca ccctctggta ggtgaagttc gcggcgtggg cctgctgggc    1140
gcgatcgagc tggtgaaaga caaaactacc cgtgaacgtt acaccgacaa aggcgcaggc    1200
atgatctgcc gtaccttttg cttcgataac ggtctgatca tgcgcgcagt cggtgatacc    1260
atgatcattg ctccgcctct ggttatttct tttgcccaga ttgatgagct ggtcgaaaaa    1320
gcgcgcactt gtctggatct gactctggct gttctgcagg gttaa                    1365

<210> SEQ ID NO 14
<211> LENGTH: 849
<212> TYPE: DNA
<213> ORGANISM: Bacillus subtilis
<220> FEATURE:
<221> NAME/KEY: CDS
<222> LOCATION: (1)..(849)

<400> SEQUENCE: 14 atg aag gtt tta gtc aat ggc cgg ctg att ggg cgc agt gaa gca tca      48
Met Lys Val Leu Val Asn Gly Arg Leu Ile Gly Arg Ser Glu Ala Ser
1               5                   10                  15
```

```
atc gat ttg gaa gat cgc ggt tat cag ttt ggt gac ggc atc tat gaa    96
Ile Asp Leu Glu Asp Arg Gly Tyr Gln Phe Gly Asp Gly Ile Tyr Glu
         20                  25                  30 gtg atc agg gtg tac aaa gga gta ttg ttc ggc tta cgt gag cat gca   144
Val Ile Arg Val Tyr Lys Gly Val Leu Phe Gly Leu Arg Glu His Ala
 35                  40                  45 gag cgt ttt ttc aga agt gct gct gaa atc gga att tca ctg cca ttc   192
Glu Arg Phe Phe Arg Ser Ala Ala Glu Ile Gly Ile Ser Leu Pro Phe
     50                  55                  60 agt ata gaa gat ctc gag tgg gac ctg caa aag ctt gta cag gaa aat   240
Ser Ile Glu Asp Leu Glu Trp Asp Leu Gln Lys Leu Val Gln Glu Asn
 65                  70                  75                  80 gcg gtc agt gag gga gcg gta tac att cag aca aca aga ggt gtg gcc   288
Ala Val Ser Glu Gly Ala Val Tyr Ile Gln Thr Thr Arg Gly Val Ala
                 85                  90                  95 ccg cga aaa cac cag tat gaa gcc ggc ctc gag ccg cag act act gcc   336
Pro Arg Lys His Gln Tyr Glu Ala Gly Leu Glu Pro Gln Thr Thr Ala
             100                 105                 110 tat acg ttt acg gtg aaa aaa ccg gag caa gag cag gca tac gga gtg   384
Tyr Thr Phe Thr Val Lys Lys Pro Glu Gln Glu Gln Ala Tyr Gly Val
         115                 120                 125 gcg gcc att aca gat gag gat ctt cgc tgg tta aga tgt gat atc aaa   432
Ala Ala Ile Thr Asp Glu Asp Leu Arg Trp Leu Arg Cys Asp Ile Lys
130                 135                 140 agt ctg aat tta ctg tat aat gtc atg acg aag caa agg gcc tat gaa   480
Ser Leu Asn Leu Leu Tyr Asn Val Met Thr Lys Gln Arg Ala Tyr Glu
145                 150                 155                 160 gcc gga gca ttt gaa gcc att tta ctt agg gac ggc gtt gtt acg gag   528
Ala Gly Ala Phe Glu Ala Ile Leu Leu Arg Asp Gly Val Val Thr Glu
                165                 170                 175 ggt aca tcc tct aac gtt tat gcc gtt atc aac ggc aca gtg cga aca   576
Gly Thr Ser Ser Asn Val Tyr Ala Val Ile Asn Gly Thr Val Arg Thr
            180                 185                 190 cat ccg gct aat cgg ctc att ctc aat gga att aca cgg atg aat att   624
His Pro Ala Asn Arg Leu Ile Leu Asn Gly Ile Thr Arg Met Asn Ile
        195                 200                 205 tta gga ctg att gag aag aat ggg atc aaa ctg gat gag act cct gtc   672
Leu Gly Leu Ile Glu Lys Asn Gly Ile Lys Leu Asp Glu Thr Pro Val
    210                 215                 220 agt gaa gaa gag ttg aaa cag gcg gaa gag atc ttt att tcg tca acg   720
Ser Glu Glu Glu Leu Lys Gln Ala Glu Glu Ile Phe Ile Ser Ser Thr
225                 230                 235                 240 acg gca gaa att att ccg gtc gtg acg ctc gat gga caa tcg atc gga   768
Thr Ala Glu Ile Ile Pro Val Val Thr Leu Asp Gly Gln Ser Ile Gly
                245                 250                 255 agc ggg aaa ccc gga ccg gtg acc aaa cag ctt cag gct gct ttt caa   816
Ser Gly Lys Pro Gly Pro Val Thr Lys Gln Leu Gln Ala Ala Phe Gln
            260                 265                 270 gaa agc att caa cag gct gct agc att tca taa                       849
Glu Ser Ile Gln Gln Ala Ala Ser Ile Ser
        275                 280

<210> SEQ ID NO 15
<211> LENGTH: 282
<212> TYPE: PRT
<213> ORGANISM: Bacillus subtilis

<400> SEQUENCE: 15

Met Lys Val Leu Val Asn Gly Arg Leu Ile Gly Arg Ser Glu Ala Ser
1               5                   10                  15
```

```
Ile Asp Leu Glu Asp Arg Gly Tyr Gln Phe Gly Asp Gly Ile Tyr Glu
            20                  25                  30

Val Ile Arg Val Tyr Lys Gly Val Leu Phe Gly Leu Arg Glu His Ala
        35                  40                  45

Glu Arg Phe Phe Arg Ser Ala Ala Glu Ile Gly Ile Ser Leu Pro Phe
    50                  55                  60

Ser Ile Glu Asp Leu Glu Trp Asp Leu Gln Lys Leu Val Gln Glu Asn
65                  70                  75                  80

Ala Val Ser Glu Gly Ala Val Tyr Ile Gln Thr Thr Arg Gly Val Ala
                85                  90                  95

Pro Arg Lys His Gln Tyr Glu Ala Gly Leu Glu Pro Thr Thr Ala
            100                 105                 110

Tyr Thr Phe Thr Val Lys Lys Pro Glu Gln Glu Gln Ala Tyr Gly Val
        115                 120                 125

Ala Ala Ile Thr Asp Glu Asp Leu Arg Trp Leu Arg Cys Asp Ile Lys
    130                 135                 140

Ser Leu Asn Leu Leu Tyr Asn Val Met Thr Lys Gln Arg Ala Tyr Glu
145                 150                 155                 160

Ala Gly Ala Phe Glu Ala Ile Leu Leu Arg Asp Gly Val Val Thr Glu
                165                 170                 175

Gly Thr Ser Ser Asn Val Tyr Ala Val Ile Asn Gly Thr Val Arg Thr
            180                 185                 190

His Pro Ala Asn Arg Leu Ile Leu Asn Gly Ile Thr Arg Met Asn Ile
        195                 200                 205

Leu Gly Leu Ile Glu Lys Asn Gly Ile Lys Leu Asp Glu Thr Pro Val
    210                 215                 220

Ser Glu Glu Glu Leu Lys Gln Ala Glu Glu Ile Phe Ile Ser Ser Thr
225                 230                 235                 240

Thr Ala Glu Ile Ile Pro Val Val Thr Leu Asp Gly Gln Ser Ile Gly
                245                 250                 255

Ser Gly Lys Pro Gly Pro Val Thr Lys Gln Leu Gln Ala Ala Phe Gln
            260                 265                 270

Glu Ser Ile Gln Gln Ala Ala Ser Ile Ser
        275                 280

<210> SEQ ID NO 16
<211> LENGTH: 1347
<212> TYPE: DNA
<213> ORGANISM: Bacillus subtilis
<220> FEATURE:
<221> NAME/KEY: CDS
<222> LOCATION: (1)..(1347)

<400> SEQUENCE: 16 atg act cat gat ttg ata gaa aaa agt aaa aag cac ctc tgg ctg cca      48
Met Thr His Asp Leu Ile Glu Lys Ser Lys Lys His Leu Trp Leu Pro
1               5                   10                  15 ttt acc caa atg aaa gat tat gat gaa aac ccc tta atc atc gaa agc      96
Phe Thr Gln Met Lys Asp Tyr Asp Glu Asn Pro Leu Ile Ile Glu Ser
            20                  25                  30 ggg act gga atc aaa gtc aaa gac ata aac ggc aag gaa tac tat gac     144
Gly Thr Gly Ile Lys Val Lys Asp Ile Asn Gly Lys Glu Tyr Tyr Asp
        35                  40                  45 ggt ttt tca tcg gtt tgg ctt aat gtc cac gga cac gcg aaa aaa gaa     192
Gly Phe Ser Ser Val Trp Leu Asn Val His Gly His Arg Lys Lys Glu
    50                  55                  60 cta gat gac gcc ata aaa aaa cag ctc gga aaa att gcg cac tcc acg     240
Leu Asp Asp Ala Ile Lys Lys Gln Leu Gly Lys Ile Ala His Ser Thr
```

|     |     |     |     |     |     |     |     |     |     |     |     |     |     |     |     |      |
|---|---|---|---|---|---|---|---|---|---|---|---|---|---|---|---|---|
| tta | ttg | ggc | atg | acc | aat | gtt | cca | gca | acc | cag | ctt | gcc | gaa | aca | tta | 288 |
| Leu | Leu | Gly | Met | Thr | Asn | Val | Pro | Ala | Thr | Gln | Leu | Ala | Glu | Thr | Leu |  |
|  |  |  |  | 85 |  |  |  |  | 90 |  |  |  |  | 95 |  |  |
| atc | gac | atc | agc | cca | aaa | aag | ctc | acg | cgg | gtc | ttt | tat | tca | gac | agc | 336 |
| Ile | Asp | Ile | Ser | Pro | Lys | Lys | Leu | Thr | Arg | Val | Phe | Tyr | Ser | Asp | Ser |  |
|  |  |  | 100 |  |  |  |  | 105 |  |  |  |  | 110 |  |  |  |
| ggc | gca | gag | gcg | atg | gaa | ata | gcc | cta | aaa | atg | gcg | ttt | cag | tat | tgg | 384 |
| Gly | Ala | Glu | Ala | Met | Glu | Ile | Ala | Leu | Lys | Met | Ala | Phe | Gln | Tyr | Trp |  |
|  |  | 115 |  |  |  |  | 120 |  |  |  |  | 125 |  |  |  |  |
| aag | aac | atc | ggg | aag | ccc | gag | aaa | caa | aaa | ttc | atc | gca | atg | aaa | aac | 432 |
| Lys | Asn | Ile | Gly | Lys | Pro | Glu | Lys | Gln | Lys | Phe | Ile | Ala | Met | Lys | Asn |  |
| 130 |  |  |  |  | 135 |  |  |  |  | 140 |  |  |  |  |  |  |
| ggg | tat | cac | ggt | gat | acg | att | ggc | gcc | gtc | agt | gtc | ggt | tca | att | gag | 480 |
| Gly | Tyr | His | Gly | Asp | Thr | Ile | Gly | Ala | Val | Ser | Val | Gly | Ser | Ile | Glu |  |
| 145 |  |  |  |  | 150 |  |  |  |  | 155 |  |  |  |  | 160 |  |
| ctt | ttt | cac | cac | gta | tac | ggc | ccg | ttg | atg | ttc | gag | agt | tac | aag | gcc | 528 |
| Leu | Phe | His | His | Val | Tyr | Gly | Pro | Leu | Met | Phe | Glu | Ser | Tyr | Lys | Ala |  |
|  |  |  |  | 165 |  |  |  |  | 170 |  |  |  |  | 175 |  |  |
| ccg | att | cct | tat | gtg | tat | cgt | tct | gaa | agc | ggt | gat | cct | gat | gag | tgc | 576 |
| Pro | Ile | Pro | Tyr | Val | Tyr | Arg | Ser | Glu | Ser | Gly | Asp | Pro | Asp | Glu | Cys |  |
|  |  |  | 180 |  |  |  |  | 185 |  |  |  |  | 190 |  |  |  |
| cgt | gat | cag | tgc | ctc | cga | gag | ctt | gca | cag | ctg | ctt | gag | gaa | cat | cat | 624 |
| Arg | Asp | Gln | Cys | Leu | Arg | Glu | Leu | Ala | Gln | Leu | Leu | Glu | Glu | His | His |  |
|  |  | 195 |  |  |  |  | 200 |  |  |  |  | 205 |  |  |  |  |
| gag | gaa | att | gcc | gcg | ctt | tcc | att | gaa | tca | atg | gta | caa | ggc | gcg | tcc | 672 |
| Glu | Glu | Ile | Ala | Ala | Leu | Ser | Ile | Glu | Ser | Met | Val | Gln | Gly | Ala | Ser |  |
| 210 |  |  |  |  | 215 |  |  |  |  | 220 |  |  |  |  |  |  |
| ggt | atg | atc | gtg | atg | ccg | gaa | gga | tat | ttg | gca | ggc | gtg | cgc | gag | cta | 720 |
| Gly | Met | Ile | Val | Met | Pro | Glu | Gly | Tyr | Leu | Ala | Gly | Val | Arg | Glu | Leu |  |
| 225 |  |  |  |  | 230 |  |  |  |  | 235 |  |  |  |  | 240 |  |
| tgt | aca | aca | tac | gat | gtc | tta | atg | atc | gtt | gat | gaa | gtc | gct | aca | ggc | 768 |
| Cys | Thr | Thr | Tyr | Asp | Val | Leu | Met | Ile | Val | Asp | Glu | Val | Ala | Thr | Gly |  |
|  |  |  |  | 245 |  |  |  |  | 250 |  |  |  |  | 255 |  |  |
| ttt | ggc | cgt | aca | gga | aaa | atg | ttt | gcg | tgc | gag | cac | gag | aat | gtc | cag | 816 |
| Phe | Gly | Arg | Thr | Gly | Lys | Met | Phe | Ala | Cys | Glu | His | Glu | Asn | Val | Gln |  |
|  |  |  | 260 |  |  |  |  | 265 |  |  |  |  | 270 |  |  |  |
| cct | gat | ctg | atg | gct | gcc | ggt | aaa | ggc | att | aca | gga | ggc | tat | ttg | cca | 864 |
| Pro | Asp | Leu | Met | Ala | Ala | Gly | Lys | Gly | Ile | Thr | Gly | Gly | Tyr | Leu | Pro |  |
|  |  | 275 |  |  |  |  | 280 |  |  |  |  | 285 |  |  |  |  |
| att | gcc | gtt | acg | ttt | gcc | act | gaa | gac | atc | tat | aag | gca | ttc | tat | gat | 912 |
| Ile | Ala | Val | Thr | Phe | Ala | Thr | Glu | Asp | Ile | Tyr | Lys | Ala | Phe | Tyr | Asp |  |
| 290 |  |  |  |  | 295 |  |  |  |  | 300 |  |  |  |  |  |  |
| gat | tat | gaa | aac | cta | aaa | acc | ttt | ttc | cat | ggc | cat | tcc | tat | aca | ggc | 960 |
| Asp | Tyr | Glu | Asn | Leu | Lys | Thr | Phe | Phe | His | Gly | His | Ser | Tyr | Thr | Gly |  |
| 305 |  |  |  |  | 310 |  |  |  |  | 315 |  |  |  |  | 320 |  |
| aat | cag | ctt | ggc | tgt | gcg | gtt | gcg | ctt | gaa | aat | ctg | gca | tta | ttt | gaa | 1008 |
| Asn | Gln | Leu | Gly | Cys | Ala | Val | Ala | Leu | Glu | Asn | Leu | Ala | Leu | Phe | Glu |  |
|  |  |  |  | 325 |  |  |  |  | 330 |  |  |  |  | 335 |  |  |
| tct | gaa | aac | att | gtg | gaa | caa | gta | gcg | gaa | aaa | agt | aaa | aag | ctc | cat | 1056 |
| Ser | Glu | Asn | Ile | Val | Glu | Gln | Val | Ala | Glu | Lys | Ser | Lys | Lys | Leu | His |  |
|  |  |  | 340 |  |  |  |  | 345 |  |  |  |  | 350 |  |  |  |
| ttt | ctt | ctt | caa | gat | ctg | cac | gct | ctt | cct | cat | gtt | ggg | gat | att | cgg | 1104 |
| Phe | Leu | Leu | Gln | Asp | Leu | His | Ala | Leu | Pro | His | Val | Gly | Asp | Ile | Arg |  |
|  |  | 355 |  |  |  |  | 360 |  |  |  |  | 365 |  |  |  |  |
| cag | ctt | ggc | ttt | atg | tgc | ggt | gca | gag | ctt | gta | cga | tca | aag | gaa | act | 1152 |
| Gln | Leu | Gly | Phe | Met | Cys | Gly | Ala | Glu | Leu | Val | Arg | Ser | Lys | Glu | Thr |  |
| 370 |  |  |  |  | 375 |  |  |  |  | 380 |  |  |  |  |  |  |
| aaa | gaa | cct | tac | ccg | gct | gat | cgg | cgg | att | gga | tac | aaa | gtt | tcc | tta | 1200 |
| Lys | Glu | Pro | Tyr | Pro | Ala | Asp | Arg | Arg | Ile | Gly | Tyr | Lys | Val | Ser | Leu |  |

```
                385                 390                 395                 400
aaa atg aga gag tta gga atg ctg aca aga ccg ctt ggg gac gtg att         1248
Lys Met Arg Glu Leu Gly Met Leu Thr Arg Pro Leu Gly Asp Val Ile
                405                 410                 415 gca ttt ctt cct cct ctt gcc agc aca gct gaa gag ctc tcg gaa atg         1296
Ala Phe Leu Pro Pro Leu Ala Ser Thr Ala Glu Glu Leu Ser Glu Met
            420                 425                 430 gtt gcc att atg aaa caa gcg atc cac gag gtt acg agc ctt gaa gat         1344
Val Ala Ile Met Lys Gln Ala Ile His Glu Val Thr Ser Leu Glu Asp
        435                 440                 445 tga                                                                     1347

<210> SEQ ID NO 17
<211> LENGTH: 448
<212> TYPE: PRT
<213> ORGANISM: Bacillus subtilis

<400> SEQUENCE: 17

Met Thr His Asp Leu Ile Glu Lys Ser Lys His Leu Trp Leu Pro
1               5                   10                  15

Phe Thr Gln Met Lys Asp Tyr Asp Glu Asn Pro Leu Ile Ile Glu Ser
                20                  25                  30

Gly Thr Gly Ile Lys Val Lys Asp Ile Asn Gly Lys Glu Tyr Tyr Asp
            35                  40                  45

Gly Phe Ser Ser Val Trp Leu Asn Val His Gly His Arg Lys Lys Glu
        50                  55                  60

Leu Asp Asp Ala Ile Lys Lys Gln Leu Gly Lys Ile Ala His Ser Thr
65                  70                  75                  80

Leu Leu Gly Met Thr Asn Val Pro Ala Thr Gln Leu Ala Glu Thr Leu
                85                  90                  95

Ile Asp Ile Ser Pro Lys Lys Leu Thr Arg Val Phe Tyr Ser Asp Ser
            100                 105                 110

Gly Ala Glu Ala Met Glu Ile Ala Leu Lys Met Ala Phe Gln Tyr Trp
        115                 120                 125

Lys Asn Ile Gly Lys Pro Glu Lys Gln Lys Phe Ile Ala Met Lys Asn
    130                 135                 140

Gly Tyr His Gly Asp Thr Ile Gly Ala Val Ser Val Gly Ser Ile Glu
145                 150                 155                 160

Leu Phe His His Val Tyr Gly Pro Leu Met Phe Glu Ser Tyr Lys Ala
                165                 170                 175

Pro Ile Pro Tyr Val Tyr Arg Ser Glu Ser Gly Asp Pro Asp Glu Cys
            180                 185                 190

Arg Asp Gln Cys Leu Arg Glu Leu Ala Gln Leu Leu Glu Glu His His
        195                 200                 205

Glu Glu Ile Ala Ala Leu Ser Ile Glu Ser Met Val Gln Gly Ala Ser
    210                 215                 220

Gly Met Ile Val Met Pro Glu Gly Tyr Leu Ala Gly Val Arg Glu Leu
225                 230                 235                 240

Cys Thr Thr Tyr Asp Val Leu Met Ile Val Asp Glu Val Ala Thr Gly
                245                 250                 255

Phe Gly Arg Thr Gly Lys Met Phe Ala Cys Glu His Glu Asn Val Gln
            260                 265                 270

Pro Asp Leu Met Ala Ala Gly Lys Gly Ile Thr Gly Gly Tyr Leu Pro
        275                 280                 285

Ile Ala Val Thr Phe Ala Thr Glu Asp Ile Tyr Lys Ala Phe Tyr Asp
    290                 295                 300
```

```
Asp Tyr Glu Asn Leu Lys Thr Phe Phe His Gly His Ser Tyr Thr Gly
305                 310                 315                 320

Asn Gln Leu Gly Cys Ala Val Ala Leu Glu Asn Leu Ala Leu Phe Glu
            325                 330                 335

Ser Glu Asn Ile Val Glu Gln Val Ala Glu Lys Ser Lys Lys Leu His
            340                 345                 350

Phe Leu Leu Gln Asp Leu His Ala Leu Pro His Val Gly Asp Ile Arg
            355                 360                 365

Gln Leu Gly Phe Met Cys Gly Ala Glu Leu Val Arg Ser Lys Glu Thr
        370                 375                 380

Lys Glu Pro Tyr Pro Ala Asp Arg Arg Ile Gly Tyr Lys Val Ser Leu
385                 390                 395                 400

Lys Met Arg Glu Leu Gly Met Leu Thr Arg Pro Leu Gly Asp Val Ile
                405                 410                 415

Ala Phe Leu Pro Pro Leu Ala Ser Thr Ala Glu Glu Leu Ser Glu Met
            420                 425                 430

Val Ala Ile Met Lys Gln Ala Ile His Glu Val Thr Ser Leu Glu Asp
            435                 440                 445

<210> SEQ ID NO 18
<211> LENGTH: 1467
<212> TYPE: DNA
<213> ORGANISM: Rhodobacter sphaeroides
<220> FEATURE:
<221> NAME/KEY: CDS
<222> LOCATION: (1)..(1467)

<400> SEQUENCE: 18 atg ccc ggt tgc ggg ggc ttg ccc ggg aat gaa ccg aaa tgc gga cga      48
Met Pro Gly Cys Gly Gly Leu Pro Gly Asn Glu Pro Lys Cys Gly Arg
1               5                   10                  15 gag ggg agg tcg gcg atg acg cgg aat gac gcg acg aat gct gcc gga      96
Glu Gly Arg Ser Ala Met Thr Arg Asn Asp Ala Thr Asn Ala Ala Gly
            20                  25                  30 gcg gtg ggc gcg gcg atg cgg gat cac atc ctc ttg cct gca cag gaa      144
Ala Val Gly Ala Ala Met Arg Asp His Ile Leu Leu Pro Ala Gln Glu
        35                  40                  45 atg gcg aag ctc ggc aag tcc gcg cag ccg gtg ctg act cat gcc gag      192
Met Ala Lys Leu Gly Lys Ser Ala Gln Pro Val Leu Thr His Ala Glu
    50                  55                  60 ggc atc tat gtc cat acc gag gac ggc cgc cgc ctg atc gac ggg ccg      240
Gly Ile Tyr Val His Thr Glu Asp Gly Arg Arg Leu Ile Asp Gly Pro
65                  70                  75                  80 gcg ggc atg tgg tgc gcg cag gtg ggc tac ggc cgc cgc gag atc gtc      288
Ala Gly Met Trp Cys Ala Gln Val Gly Tyr Gly Arg Arg Glu Ile Val
                85                  90                  95 gat gcc atg gcg cat cag gcg atg gtg ctg ccc tat gcc tcg ccc tgg      336
Asp Ala Met Ala His Gln Ala Met Val Leu Pro Tyr Ala Ser Pro Trp
            100                 105                 110 tat atg gcc acg agc ccc gcg gcg cgg ctg gcg gag aag atc gcc acg      384
Tyr Met Ala Thr Ser Pro Ala Ala Arg Leu Ala Glu Lys Ile Ala Thr
        115                 120                 125 ctg acg ccg ggc gat ctc aac cgg atc ttt ttc acc acg ggc ggg tcg      432
Leu Thr Pro Gly Asp Leu Asn Arg Ile Phe Phe Thr Thr Gly Gly Ser
    130                 135                 140 acc gcg gtg gac agc gcg ctg cgc ttc tcg gaa ttc tac aac aac gtg      480
Thr Ala Val Asp Ser Ala Leu Arg Phe Ser Glu Phe Tyr Asn Asn Val
145                 150                 155                 160 ctg ggc cgg ccg cag aag aag cgc atc atc gtg cgc tac gac ggc tat      528
```

```
                Leu Gly Arg Pro Gln Lys Lys Arg Ile Ile Val Arg Tyr Asp Gly Tyr
                                165                 170                 175 cac ggc tcg acg gcg ctc acc gcc gcc tgc acc ggc cgc acc ggc aac        576
His Gly Ser Thr Ala Leu Thr Ala Ala Cys Thr Gly Arg Thr Gly Asn
            180                 185                 190 tgg ccg aac ttc gac atc gcg cag gac cgg atc tcg ttc ctc tcg agc        624
Trp Pro Asn Phe Asp Ile Ala Gln Asp Arg Ile Ser Phe Leu Ser Ser
        195                 200                 205 ccc aat ccg cgc cac gcc ggc aac cgc agc cag gag gcg ttc ctc gac        672
Pro Asn Pro Arg His Ala Gly Asn Arg Ser Gln Glu Ala Phe Leu Asp
    210                 215                 220 gat ctg gtg cag gaa ttc gag gac cgg atc gag agc ctc ggc ccc gac        720
Asp Leu Val Gln Glu Phe Glu Asp Arg Ile Glu Ser Leu Gly Pro Asp
225                 230                 235                 240 acg atc gcg gcc ttc ctg gcc gag ccg atc ctc gcc tcg ggc ggc gtc        768
Thr Ile Ala Ala Phe Leu Ala Glu Pro Ile Leu Ala Ser Gly Gly Val
                245                 250                 255 att att ccg ccc gca ggc tat cat gcg cgc ttc aag gcg atc tgc gag        816
Ile Ile Pro Pro Ala Gly Tyr His Ala Arg Phe Lys Ala Ile Cys Glu
            260                 265                 270 aag cac gac atc ctc tat atc tcg gac gag gtg gtg acg ggc ttc ggc        864
Lys His Asp Ile Leu Tyr Ile Ser Asp Glu Val Val Thr Gly Phe Gly
        275                 280                 285 cgt tgc ggc gag tgg ttc gcc tcg gag aag gtg ttc ggg gtg gtg ccg        912
Arg Cys Gly Glu Trp Phe Ala Ser Glu Lys Val Phe Gly Val Val Pro
    290                 295                 300 gac atc atc acc ttc gcc aag ggc gtg acc tcg ggc tat gtg ccg ctc        960
Asp Ile Ile Thr Phe Ala Lys Gly Val Thr Ser Gly Tyr Val Pro Leu
305                 310                 315                 320 ggc ggc ctt gcg atc tcc gag gcg gtg ctg gcg cgg atc tcg ggc gag       1008
Gly Gly Leu Ala Ile Ser Glu Ala Val Leu Ala Arg Ile Ser Gly Glu
                325                 330                 335 aat gcc aag gga agc tgg ttc acc aac ggc tat acc tac agc aat cag       1056
Asn Ala Lys Gly Ser Trp Phe Thr Asn Gly Tyr Thr Tyr Ser Asn Gln
            340                 345                 350 ccg gtg gcc tgc gcc gcg gcg ctt gcc aac atc gag ctg atg gag cgc       1104
Pro Val Ala Cys Ala Ala Ala Leu Ala Asn Ile Glu Leu Met Glu Arg
        355                 360                 365 gag ggc atc gtc gat cag gcg cgc gag atg gcg gac tat ttc gcc gcg       1152
Glu Gly Ile Val Asp Gln Ala Arg Glu Met Ala Asp Tyr Phe Ala Ala
    370                 375                 380 gcg ctg gct tcg ctg cgc gat ctg ccg ggc gtg gcg gaa acc cgg tcg       1200
Ala Leu Ala Ser Leu Arg Asp Leu Pro Gly Val Ala Glu Thr Arg Ser
385                 390                 395                 400 gtg ggc ctc gtg ggt tgc gtg caa tgc ctg ctc gac ccg acc cgg gcg       1248
Val Gly Leu Val Gly Cys Val Gln Cys Leu Leu Asp Pro Thr Arg Ala
                405                 410                 415 gac ggc acg gcc gag gac aag gcc ttc acc ctg aag atc gac gag cgc       1296
Asp Gly Thr Ala Glu Asp Lys Ala Phe Thr Leu Lys Ile Asp Glu Arg
            420                 425                 430 tgc ttc gag ctc ggg ctg atc gtg cgc ccg ctg ggc gat ctc tgc gtg       1344
Cys Phe Glu Leu Gly Leu Ile Val Arg Pro Leu Gly Asp Leu Cys Val
        435                 440                 445 atc tcg ccg ccg ctc atc atc tcg cgc gcg cag atc gac gag atg gtc       1392
Ile Ser Pro Pro Leu Ile Ile Ser Arg Ala Gln Ile Asp Glu Met Val
    450                 455                 460 gcg atc atg cgg cag gcc atc acc gaa gtg agc gcc gcc cac ggt ctg       1440
Ala Ile Met Arg Gln Ala Ile Thr Glu Val Ser Ala Ala His Gly Leu
465                 470                 475                 480 acc gcg aaa gaa ccg gcc gcc gtc tga                                    1467
```

Thr Ala Lys Glu Pro Ala Ala Val
                485

<210> SEQ ID NO 19
<211> LENGTH: 488
<212> TYPE: PRT
<213> ORGANISM: Rhodobacter sphaeroides

<400> SEQUENCE: 19

Met Pro Gly Cys Gly Gly Leu Pro Gly Asn Glu Pro Lys Cys Gly Arg
1               5                   10                  15

Glu Gly Arg Ser Ala Met Thr Arg Asn Asp Ala Thr Asn Ala Ala Gly
            20                  25                  30

Ala Val Gly Ala Ala Met Arg Asp His Ile Leu Leu Pro Ala Gln Glu
        35                  40                  45

Met Ala Lys Leu Gly Lys Ser Ala Gln Pro Val Leu Thr His Ala Glu
    50                  55                  60

Gly Ile Tyr Val His Thr Glu Asp Gly Arg Arg Leu Ile Asp Gly Pro
65                  70                  75                  80

Ala Gly Met Trp Cys Ala Gln Val Gly Tyr Gly Arg Arg Glu Ile Val
                85                  90                  95

Asp Ala Met Ala His Gln Ala Met Val Leu Pro Tyr Ala Ser Pro Trp
            100                 105                 110

Tyr Met Ala Thr Ser Pro Ala Ala Arg Leu Ala Glu Lys Ile Ala Thr
        115                 120                 125

Leu Thr Pro Gly Asp Leu Asn Arg Ile Phe Phe Thr Thr Gly Gly Ser
    130                 135                 140

Thr Ala Val Asp Ser Ala Leu Arg Phe Ser Glu Phe Tyr Asn Asn Val
145                 150                 155                 160

Leu Gly Arg Pro Gln Lys Lys Arg Ile Val Arg Tyr Asp Gly Tyr
            165                 170                 175

His Gly Ser Thr Ala Leu Thr Ala Ala Cys Thr Gly Arg Thr Gly Asn
        180                 185                 190

Trp Pro Asn Phe Asp Ile Ala Gln Asp Arg Ile Ser Phe Leu Ser Ser
    195                 200                 205

Pro Asn Pro Arg His Ala Gly Asn Arg Ser Gln Glu Ala Phe Leu Asp
    210                 215                 220

Asp Leu Val Gln Glu Phe Glu Asp Arg Ile Glu Ser Leu Gly Pro Asp
225                 230                 235                 240

Thr Ile Ala Ala Phe Leu Ala Glu Pro Ile Leu Ala Ser Gly Gly Val
                245                 250                 255

Ile Ile Pro Pro Ala Gly Tyr His Ala Arg Phe Lys Ala Ile Cys Glu
            260                 265                 270

Lys His Asp Ile Leu Tyr Ile Ser Asp Glu Val Val Thr Gly Phe Gly
    275                 280                 285

Arg Cys Gly Glu Trp Phe Ala Ser Glu Lys Val Phe Gly Val Val Pro
    290                 295                 300

Asp Ile Ile Thr Phe Ala Lys Gly Val Thr Ser Gly Tyr Val Pro Leu
305                 310                 315                 320

Gly Gly Leu Ala Ile Ser Glu Ala Val Leu Ala Arg Ile Ser Gly Glu
                325                 330                 335

Asn Ala Lys Gly Ser Trp Phe Thr Asn Gly Tyr Thr Tyr Ser Asn Gln
            340                 345                 350

Pro Val Ala Cys Ala Ala Leu Ala Asn Ile Glu Leu Met Glu Arg
        355                 360                 365

```
Glu Gly Ile Val Asp Gln Ala Arg Glu Met Ala Asp Tyr Phe Ala Ala
    370                 375                 380

Ala Leu Ala Ser Leu Arg Asp Leu Pro Gly Val Ala Glu Thr Arg Ser
385                 390                 395                 400

Val Gly Leu Val Gly Cys Val Gln Cys Leu Leu Asp Pro Thr Arg Ala
                405                 410                 415

Asp Gly Thr Ala Glu Asp Lys Ala Phe Thr Leu Lys Ile Asp Glu Arg
            420                 425                 430

Cys Phe Glu Leu Gly Leu Ile Val Arg Pro Leu Gly Asp Leu Cys Val
        435                 440                 445

Ile Ser Pro Pro Leu Ile Ile Ser Arg Ala Gln Ile Asp Glu Met Val
    450                 455                 460

Ala Ile Met Arg Gln Ala Ile Thr Glu Val Ser Ala Ala His Gly Leu
465                 470                 475                 480

Thr Ala Lys Glu Pro Ala Ala Val
                485

<210> SEQ ID NO 20
<211> LENGTH: 837
<212> TYPE: DNA
<213> ORGANISM: Legionella pneumophila
<220> FEATURE:
<221> NAME/KEY: CDS
<222> LOCATION: (1)..(837)

<400> SEQUENCE: 20
atg agt atc gca ttt gtt aac ggc aag tat tgt tgt caa tct gaa gca       48
Met Ser Ile Ala Phe Val Asn Gly Lys Tyr Cys Cys Gln Ser Glu Ala
1               5                   10                  15
aaa att tca ata ttt gat cga ggg ttt ctt ttt ggt gac tcg gtt tat       96
Lys Ile Ser Ile Phe Asp Arg Gly Phe Leu Phe Gly Asp Ser Val Tyr
            20                  25                  30
gaa gtg ctg cct gtt tac cat ggg cag cct tac ttt gta gac caa cat      144
Glu Val Leu Pro Val Tyr His Gly Gln Pro Tyr Phe Val Asp Gln His
        35                  40                  45
ctt gac cga tta ttc tca aat atg aaa aaa att aag atg att ata cca      192
Leu Asp Arg Leu Phe Ser Asn Met Lys Lys Ile Lys Met Ile Ile Pro
    50                  55                  60
aat tat gat tgg cat ggt tta att cat aga cta ata tca gaa aat aat      240
Asn Tyr Asp Trp His Gly Leu Ile His Arg Leu Ile Ser Glu Asn Asn
65                  70                  75                  80
ggc ggt aat tta caa gta tat atc caa gtc aca cga ggg aat caa ggg      288
Gly Gly Asn Leu Gln Val Tyr Ile Gln Val Thr Arg Gly Asn Gln Gly
                85                  90                  95
gtg cgc aag cat gat atc cct act tcc atc aca cct tct gtt atc gca      336
Val Arg Lys His Asp Ile Pro Thr Ser Ile Thr Pro Ser Val Ile Ala
            100                 105                 110
ttc act atg cat aat cca ttt ccc acc ctc gaa gat aag gaa cag gga      384
Phe Thr Met His Asn Pro Phe Pro Thr Leu Glu Asp Lys Glu Gln Gly
        115                 120                 125
atg tca gca aaa ctg gtt gaa gat ttt cgg tgg atg aga tgt gat ata      432
Met Ser Ala Lys Leu Val Glu Asp Phe Arg Trp Met Arg Cys Asp Ile
    130                 135                 140
aaa act act tct tta att gcc aat ata tta ctg aat gat gag gct gta      480
Lys Thr Thr Ser Leu Ile Ala Asn Ile Leu Leu Asn Asp Glu Ala Val
145                 150                 155                 160
tct gca gga ttc cac act gca att ctt gcc cgg aac ggt cta att aca      528
Ser Ala Gly Phe His Thr Ala Ile Leu Ala Arg Asn Gly Leu Ile Thr
                165                 170                 175
gag gga agt agt acc aac gta ttt att gtc gca cag gat ggt gtt att      576

```
Glu Gly Ser Ser Thr Asn Val Phe Ile Val Ala Gln Asp Gly Val Ile
            180                 185                 190 aag aca cca ccc atg aat aat ttc tgt tta cca gga att act cgg caa      624
Lys Thr Pro Pro Met Asn Asn Phe Cys Leu Pro Gly Ile Thr Arg Gln
        195                 200                 205 gtt gtt att gaa ata att aaa aaa tta gat tta aag ttc aga gaa ata      672
Val Val Ile Glu Ile Ile Lys Lys Leu Asp Leu Lys Phe Arg Glu Ile
    210                 215                 220 gaa att agc att tca gag ctt ttt tct gct cag gaa gtt tgg ata aca      720
Glu Ile Ser Ile Ser Glu Leu Phe Ser Ala Gln Glu Val Trp Ile Thr
225                 230                 235                 240 agt acg aca aaa gaa gta ttc cct att aca aag att aat gac tct ttg      768
Ser Thr Thr Lys Glu Val Phe Pro Ile Thr Lys Ile Asn Asp Ser Leu
                245                 250                 255 att aat ggc gga aaa gtt ggc gaa tat tgg cgg ata att aat gat tcc      816
Ile Asn Gly Gly Lys Val Gly Glu Tyr Trp Arg Ile Ile Asn Asp Ser
            260                 265                 270 tac caa caa cta gta aac taa                                          837
Tyr Gln Gln Leu Val Asn
        275

<210> SEQ ID NO 21
<211> LENGTH: 278
<212> TYPE: PRT
<213> ORGANISM: Legionella pneumophila

<400> SEQUENCE: 21

Met Ser Ile Ala Phe Val Asn Gly Lys T

```
Ser Thr Thr Lys Glu Val Phe Pro Ile Thr Lys Ile Asn Asp Ser Leu
            245                 250                 255

Ile Asn Gly Gly Lys Val Gly Glu Tyr Trp Arg Ile Ile Asn Asp Ser
        260                 265                 270

Tyr Gln Gln Leu Val Asn
        275

<210> SEQ ID NO 22
<211> LENGTH: 861
<212> TYPE: DNA
<213> ORGANISM: Nitrosomonas europaea
<220> FEATURE:
<221> NAME/KEY: CDS
<222> LOCATION: (1)..(861)

<400> SEQUENCE: 22 atg att tac ctc aat ggc aaa ttt ctg ccg atg gaa cag gct acc gtt    48
Met Ile Tyr Leu Asn Gly Lys Phe Leu Pro Met Glu Gln Ala Thr Val
1               5                   10                  15 cca gtg ctg gat aga ggc ttc atc ttc ggt gat ggt gtc tat gaa gtc    96
Pro Val Leu Asp Arg Gly Phe Ile Phe Gly Asp Gly Val Tyr Glu Val
                20                  25                  30 ata ccg gtt tat tca cgt aaa ccg ttc cgg ctg ggc gaa cat ctt tcc   144
Ile Pro Val Tyr Ser Arg Lys Pro Phe Arg Leu Gly Glu His Leu Ser
            35                  40                  45 cgg ctg cag cac agt ctg gat ggc ata cgt ctc cag aat ccg cac act   192
Arg Leu Gln His Ser Leu Asp Gly Ile Arg Leu Gln Asn Pro His Thr
        50                  55                  60 gaa gaa caa tgg gct ggt ctg atc gaa cgc atc atc gag ctg aat gaa   240
Glu Glu Gln Trp Ala Gly Leu Ile Glu Arg Ile Ile Glu Leu Asn Glu
65                  70                  75                  80 ggt gat gat cag tac ctt tac ctg cac att aca cgc ggg gtg gca aaa   288
Gly Asp Asp Gln Tyr Leu Tyr Leu His Ile Thr Arg Gly Val Ala Lys
                85                  90                  95 cgt gac cat gcc ttt cct cgc gaa gta acg ccc act gtc ttc atc atg   336
Arg Asp His Ala Phe Pro Arg Glu Val Thr Pro Thr Val Phe Ile Met
            100                 105                 110 agc aac ccg ctt ccg gct cca cct gca aaa ttg ctc gtt tcc gga gtt   384
Ser Asn Pro Leu Pro Ala Pro Pro Ala Lys Leu Leu Val Ser Gly Val
        115                 120                 125 tca gcg att acc gcc agg gat aat cgc tgg ggg cgc tgt gat atc aaa   432
Ser Ala Ile Thr Ala Arg Asp Asn Arg Trp Gly Arg Cys Asp Ile Lys
    130                 135                 140 gcc att tca ctg ttg cca aat atc tta ttg cgc cag ctt gcc gtg gac   480
Ala Ile Ser Leu Leu Pro Asn Ile Leu Leu Arg Gln Leu Ala Val Asp
145                 150                 155                 160 gca caa gcc atg gaa acg atc ctg tta cgc gat ggt ctg ttg acc gaa   528
Ala Gln Ala Met Glu Thr Ile Leu Leu Arg Asp Gly Leu Leu Thr Glu
                165                 170                 175 ggg gcc gcc agc aat att ttc atc gta aaa gac gac ctg ctg ctg acc   576
Gly Ala Ala Ser Asn Ile Phe Ile Val Lys Asp Asp Leu Leu Leu Thr
            180                 185                 190 ccc ccc aaa gat cac cgt ata ttg cct ggc att act tat gat gta gta   624
Pro Pro Lys Asp His Arg Ile Leu Pro Gly Ile Thr Tyr Asp Val Val
        195                 200                 205 ctg gaa ctg gct gaa aca cat ggt gtt cca cat gcg aca aga gaa ata   672
Leu Glu Leu Ala Glu Thr His Gly Val Pro His Ala Thr Arg Glu Ile
    210                 215                 220 tca gag ctt gag tta cgt act gca cgg gaa atc atg ctg act tct tcc   720
Ser Glu Leu Glu Leu Arg Thr Ala Arg Glu Ile Met Leu Thr Ser Ser
225                 230                 235                 240
```

| | | |
|---|---|---|
| acc aaa gaa att ctc ccg atc aca cag ctg gat gga caa ccg atc ggt<br>Thr Lys Glu Ile Leu Pro Ile Thr Gln Leu Asp Gly Gln Pro Ile Gly<br>245 250 255 | | 768 |
| aat ggc acc cca ggg cca gta ttt cag caa ctg gat cgg ctc tat cag<br>Asn Gly Thr Pro Gly Pro Val Phe Gln Gln Leu Asp Arg Leu Tyr Gln<br>260 265 270 | | 816 |
| gca tat aag ctg gaa gtc atg cgc ggg cat gct cca cgc cag taa<br>Ala Tyr Lys Leu Glu Val Met Arg Gly His Ala Pro Arg Gln<br>275 280 285 | | 861 |

<210> SEQ ID NO 23
<211> LENGTH: 286
<212> TYPE: PRT
<213> ORGANISM: Nitrosomonas europaea

<400> SEQUENCE: 23

Met Ile Tyr Leu Asn Gly Lys Phe Leu Pro Met Glu Gln Ala Thr Val
1               5                   10                  15

Pro Val Leu Asp Arg Gly Phe Ile Phe Gly Asp Gly Val Tyr Glu Val
            20                  25                  30

Ile Pro Val Tyr Ser Arg Lys Pro Phe Arg Leu Gly Glu His Leu Ser
        35                  40                  45

Arg Leu Gln His Ser Leu Asp Gly Ile Arg Leu Gln Asn Pro His Thr
    50                  55                  60

Glu Glu Gln Trp Ala Gly Leu Ile Glu Arg Ile Glu Leu Asn Glu
65                  70                  75                  80

Gly Asp Asp Gln Tyr Leu Tyr Leu His Ile Thr Arg Gly Val Ala Lys
                85                  90                  95

Arg Asp His Ala Phe Pro Arg Glu Val Thr Pro Thr Val Phe Ile Met
            100                 105                 110

Ser Asn Pro Leu Pro Ala Pro Ala Lys Leu Leu Val Ser Gly Val
        115                 120                 125

Ser Ala Ile Thr Ala Arg Asp Asn Arg Trp Gly Arg Cys Asp Ile Lys
    130                 135                 140

Ala Ile Ser Leu Leu Pro Asn Ile Leu Leu Arg Gln Leu Ala Val Asp
145                 150                 155                 160

Ala Gln Ala Met Glu Thr Ile Leu Leu Arg Asp Gly Leu Leu Thr Glu
                165                 170                 175

Gly Ala Ala Ser Asn Ile Phe Ile Val Lys Asp Leu Leu Leu Thr
            180                 185                 190

Pro Pro Lys Asp His Arg Ile Leu Pro Gly Ile Thr Tyr Asp Val Val
        195                 200                 205

Leu Glu Leu Ala Glu Thr His Gly Val Pro His Ala Thr Arg Glu Ile
    210                 215                 220

Ser Glu Leu Glu Leu Arg Thr Ala Arg Glu Ile Met Leu Thr Ser Ser
225                 230                 235                 240

Thr Lys Glu Ile Leu Pro Ile Thr Gln Leu Asp Gly Gln Pro Ile Gly
                245                 250                 255

Asn Gly Thr Pro Gly Pro Val Phe Gln Gln Leu Asp Arg Leu Tyr Gln
            260                 265                 270

Ala Tyr Lys Leu Glu Val Met Arg Gly His Ala Pro Arg Gln
        275                 280                 285

<210> SEQ ID NO 24
<211> LENGTH: 1293
<212> TYPE: DNA
<213> ORGANISM: Neisseria gonorrhoeae
<220> FEATURE:

<221> NAME/KEY: CDS
<222> LOCATION: (1)..(1293)

<400> SEQUENCE: 24

| | | | | | | | | | | | | | | | | |
|---|---|---|---|---|---|---|---|---|---|---|---|---|---|---|---|---|
| atg | agg | ata | aat | atg | aac | cgt | aac | gaa | att | tta | ttc | gac | cgc | gcc | aag | 48 |
| Met | Arg | Ile | Asn | Met | Asn | Arg | Asn | Glu | Ile | Leu | Phe | Asp | Arg | Ala | Lys | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gcc | atc | atc | ccc | ggc | ggc | gtg | aat | tcg | ccc | gtg | cgc | gca | ttc | ggc | agc | 96 |
| Ala | Ile | Ile | Pro | Gly | Gly | Val | Asn | Ser | Pro | Val | Arg | Ala | Phe | Gly | Ser | |
| | | | 20 | | | | | 25 | | | | | 30 | | | |

| | | | | | | | | | | | | | | | | |
|---|---|---|---|---|---|---|---|---|---|---|---|---|---|---|---|---|
| gtc | ggc | ggc | gtg | ccg | cgc | ttc | atc | aaa | aaa | gcc | gaa | ggc | gcg | tat | gtt | 144 |
| Val | Gly | Gly | Val | Pro | Arg | Phe | Ile | Lys | Lys | Ala | Glu | Gly | Ala | Tyr | Val | |
| | | 35 | | | | | 40 | | | | | 45 | | | | |

| | | | | | | | | | | | | | | | | |
|---|---|---|---|---|---|---|---|---|---|---|---|---|---|---|---|---|
| tgg | gac | gaa | aac | ggc | acg | cgc | tac | acc | gat | tat | gtc | ggc | tct | tgg | ggg | 192 |
| Trp | Asp | Glu | Asn | Gly | Thr | Arg | Tyr | Thr | Asp | Tyr | Val | Gly | Ser | Trp | Gly | |
| | 50 | | | | | 55 | | | | | 60 | | | | | |

| | | | | | | | | | | | | | | | | |
|---|---|---|---|---|---|---|---|---|---|---|---|---|---|---|---|---|
| cct | gcg | att | gtc | gga | cac | gcg | cat | ccc | gaa | gtc | gtc | gaa | gcc | gtg | cgc | 240 |
| Pro | Ala | Ile | Val | Gly | His | Ala | His | Pro | Glu | Val | Val | Glu | Ala | Val | Arg | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gaa | gct | gcg | ttg | ggc | ggt | ttg | tcg | ttc | ggc | gcg | ccc | acc | gaa | ggc | gaa | 288 |
| Glu | Ala | Ala | Leu | Gly | Gly | Leu | Ser | Phe | Gly | Ala | Pro | Thr | Glu | Gly | Glu | |
| | | | | 85 | | | | | 90 | | | | | 95 | | |

| | | | | | | | | | | | | | | | | |
|---|---|---|---|---|---|---|---|---|---|---|---|---|---|---|---|---|
| atc | gcc | att | gcc | gaa | caa | att | gcc | gaa | att | atg | ccg | tct | gtc | gaa | cgg | 336 |
| Ile | Ala | Ile | Ala | Glu | Gln | Ile | Ala | Glu | Ile | Met | Pro | Ser | Val | Glu | Arg | |
| | | | 100 | | | | | 105 | | | | | 110 | | | |

| | | | | | | | | | | | | | | | | |
|---|---|---|---|---|---|---|---|---|---|---|---|---|---|---|---|---|
| ctg | cgc | ctc | gtc | agc | tcc | ggc | acg | gaa | gcg | acg | atg | act | gcc | atc | cgt | 384 |
| Leu | Arg | Leu | Val | Ser | Ser | Gly | Thr | Glu | Ala | Thr | Met | Thr | Ala | Ile | Arg | |
| | | 115 | | | | | 120 | | | | | 125 | | | | |

| | | | | | | | | | | | | | | | | |
|---|---|---|---|---|---|---|---|---|---|---|---|---|---|---|---|---|
| ctg | gca | cgc | ggt | ttt | acc | ggc | cgc | gac | aaa | atc | atc | aaa | ttt | gaa | ggc | 432 |
| Leu | Ala | Arg | Gly | Phe | Thr | Gly | Arg | Asp | Lys | Ile | Ile | Lys | Phe | Glu | Gly | |
| | 130 | | | | | 135 | | | | | 140 | | | | | |

| | | | | | | | | | | | | | | | | |
|---|---|---|---|---|---|---|---|---|---|---|---|---|---|---|---|---|
| tgc | tac | cac | ggc | cat | tcc | gac | agc | ctg | ttg | gtg | aaa | gca | ggc | agc | ggt | 480 |
| Cys | Tyr | His | Gly | His | Ser | Asp | Ser | Leu | Leu | Val | Lys | Ala | Gly | Ser | Gly | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ctg | ctt | acc | ttc | ggc | aat | cct | tct | tcc | gcc | ggt | gtg | cct | gcc | gac | ttt | 528 |
| Leu | Leu | Thr | Phe | Gly | Asn | Pro | Ser | Ser | Ala | Gly | Val | Pro | Ala | Asp | Phe | |
| | | | | 165 | | | | | 170 | | | | | 175 | | |

| | | | | | | | | | | | | | | | | |
|---|---|---|---|---|---|---|---|---|---|---|---|---|---|---|---|---|
| acc | aaa | cat | act | ttg | gta | ctc | gaa | tac | aac | aac | atc | gcc | caa | ctc | gaa | 576 |
| Thr | Lys | His | Thr | Leu | Val | Leu | Glu | Tyr | Asn | Asn | Ile | Ala | Gln | Leu | Glu | |
| | | | 180 | | | | | 185 | | | | | 190 | | | |

| | | | | | | | | | | | | | | | | |
|---|---|---|---|---|---|---|---|---|---|---|---|---|---|---|---|---|
| gaa | gcc | ttt | gcc | caa | agc | ggc | gac | gaa | atc | gcc | tgc | gtg | att | gtc | gaa | 624 |
| Glu | Ala | Phe | Ala | Gln | Ser | Gly | Asp | Glu | Ile | Ala | Cys | Val | Ile | Val | Glu | |
| | | 195 | | | | | 200 | | | | | 205 | | | | |

| | | | | | | | | | | | | | | | | |
|---|---|---|---|---|---|---|---|---|---|---|---|---|---|---|---|---|
| ccc | ttc | gtc | ggc | aat | atg | aac | ctc | gtc | cgc | ccg | acc | gaa | gcc | ttt | gtc | 672 |
| Pro | Phe | Val | Gly | Asn | Met | Asn | Leu | Val | Arg | Pro | Thr | Glu | Ala | Phe | Val | |
| | 210 | | | | | 215 | | | | | 220 | | | | | |

| | | | | | | | | | | | | | | | | |
|---|---|---|---|---|---|---|---|---|---|---|---|---|---|---|---|---|
| aaa | gcc | ttg | cgc | gga | ttg | acc | gaa | aaa | cac | ggc | gcg | gtg | ttg | att | tac | 720 |
| Lys | Ala | Leu | Arg | Gly | Leu | Thr | Glu | Lys | His | Gly | Ala | Val | Leu | Ile | Tyr | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gac | gaa | gtg | atg | acc | ggt | ttc | cgc | gtc | gcg | ctc | ggc | ggc | gcg | cag | tcg | 768 |
| Asp | Glu | Val | Met | Thr | Gly | Phe | Arg | Val | Ala | Leu | Gly | Gly | Ala | Gln | Ser | |
| | | | | 245 | | | | | 250 | | | | | 255 | | |

| | | | | | | | | | | | | | | | | |
|---|---|---|---|---|---|---|---|---|---|---|---|---|---|---|---|---|
| ctg | cac | ggc | atc | acg | ccc | gac | ctg | acc | acg | atg | ggc | aaa | gtc | atc | ggc | 816 |
| Leu | His | Gly | Ile | Thr | Pro | Asp | Leu | Thr | Thr | Met | Gly | Lys | Val | Ile | Gly | |
| | | | 260 | | | | | 265 | | | | | 270 | | | |

| | | | | | | | | | | | | | | | | |
|---|---|---|---|---|---|---|---|---|---|---|---|---|---|---|---|---|
| ggc | ggt | atg | ccg | ctt | gcc | gcg | ttc | ggc | gga | cgc | aaa | gac | atc | atg | gaa | 864 |
| Gly | Gly | Met | Pro | Leu | Ala | Ala | Phe | Gly | Gly | Arg | Lys | Asp | Ile | Met | Glu | |
| | | 275 | | | | | 280 | | | | | 285 | | | | |

| | | | | | | | | | | | | | | | | |
|---|---|---|---|---|---|---|---|---|---|---|---|---|---|---|---|---|
| tgt | att | tcc | ccg | ttg | ggc | ggc | gtg | tat | cag | gca | ggt | aca | tta | tca | ggc | 912 |
| Cys | Ile | Ser | Pro | Leu | Gly | Gly | Val | Tyr | Gln | Ala | Gly | Thr | Leu | Ser | Gly | |
| | 290 | | | | | 295 | | | | | 300 | | | | | |

```
aac ccg att gcc gtc gcc gcc ggc ttg aaa acg ctg gaa atc atc cag      960
Asn Pro Ile Ala Val Ala Ala Gly Leu Lys Thr Leu Glu Ile Ile Gln
305                 310                 315                 320 cgc gaa ggc ttc tat gaa aac ctg acc gcc ttg aca caa cgc ctt gcc     1008
Arg Glu Gly Phe Tyr Glu Asn Leu Thr Ala Leu Thr Gln Arg Leu Ala
                325                 330                 335 aac ggt att gcc gcc gcc aaa gcg cac ggt atc gag ttt gcc gcc gac     1056
Asn Gly Ile Ala Ala Ala Lys Ala His Gly Ile Glu Phe Ala Ala Asp
            340                 345                 350 agc gtg ggc ggt atg ttc ggt ctg tat ttc gcc gca cac gtg ccg cga     1104
Ser Val Gly Gly Met Phe Gly Leu Tyr Phe Ala Ala His Val Pro Arg
        355                 360                 365 aac tat gcc gat atg gcg cgc tcc aat atc gac gct ttc aaa cgc ttc     1152
Asn Tyr Ala Asp Met Ala Arg Ser Asn Ile Asp Ala Phe Lys Arg Phe
    370                 375                 380 ttc cac ggc atg ctc gac cgc ggc att gcc ttc ggc ccg tcc gct tat     1200
Phe His Gly Met Leu Asp Arg Gly Ile Ala Phe Gly Pro Ser Ala Tyr
385                 390                 395                 400 gaa gcg ggt ttc gtt tcc gcc gcg cat acg ccc gag ctg att gac gaa     1248
Glu Ala Gly Phe Val Ser Ala Ala His Thr Pro Glu Leu Ile Asp Glu
                405                 410                 415 acg gtt gcg gtt gcg gtt gaa gtg ttc aag gcg atg gct gca tga         1293
Thr Val Ala Val Ala Val Glu Val Phe Lys Ala Met Ala Ala
            420                 425                 430

<210> SEQ ID NO 25
<211> LENGTH: 430
<212> TYPE: PRT
<213> ORGANISM: Neisseria gonorrhoeae

<400> SEQUENCE: 25

Met Arg Ile Asn Met Asn Arg Asn Glu Ile Leu Phe Asp Arg Ala Lys
1               5                   10                  15

Ala Ile Ile Pro Gly Gly Val Asn Ser Pro Val Arg Ala Phe Gly Ser
            20                  25                  30

Val Gly Gly Val Pro Arg Phe Ile Lys Lys Ala Glu Gly Ala Tyr Val
        35                  40                  45

Trp Asp Glu Asn Gly Thr Arg Tyr Thr Asp Tyr Val Gly Ser Trp Gly
    50                  55                  60

Pro Ala Ile Val Gly His Ala His Pro Glu Val Glu Ala Val Arg
65                  70                  75                  80

Glu Ala Ala Leu Gly Gly Leu Ser Phe Gly Ala Pro Thr Glu Gly Glu
                85                  90                  95

Ile Ala Ile Ala Glu Gln Ile Ala Glu Ile Met Pro Ser Val Glu Arg
            100                 105                 110

Leu Arg Leu Val Ser Ser Gly Thr Glu Ala Thr Met Thr Ala Ile Arg
        115                 120                 125

Leu Ala Arg Gly Phe Thr Gly Arg Asp Lys Ile Ile Lys Phe Glu Gly
    130                 135                 140

Cys Tyr His Gly His Ser Asp Ser Leu Leu Val Lys Ala Gly Ser Gly
145                 150                 155                 160

Leu Leu Thr Phe Gly Asn Pro Ser Ser Ala Gly Val Pro Ala Asp Phe
                165                 170                 175

Thr Lys His Thr Leu Val Leu Glu Tyr Asn Asn Ile Ala Gln Leu Glu
            180                 185                 190

Glu Ala Phe Ala Gln Ser Gly Asp Glu Ile Ala Cys Val Ile Val Glu
        195                 200                 205
```

```
Pro Phe Val Gly Asn Met Asn Leu Val Arg Pro Thr Glu Ala Phe Val
    210                 215                 220

Lys Ala Leu Arg Gly Leu Thr Glu Lys His Gly Ala Val Leu Ile Tyr
225                 230                 235                 240

Asp Glu Val Met Thr Gly Phe Arg Val Ala Leu Gly Gly Ala Gln Ser
                245                 250                 255

Leu His Gly Ile Thr Pro Asp Leu Thr Thr Met Gly Lys Val Ile Gly
            260                 265                 270

Gly Gly Met Pro Leu Ala Ala Phe Gly Gly Arg Lys Asp Ile Met Glu
        275                 280                 285

Cys Ile Ser Pro Leu Gly Val Tyr Gln Ala Gly Thr Leu Ser Gly
290                 295                 300

Asn Pro Ile Ala Val Ala Ala Gly Leu Lys Thr Leu Glu Ile Ile Gln
305                 310                 315                 320

Arg Glu Gly Phe Tyr Glu Asn Leu Thr Ala Leu Thr Gln Arg Leu Ala
                325                 330                 335

Asn Gly Ile Ala Ala Ala Lys Ala His Gly Ile Glu Phe Ala Ala Asp
            340                 345                 350

Ser Val Gly Gly Met Phe Gly Leu Tyr Phe Ala Ala His Val Pro Arg
        355                 360                 365

Asn Tyr Ala Asp Met Ala Arg Ser Asn Ile Asp Ala Phe Lys Arg Phe
370                 375                 380

Phe His Gly Met Leu Asp Arg Gly Ile Ala Phe Gly Pro Ser Ala Tyr
385                 390                 395                 400

Glu Ala Gly Phe Val Ser Ala Ala His Thr Pro Glu Leu Ile Asp Glu
                405                 410                 415

Thr Val Ala Val Ala Val Glu Val Phe Lys Ala Met Ala Ala
            420                 425                 430

<210> SEQ ID NO 26
<211> LENGTH: 924
<212> TYPE: DNA
<213> ORGANISM: Pseudomonas aeruginosa
<220> FEATURE:
<221> NAME/KEY: CDS
<222> LOCATION: (1)..(924)

<400> SEQUENCE: 26 atg tcg atg gcc gat cgt gat ggc gtg atc tgg tat gac ggt gaa ctg      48
Met Ser Met Ala Asp Arg Asp Gly Val Ile Trp Tyr Asp Gly Glu Leu
1               5                   10                  15 gtg cag tgg cgc gac gcg acc acg cac gtg ctg acc cat acc ctg cac      96
Val Gln Trp Arg Asp Ala Thr Thr His Val Leu Thr His Thr Leu His
            20                  25                  30 tat gga atg ggc gtg ttc gag ggc gtg cgc gcc tac gac acc ccg cag     144
Tyr Gly Met Gly Val Phe Glu Gly Val Arg Ala Tyr Asp Thr Pro Gln
        35                  40                  45 ggc acg gcg atc ttc cgc ctg cag gcg cat acc gac cgg ctg ttc gac     192
Gly Thr Ala Ile Phe Arg Leu Gln Ala His Thr Asp Arg Leu Phe Asp
    50                  55                  60 tcc gcg cac atc atg aac atg cag atc ccg tac agc cgc gac gag atc     240
Ser Ala His Ile Met Asn Met Gln Ile Pro Tyr Ser Arg Asp Glu Ile
65                  70                  75                  80 aac gag gcg acc cgc gcc gcc gtg cgc gag aac aac ctg gaa agc gcc     288
Asn Glu Ala Thr Arg Ala Ala Val Arg Glu Asn Asn Leu Glu Ser Ala
                85                  90                  95 tat atc cgc ccg atg gtg ttc tac gga agc gaa ggc atg ggc ctg cgc     336
Tyr Ile Arg Pro Met Val Phe Tyr Gly Ser Glu Gly Met Gly Leu Arg
            100                 105                 110
```

| | | |
|---|---|---|
| gcc agc ggc ctg aag gtc cat gtg atc atc gcc gcc tgg agc tgg ggc<br>Ala Ser Gly Leu Lys Val His Val Ile Ile Ala Ala Trp Ser Trp Gly<br>115                             120                    125 | | 384 |
| gcc tac atg ggc gag gaa gcc ctg cag caa ggc atc aag gtg cgc acc<br>Ala Tyr Met Gly Glu Glu Ala Leu Gln Gln Gly Ile Lys Val Arg Thr<br>        130                       135                    140 | | 432 |
| agt tcc ttc acc cgc cac cac gtc aac atc tcg atg acc cgc gcc aag<br>Ser Ser Phe Thr Arg His His Val Asn Ile Ser Met Thr Arg Ala Lys<br>145                         150                    155                    160 | | 480 |
| tcc aac ggc gcc tac atc aac tcg atg ctg gcc ctc cag gaa gcg atc<br>Ser Asn Gly Ala Tyr Ile Asn Ser Met Leu Ala Leu Gln Glu Ala Ile<br>                  165                    170                    175 | | 528 |
| tcc ggc ggc gcc gac gag gcc atg atg ctc gat ccg gaa ggc tac gtg<br>Ser Gly Gly Ala Asp Glu Ala Met Met Leu Asp Pro Glu Gly Tyr Val<br>                     180                    185                    190 | | 576 |
| gcc gaa ggc tcc ggc gag aac atc ttc atc atc aag gat ggc gtg atc<br>Ala Glu Gly Ser Gly Glu Asn Ile Phe Ile Ile Lys Asp Gly Val Ile<br>                195                    200                    205 | | 624 |
| tac acc ccg gaa gtc acc gcc tgc ctg aac ggc atc act cgt aac act<br>Tyr Thr Pro Glu Val Thr Ala Cys Leu Asn Gly Ile Thr Arg Asn Thr<br>210                           215                    220 | | 672 |
| atc ctg acc ctg gcc gcc gaa cac ggt ttt aaa ctg gtc gag aag cgc<br>Ile Leu Thr Leu Ala Ala Glu His Gly Phe Lys Leu Val Glu Lys Arg<br>225                         230                    235                    240 | | 720 |
| atc acc cgc gac gag gtg tac atc gcc gac gag gcc ttc ttc act ggc<br>Ile Thr Arg Asp Glu Val Tyr Ile Ala Asp Glu Ala Phe Phe Thr Gly<br>                     245                    250                    255 | | 768 |
| act gcc gcg gaa gtc acg ccg atc cgc gaa gtg gac ggt cgc aag atc<br>Thr Ala Ala Glu Val Thr Pro Ile Arg Glu Val Asp Gly Arg Lys Ile<br>                  260                    265                    270 | | 816 |
| ggc gcc ggc cgc cgt ggc ccg gtc acc gaa aag ctg cag aaa gcc tat<br>Gly Ala Gly Arg Arg Gly Pro Val Thr Glu Lys Leu Gln Lys Ala Tyr<br>275                         280                    285 | | 864 |
| ttc gac ctg gtc agc ggc aag acc gag gcc cac gcc gag tgg cgt acc<br>Phe Asp Leu Val Ser Gly Lys Thr Glu Ala His Ala Glu Trp Arg Thr<br>290                         295                    300 | | 912 |
| ctg gtc aag taa<br>Leu Val Lys<br>305 | | 924 |

<210> SEQ ID NO 27
<211> LENGTH: 307
<212> TYPE: PRT
<213> ORGANISM: Pseudomonas aeruginosa

<400> SEQUENCE: 27

Met Ser Met Ala Asp Arg Asp Gly Val Ile Trp Tyr Asp Gly Glu Leu
1                  5                      10                    15

Val Gln Trp Arg Asp Ala Thr Thr His Val Leu Thr His Thr Leu His
                  20                    25                    30

Tyr Gly Met Gly Val Phe Glu Gly Val Arg Ala Tyr Asp Thr Pro Gln
            35                    40                    45

Gly Thr Ala Ile Phe Arg Leu Gln Ala His Thr Asp Arg Leu Phe Asp
    50                    55                    60

Ser Ala His Ile Met Asn Met Gln Ile Pro Tyr Ser Arg Asp Glu Ile
65                    70                    75                    80

Asn Glu Ala Thr Arg Ala Ala Val Arg Glu Asn Asn Leu Glu Ser Ala
                  85                    90                    95

Tyr Ile Arg Pro Met Val Phe Tyr Gly Ser Glu Gly Met Gly Leu Arg

```
            100                 105                 110
Ala Ser Gly Leu Lys Val His Val Ile Ile Ala Ala Trp Ser Trp Gly
        115                 120                 125

Ala Tyr Met Gly Glu Glu Ala Leu Gln Gln Gly Ile Lys Val Arg Thr
    130                 135                 140

Ser Ser Phe Thr Arg His His Val Asn Ile Ser Met Thr Arg Ala Lys
145                 150                 155                 160

Ser Asn Gly Ala Tyr Ile Asn Ser Met Leu Ala Leu Gln Glu Ala Ile
                165                 170                 175

Ser Gly Gly Ala Asp Glu Ala Met Met Leu Asp Pro Glu Gly Tyr Val
            180                 185                 190

Ala Glu Gly Ser Gly Glu Asn Ile Phe Ile Ile Lys Asp Gly Val Ile
        195                 200                 205

Tyr Thr Pro Glu Val Thr Ala Cys Leu Asn Gly Ile Thr Arg Asn Thr
    210                 215                 220

Ile Leu Thr Leu Ala Ala Glu His Gly Phe Lys Leu Val Glu Lys Arg
225                 230                 235                 240

Ile Thr Arg Asp Glu Val Tyr Ile Ala Asp Glu Ala Phe Phe Thr Gly
                245                 250                 255

Thr Ala Ala Glu Val Thr Pro Ile Arg Glu Val Asp Gly Arg Lys Ile
            260                 265                 270

Gly Ala Gly Arg Arg Gly Pro Val Thr Glu Lys Leu Gln Lys Ala Tyr
        275                 280                 285

Phe Asp Leu Val Ser Gly Lys Thr Glu Ala His Ala Glu Trp Arg Thr
    290                 295                 300

Leu Val Lys
305

<210> SEQ ID NO 28
<211> LENGTH: 1407
<212> TYPE: DNA
<213> ORGANISM: Rhodopseudomonas palustris
<220> FEATURE:
<221> NAME/KEY: CDS
<222> LOCATION: (1)..(1407)

<400> SEQUENCE: 28 atg aag ctg ata ccg tgc cgc gcc ttt cac ccc ccg gcc gcg cag tgc       48
Met Lys Leu Ile Pro Cys Arg Ala Phe His Pro Pro Ala Ala Gln Cys
1               5                   10                  15 atg agg agc gcc atg tta gac aag atc aag ccc acg tcc gcc gtc aac       96
Met Arg Ser Ala Met Leu Asp Lys Ile Lys Pro Thr Ser Ala Val Asn
                20                  25                  30 gcg ccg aac gat ctc aac gcg ttc tgg atg ccg ttc acc gcg aac cgg      144
Ala Pro Asn Asp Leu Asn Ala Phe Trp Met Pro Phe Thr Ala Asn Arg
            35                  40                  45 gcc ttc aag cgc gcg ccg aag atg gtc gtg ggt gcc gaa ggc atg cac      192
Ala Phe Lys Arg Ala Pro Lys Met Val Val Gly Ala Glu Gly Met His
        50                  55                  60 tac atc acc gcc gat ggt cgc aag atc atc gac gcc gcc tcg ggc atg      240
Tyr Ile Thr Ala Asp Gly Arg Lys Ile Ile Asp Ala Ala Ser Gly Met
65                  70                  75                  80 tgg tgc acc aat gcg ggc cat ggc cgc aag gaa atc gcc gag gcg atc      288
Trp Cys Thr Asn Ala Gly His Gly Arg Lys Glu Ile Ala Glu Ala Ile
                85                  90                  95 aag gcg cag gcc gat gaa ctc gac ttc tcg ccg ccg ttc cag ttc ggc      336
Lys Ala Gln Ala Asp Glu Leu Asp Phe Ser Pro Pro Phe Gln Phe Gly
            100                 105                 110
```

```
cag ccg aag gcg ttc gaa ctc gcc agc cgg atc gcc gat ctg gcg ccg      384
Gln Pro Lys Ala Phe Glu Leu Ala Ser Arg Ile Ala Asp Leu Ala Pro
    115                 120                 125 gaa ggc ctc gat cac gtg ttc ttc tgc aat tcg ggc tcg gaa gcc ggc      432
Glu Gly Leu Asp His Val Phe Phe Cys Asn Ser Gly Ser Glu Ala Gly
130                 135                 140 gac acc gcg ctg aag atc gcg gtc gcc tat cag cag atc aag ggc cag      480
Asp Thr Ala Leu Lys Ile Ala Val Ala Tyr Gln Gln Ile Lys Gly Gln
145                 150                 155                 160 ggc tca cgc acc cgg ctg atc ggc cgc gag cgc ggc tat cac ggc gtc      528
Gly Ser Arg Thr Arg Leu Ile Gly Arg Glu Arg Gly Tyr His Gly Val
                165                 170                 175 ggc ttc ggc ggc acc gcg gtc ggc ggc atc ggc aac aac cgc aag atg      576
Gly Phe Gly Gly Thr Ala Val Gly Gly Ile Gly Asn Asn Arg Lys Met
            180                 185                 190 ttc ggt ccg ctg ctc aac ggc gtc gat cat ctg cct gcg act tat gat      624
Phe Gly Pro Leu Leu Asn Gly Val Asp His Leu Pro Ala Thr Tyr Asp
        195                 200                 205 cgc gac aag cag gct ttc acc atc ggc gag ccg gaa tac ggc gcg cac      672
Arg Asp Lys Gln Ala Phe Thr Ile Gly Glu Pro Glu Tyr Gly Ala His
    210                 215                 220 ttc gcc gaa gcg ctt gaa ggc ctc gtc aat ctg cac ggc gcc aac acc      720
Phe Ala Glu Ala Leu Glu Gly Leu Val Asn Leu His Gly Ala Asn Thr
225                 230                 235                 240 atc gcg gcg gtg atc gtc gag ccg atg gcc ggc tcc acc ggc gtg ctg      768
Ile Ala Ala Val Ile Val Glu Pro Met Ala Gly Ser Thr Gly Val Leu
                245                 250                 255 ccg gcg ccg aag ggc tat ctc aag aag ctg cgc gag atc acc aag aag      816
Pro Ala Pro Lys Gly Tyr Leu Lys Lys Leu Arg Glu Ile Thr Lys Lys
            260                 265                 270 cac ggc atc ctg ctg atc ttc gac gag gtc atc acc ggc tac ggc cgt      864
His Gly Ile Leu Leu Ile Phe Asp Glu Val Ile Thr Gly Tyr Gly Arg
        275                 280                 285 ctc ggc tat gcc ttc gcg tcc gaa cgt tac ggc gtc acc ccg gac atg      912
Leu Gly Tyr Ala Phe Ala Ser Glu Arg Tyr Gly Val Thr Pro Asp Met
    290                 295                 300 atc acc ttc gcc aag ggc gtc acc aat ggt gcg gtg ccg atg ggc ggc      960
Ile Thr Phe Ala Lys Gly Val Thr Asn Gly Ala Val Pro Met Gly Gly
305                 310                 315                 320 gtg atc acc tcg gcg gag atc cac gat gcg ttc atg acc ggc ccc gag     1008
Val Ile Thr Ser Ala Glu Ile His Asp Ala Phe Met Thr Gly Pro Glu
                325                 330                 335 cac gcg gtc gag ctg gcg cac ggc tac acc tat tcg gcg cat ccg ctc     1056
His Ala Val Glu Leu Ala His Gly Tyr Thr Tyr Ser Ala His Pro Leu
            340                 345                 350 gcc tgc gcg gcc ggc atc gcc acc ctc gac atc tac cgc gac gag aag     1104
Ala Cys Ala Ala Gly Ile Ala Thr Leu Asp Ile Tyr Arg Asp Glu Lys
        355                 360                 365 ctg ttc gag cgc gcc aag gcg ctg gag ccg aag ttt gcc gag gcg gtg     1152
Leu Phe Glu Arg Ala Lys Ala Leu Glu Pro Lys Phe Ala Glu Ala Val
    370                 375                 380 atg tcg ctg aag tcg gcc ccg aac gtg gtc gac atc cgc acc gtc ggc     1200
Met Ser Leu Lys Ser Ala Pro Asn Val Val Asp Ile Arg Thr Val Gly
385                 390                 395                 400 ctg acg gcg ggt atc gac ctc gct tcg atc gcc gat gcg gtc ggc aag     1248
Leu Thr Ala Gly Ile Asp Leu Ala Ser Ile Ala Asp Ala Val Gly Lys
                405                 410                 415 cgt ggc ttc gaa gcg atg aat gcc ggc ttc cac gac cac gag ctg atg     1296
Arg Gly Phe Glu Ala Met Asn Ala Gly Phe His Asp His Glu Leu Met
            420                 425                 430
```

```
ctg cgg atc gcc ggc gac acc ctg gcg ctg acc ccg ccg ctg atc ctc    1344
Leu Arg Ile Ala Gly Asp Thr Leu Ala Leu Thr Pro Pro Leu Ile Leu
    435                 440                 445 agc gag gac cac atc ggt gag atc gtc gac aag gtc ggc aag gtg atc    1392
Ser Glu Asp His Ile Gly Glu Ile Val Asp Lys Val Gly Lys Val Ile
450                 455                 460 cgc gcg gtc gcc tga                                                1407
Arg Ala Val Ala
465

<210> SEQ ID NO 29
<211> LENGTH: 468
<212> TYPE: PRT
<213> ORGANISM: Rhodopseudomonas palustris

<400> SEQUENCE: 29

Met Lys Leu Ile Pro Cys Arg Ala Phe His Pro Ala Ala Gln Cys
1               5                   10                  15

Met Arg Ser Ala Met Leu Asp Lys Ile Lys Pro Thr Ser Ala Val Asn
            20                  25                  30

Ala Pro Asn Asp Leu Asn Ala Phe Trp Met Pro Phe Thr Ala Asn Arg
        35                  40                  45

Ala Phe Lys Arg Ala Pro Lys Met Val Val Gly Ala Glu Gly Met His
    50                  55                  60

Tyr Ile Thr Ala Asp Gly Arg Lys Ile Ile Asp Ala Ala Ser Gly Met
65                  70                  75                  80

Trp Cys Thr Asn Ala Gly His Gly Arg Lys Glu Ile Ala Glu Ala Ile
                85                  90                  95

Lys Ala Gln Ala Asp Glu Leu Asp Phe Ser Pro Pro Phe Gln Phe Gly
            100                 105                 110

Gln Pro Lys Ala Phe Glu Leu Ala Ser Arg Ile Ala Asp Leu Ala Pro
        115                 120                 125

Glu Gly Leu Asp His Val Phe Phe Cys Asn Ser Gly Ser Glu Ala Gly
    130                 135                 140

Asp Thr Ala Leu Lys Ile Ala Val Ala Tyr Gln Gln Ile Lys Gly Gln
145                 150                 155                 160

Gly Ser Arg Thr Arg Leu Ile Gly Arg Glu Arg Gly Tyr His Gly Val
                165                 170                 175

Gly Phe Gly Gly Thr Ala Val Gly Gly Ile Gly Asn Asn Arg Lys Met
            180                 185                 190

Phe Gly Pro Leu Leu Asn Gly Val Asp His Leu Pro Ala Thr Tyr Asp
        195                 200                 205

Arg Asp Lys Gln Ala Phe Thr Ile Gly Glu Pro Glu Tyr Gly Ala His
    210                 215                 220

Phe Ala Glu Ala Leu Glu Gly Leu Val Asn Leu His Gly Ala Asn Thr
225                 230                 235                 240

Ile Ala Ala Val Ile Val Glu Pro Met Ala Gly Ser Thr Gly Val Leu
                245                 250                 255

Pro Ala Pro Lys Gly Tyr Leu Lys Lys Leu Arg Glu Ile Thr Lys Lys
            260                 265                 270

His Gly Ile Leu Leu Ile Phe Asp Glu Val Ile Thr Gly Tyr Gly Arg
        275                 280                 285

Leu Gly Tyr Ala Phe Ala Ser Glu Arg Tyr Gly Val Thr Pro Asp Met
    290                 295                 300

Ile Thr Phe Ala Lys Gly Val Thr Asn Gly Ala Val Pro Met Gly Gly
305                 310                 315                 320
```

```
Val Ile Thr Ser Ala Glu Ile His Asp Ala Phe Met Thr Gly Pro Glu
            325                 330                 335

His Ala Val Glu Leu Ala His Gly Tyr Thr Tyr Ser Ala His Pro Leu
            340                 345                 350

Ala Cys Ala Ala Gly Ile Ala Thr Leu Asp Ile Tyr Arg Asp Glu Lys
            355                 360                 365

Leu Phe Glu Arg Ala Lys Ala Leu Glu Pro Lys Phe Ala Glu Ala Val
            370                 375                 380

Met Ser Leu Lys Ser Ala Pro Asn Val Val Asp Ile Arg Thr Val Gly
385                 390                 395                 400

Leu Thr Ala Gly Ile Asp Leu Ala Ser Ile Ala Asp Ala Val Gly Lys
                405                 410                 415

Arg Gly Phe Glu Ala Met Asn Ala Gly Phe His Asp His Glu Leu Met
            420                 425                 430

Leu Arg Ile Ala Gly Asp Thr Leu Ala Leu Thr Pro Pro Leu Ile Leu
            435                 440                 445

Ser Glu Asp His Ile Gly Glu Ile Val Asp Lys Val Gly Lys Val Ile
            450                 455                 460

Arg Ala Val Ala
465

<210> SEQ ID NO 30
<211> LENGTH: 1263
<212> TYPE: DNA
<213> ORGANISM: Escherichia coli
<220> FEATURE:
<221> NAME/KEY: CDS
<222> LOCATION: (1)..(1263)

<400> SEQUENCE: 30 atg cca cat tca ctg ttc agc acc gat acc gat ctc acc gcc gaa aat      48
Met Pro His Ser Leu Phe Ser Thr Asp Thr Asp Leu Thr Ala Glu Asn
1               5                   10                  15 ctg ctg cgt ttg ccc gct gaa ttt ggc tgc ccg gtg tgg gtc tac gat      96
Leu Leu Arg Leu Pro Ala Glu Phe Gly Cys Pro Val Trp Val Tyr Asp
                20                  25                  30 gcg caa att att cgt cgg cag att gca gcg ctg aaa cag ttt gat gtg     144
Ala Gln Ile Ile Arg Arg Gln Ile Ala Ala Leu Lys Gln Phe Asp Val
            35                  40                  45 gtg cgc ttt gca cag aaa gcc tgt tcc aat att cat att ttg cgc tta     192
Val Arg Phe Ala Gln Lys Ala Cys Ser Asn Ile His Ile Leu Arg Leu
        50                  55                  60 atg cgt gag cag ggc gtg aaa gtg gat tcc gtc tcg tta ggc gaa ata     240
Met Arg Glu Gln Gly Val Lys Val Asp Ser Val Ser Leu Gly Glu Ile
65                  70                  75                  80 gag cgt gcg ttg gcg gcg ggt tac aat ccg caa acg cac ccc gat gat     288
Glu Arg Ala Leu Ala Ala Gly Tyr Asn Pro Gln Thr His Pro Asp Asp
                85                  90                  95 att gtt ttt acg gca gat gtt atc gat cag gcg acg ctt gaa cgc gtc     336
Ile Val Phe Thr Ala Asp Val Ile Asp Gln Ala Thr Leu Glu Arg Val
            100                 105                 110 agt gaa ttg caa att ccg gtg aat gcg ggt tct gtt gat atg ctc gac     384
Ser Glu Leu Gln Ile Pro Val Asn Ala Gly Ser Val Asp Met Leu Asp
        115                 120                 125 caa ctg ggc cag gtt tcg cca ggg cat cgg gta tgg ctg cgc gtt aat     432
Gln Leu Gly Gln Val Ser Pro Gly His Arg Val Trp Leu Arg Val Asn
    130                 135                 140 ccg ggg ttt ggt cac gga cat agc caa aaa acc aat acc ggt ggc gaa     480
Pro Gly Phe Gly His Gly His Ser Gln Lys Thr Asn Thr Gly Gly Glu
145                 150                 155                 160
```

```
aac agc aag cac ggt atc tgg tac acc gat ctg ccc gcc gca ctg gac        528
Asn Ser Lys His Gly Ile Trp Tyr Thr Asp Leu Pro Ala Ala Leu Asp
            165                 170                 175 gtg ata caa cgt cat cat ctg cag ctg gtc ggc att cac atg cac att        576
Val Ile Gln Arg His His Leu Gln Leu Val Gly Ile His Met His Ile
    180                 185                 190 ggt tct ggc gtt gat tat gcc cat ctg gaa cag gtg tgt ggt gct atg        624
Gly Ser Gly Val Asp Tyr Ala His Leu Glu Gln Val Cys Gly Ala Met
195                 200                 205 gtg cgt cag gtc atc gaa ttc ggt cag gat tta cag gct att tct gcg        672
Val Arg Gln Val Ile Glu Phe Gly Gln Asp Leu Gln Ala Ile Ser Ala
    210                 215                 220 ggc ggt ggg ctt tct gtt cct tat caa cag ggt gaa gag gcg gtt gat        720
Gly Gly Gly Leu Ser Val Pro Tyr Gln Gln Gly Glu Glu Ala Val Asp
225                 230                 235                 240 acc gaa cat tat tat ggt ctg tgg aat gcc gcg cgt gag caa atc gcc        768
Thr Glu His Tyr Tyr Gly Leu Trp Asn Ala Ala Arg Glu Gln Ile Ala
                245                 250                 255 cgc cat ttg ggc cac cct gtg aaa ctg gaa att gaa ccg ggt cgc ttc        816
Arg His Leu Gly His Pro Val Lys Leu Glu Ile Glu Pro Gly Arg Phe
            260                 265                 270 ctg gta gcg cag tct ggc gta tta att act cag gtg cgg agc gtc aaa        864
Leu Val Ala Gln Ser Gly Val Leu Ile Thr Gln Val Arg Ser Val Lys
        275                 280                 285 caa atg ggg agc cgc cac ttt gtg ctg gtt gat gcc ggg ttc aac gat        912
Gln Met Gly Ser Arg His Phe Val Leu Val Asp Ala Gly Phe Asn Asp
    290                 295                 300 ctg atg cgc ccg gca atg tac ggt agt tac cac cat atc agt gcc ctg        960
Leu Met Arg Pro Ala Met Tyr Gly Ser Tyr His His Ile Ser Ala Leu
305                 310                 315                 320 gca gct gat ggt cgt tct ctg gaa cac gcg cca acg gtg gaa acc gtc       1008
Ala Ala Asp Gly Arg Ser Leu Glu His Ala Pro Thr Val Glu Thr Val
                325                 330                 335 gtc gcc gga ccg tta tgt gaa tcg ggc gat gtc ttt acc cag cag gaa       1056
Val Ala Gly Pro Leu Cys Glu Ser Gly Asp Val Phe Thr Gln Gln Glu
            340                 345                 350 ggg gga aat gtt gaa acc cgc gcc ttg ccg gaa gtg aag gca ggt gat       1104
Gly Gly Asn Val Glu Thr Arg Ala Leu Pro Glu Val Lys Ala Gly Asp
        355                 360                 365 tat ctg gta ctg cat gat aca ggg gca tat ggc gca tca atg tca tcc       1152
Tyr Leu Val Leu His Asp Thr Gly Ala Tyr Gly Ala Ser Met Ser Ser
    370                 375                 380 aac tac aat agc cgt ccg ctg tta cca gaa gtt ctg ttt gat aat ggt       1200
Asn Tyr Asn Ser Arg Pro Leu Leu Pro Glu Val Leu Phe Asp Asn Gly
385                 390                 395                 400 cag gcg cgg ttg att cgc cgt cgc cag acc atc gaa gaa tta ctg gcg       1248
Gln Ala Arg Leu Ile Arg Arg Arg Gln Thr Ile Glu Glu Leu Leu Ala
                405                 410                 415 ctg gaa ttg ctt taa                                                   1263
Leu Glu Leu Leu
            420

<210> SEQ ID NO 31
<211> LENGTH: 420
<212> TYPE: PRT
<213> ORGANISM: Escherichia coli

<400> SEQUENCE: 31

Met Pro His Ser Leu Phe Ser Thr Asp Thr Asp Leu Thr Ala Glu Asn
1               5                   10                  15
```

```
Leu Leu Arg Leu Pro Ala Glu Phe Gly Cys Pro Val Trp Val Tyr Asp
         20                  25                  30

Ala Gln Ile Ile Arg Arg Gln Ile Ala Ala Leu Lys Gln Phe Asp Val
             35                  40                  45

Val Arg Phe Ala Gln Lys Ala Cys Ser Asn Ile His Ile Leu Arg Leu
 50                  55                  60

Met Arg Glu Gln Gly Val Lys Val Asp Ser Val Ser Leu Gly Glu Ile
 65                  70                  75                  80

Glu Arg Ala Leu Ala Ala Gly Tyr Asn Pro Gln Thr His Pro Asp Asp
                 85                  90                  95

Ile Val Phe Thr Ala Asp Val Ile Asp Gln Ala Thr Leu Glu Arg Val
            100                 105                 110

Ser Glu Leu Gln Ile Pro Val Asn Ala Gly Ser Val Asp Met Leu Asp
            115                 120                 125

Gln Leu Gly Gln Val Ser Pro Gly His Arg Val Trp Leu Arg Val Asn
130                 135                 140

Pro Gly Phe Gly His Gly His Ser Gln Lys Thr Asn Thr Gly Gly Glu
145                 150                 155                 160

Asn Ser Lys His Gly Ile Trp Tyr Thr Asp Leu Pro Ala Ala Leu Asp
                165                 170                 175

Val Ile Gln Arg His Leu Gln Leu Val Gly Ile His Met His Ile
            180                 185                 190

Gly Ser Gly Val Asp Tyr Ala His Leu Glu Gln Val Cys Gly Ala Met
        195                 200                 205

Val Arg Gln Val Ile Glu Phe Gly Gln Asp Leu Gln Ala Ile Ser Ala
    210                 215                 220

Gly Gly Gly Leu Ser Val Pro Tyr Gln Gln Gly Glu Glu Ala Val Asp
225                 230                 235                 240

Thr Glu His Tyr Tyr Gly Leu Trp Asn Ala Ala Arg Glu Gln Ile Ala
                245                 250                 255

Arg His Leu Gly His Pro Val Lys Leu Glu Ile Glu Pro Gly Arg Phe
            260                 265                 270

Leu Val Ala Gln Ser Gly Val Leu Ile Thr Gln Val Arg Ser Val Lys
        275                 280                 285

Gln Met Gly Ser Arg His Phe Val Leu Val Asp Ala Gly Phe Asn Asp
    290                 295                 300

Leu Met Arg Pro Ala Met Tyr Gly Ser Tyr His His Ile Ser Ala Leu
305                 310                 315                 320

Ala Ala Asp Gly Arg Ser Leu Glu His Ala Pro Thr Val Glu Thr Val
                325                 330                 335

Val Ala Gly Pro Leu Cys Glu Ser Gly Asp Val Phe Thr Gln Gln Glu
            340                 345                 350

Gly Gly Asn Val Glu Thr Arg Ala Leu Pro Glu Val Lys Ala Gly Asp
        355                 360                 365

Tyr Leu Val Leu His Asp Thr Gly Ala Tyr Gly Ala Ser Met Ser Ser
    370                 375                 380

Asn Tyr Asn Ser Arg Pro Leu Leu Pro Glu Val Leu Phe Asp Asn Gly
385                 390                 395                 400

Gln Ala Arg Leu Ile Arg Arg Gln Thr Ile Glu Glu Leu Leu Ala
                405                 410                 415

Leu Glu Leu Leu
        420

<210> SEQ ID NO 32
```

<211> LENGTH: 1265
<212> TYPE: DNA
<213> ORGANISM: Artificial
<220> FEATURE:
<223> OTHER INFORMATION: Escherichia.coli diaminopimelate decarboxylase
      LysA codon optimised gene

<400> SEQUENCE: 32

```
atatgccaca ctctctgttt tctactgata ctgatctgac tgcggaaaac ctgctgcgtc     60
tgccggctga attcggttgt ccggtatggg tgtacgacgc tcagattatt cgtcgccaga    120
tcgcagcact gaagcagttc gatgtagtgc gttttgcaca gaaggcgtgc tccaacatcc    180
atatcctgcg cctgatgcgt gagcagggcg ttaaagttga ctccgtctct ctgggtgaga    240
ttgagcgcgc cctggcagcc ggctataacc cacagaccca tcctgacgac attgtattta    300
ctgccgacgt gatcgaccag gctactctgg aacgcgtttc tgaactgcag atcccggtta    360
atgctggttc tgtggacatg ctggaccagc tgggccaggt atcccaggt catcgtgtgt     420
ggctgcgtgt caacccaggt ttcggccacg ccactctca gaaaactaac actggtggtg     480
agaactccaa gcatggcatt tggtataccg atctgccggc tgcactggac gtaatccagc    540
gtcaccacct gcagctggtg ggcatccaca tgcacattgg ctccggcgta gactacgccc    600
acctggagca agtctgcggt gctatggtac gtcaggtaat cgagttcggc caagatctgc    660
aggcaatcag cgctggtggc ggcctgtctg taccttatca gcagggcgag gaggcggttg    720
acactgagca ctactacggt ctgtggaacg ccgctcgtga gcaaattgca cgtcacctgg    780
gccacccggt gaaactggag atcgagccgg gccgcttcct ggtagcacag tccggcgtac    840
tgattaccca ggtacgctct gttaaacaga tgggctcccg tcactttgtg ctggtagacg    900
caggcttcaa cgacctgatg cgtccggcta tgtatggttc ctatcatcac atctctgcgc    960
tggccgccga cggccgctct ctggaacacg cgccgacggt tgaaacggtg gtggctggtc   1020
cgctgtgcga gtccggcgac gttttcactc agcaggaggg cggcaatgta gagacgcgtg   1080
cgctgccgga agtgaaagcc ggtgattatc tggtgctgca tgataccggc gcctatggtg   1140
cgagcatgag cagcaactac aactctcgcc cgctgctgcc ggaggtcctg ttcgataacg   1200
gccaagcccg cctgatccgt cgtcgtcaga ccatcgagga actgctggca ctggagctgc   1260
tgtaa                                                               1265
```

<210> SEQ ID NO 33
<211> LENGTH: 1692
<212> TYPE: DNA
<213> ORGANISM: Saccharomyces cerevisiae
<220> FEATURE:
<221> NAME/KEY: CDS
<222> LOCATION: (1)..(1692)

<400> SEQUENCE: 33

```
atg tct gaa att act ttg ggt aaa tat ttg ttc gaa aga tta aag caa      48
Met Ser Glu Ile Thr Leu Gly Lys Tyr Leu Phe Glu Arg Leu Lys Gln
1               5                   10                  15 gtc aac gtt aac acc gtt ttc ggt ttg cca ggt gac ttc aac ttg tcc      96
Val Asn Val Asn Thr Val Phe Gly Leu Pro Gly Asp Phe Asn Leu Ser
            20                  25                  30 ttg ttg gac aag atc tac gaa gtt gaa ggt atg aga tgg gct ggt aac     144
Leu Leu Asp Lys Ile Tyr Glu Val Glu Gly Met Arg Trp Ala Gly Asn
        35                  40                  45 gcc aac gaa ttg aac gct gct tac gcc gct gat ggt tac gct cgt atc     192
Ala Asn Glu Leu Asn Ala Ala Tyr Ala Ala Asp Gly Tyr Ala Arg Ile
    50                  55                  60
```

```
aag ggt atg tct tgt atc atc acc acc ttc ggt gtc ggt gaa ttg tct        240
Lys Gly Met Ser Cys Ile Ile Thr Thr Phe Gly Val Gly Glu Leu Ser
 65              70                  75                  80 gct ttg aac ggt att gcc ggt tct tac gct gaa cac gtc ggt gtt ttg        288
Ala Leu Asn Gly Ile Ala Gly Ser Tyr Ala Glu His Val Gly Val Leu
                 85                  90                  95 cac gtt gtt ggt gtc cca tcc atc tct gct caa gct aag caa ttg ttg        336
His Val Val Gly Val Pro Ser Ile Ser Ala Gln Ala Lys Gln Leu Leu
            100                 105                 110 ttg cac cac acc ttg ggt aac ggt gac ttc act gtt ttc cac aga atg        384
Leu His His Thr Leu Gly Asn Gly Asp Phe Thr Val Phe His Arg Met
        115                 120                 125 tct gcc aac att tct gaa acc act gct atg atc act gac att gct acc        432
Ser Ala Asn Ile Ser Glu Thr Thr Ala Met Ile Thr Asp Ile Ala Thr
130                 135                 140 gcc cca gct gaa att gac aga tgt atc aga acc act tac gtc acc caa        480
Ala Pro Ala Glu Ile Asp Arg Cys Ile Arg Thr Thr Tyr Val Thr Gln
145                 150                 155                 160 aga cca gtc tac tta ggt ttg cca gct aac ttg gtc gac ttg aac gtc        528
Arg Pro Val Tyr Leu Gly Leu Pro Ala Asn Leu Val Asp Leu Asn Val
                165                 170                 175 cca gct aag ttg ttg caa act cca att gac atg tct ttg aag cca aac        576
Pro Ala Lys Leu Leu Gln Thr Pro Ile Asp Met Ser Leu Lys Pro Asn
            180                 185                 190 gat gct gaa tcc gaa aag gaa gtc att gac acc atc ttg gct ttg gtc        624
Asp Ala Glu Ser Glu Lys Glu Val Ile Asp Thr Ile Leu Ala Leu Val
        195                 200                 205 aag gat gct aag aac cca gtt atc ttg gct gat gct tgt tgt tcc aga        672
Lys Asp Ala Lys Asn Pro Val Ile Leu Ala Asp Ala Cys Cys Ser Arg
210                 215                 220 cac gac gtc aag gct gaa act aag aag ttg att gac ttg act caa ttc        720
His Asp Val Lys Ala Glu Thr Lys Lys Leu Ile Asp Leu Thr Gln Phe
225                 230                 235                 240 cca gct ttc gtc acc cca atg ggt aag ggt tcc att gac gaa caa cac        768
Pro Ala Phe Val Thr Pro Met Gly Lys Gly Ser Ile Asp Glu Gln His
                245                 250                 255 cca aga tac ggt ggt gtt tac gtc ggt acc ttg tcc aag cca gaa gtt        816
Pro Arg Tyr Gly Gly Val Tyr Val Gly Thr Leu Ser Lys Pro Glu Val
            260                 265                 270 aag gaa gcc gtt gaa tct gct gac ttg att ttg tct gtc ggt gct ttg        864
Lys Glu Ala Val Glu Ser Ala Asp Leu Ile Leu Ser Val Gly Ala Leu
        275                 280                 285 ttg tct gat ttc aac acc ggt tct ttc tct tac tct tac aag acc aag        912
Leu Ser Asp Phe Asn Thr Gly Ser Phe Ser Tyr Ser Tyr Lys Thr Lys
290                 295                 300 aac att gtc gaa ttc cac tcc gac cac atg aag atc aga aac gcc act        960
Asn Ile Val Glu Phe His Ser Asp His Met Lys Ile Arg Asn Ala Thr
305                 310                 315                 320 ttc cca ggt gtc caa atg aaa ttc gtt ttg caa aag ttg ttg acc act       1008
Phe Pro Gly Val Gln Met Lys Phe Val Leu Gln Lys Leu Leu Thr Thr
                325                 330                 335 att gct gac gcc gct aag ggt tac aag cca gtt gct gtc cca gct aga       1056
Ile Ala Asp Ala Ala Lys Gly Tyr Lys Pro Val Ala Val Pro Ala Arg
            340                 345                 350 act cca gct aac gct gct gtc cca gct tct acc cca ttg aag caa gaa       1104
Thr Pro Ala Asn Ala Ala Val Pro Ala Ser Thr Pro Leu Lys Gln Glu
        355                 360                 365 tgg atg tgg aac caa ttg ggt aac ttc ttg caa gaa ggt gat gtt gtc       1152
Trp Met Trp Asn Gln Leu Gly Asn Phe Leu Gln Glu Gly Asp Val Val
370                 375                 380
```

| | | | | | | | | | | | | | | | | |
|---|---|---|---|---|---|---|---|---|---|---|---|---|---|---|---|---|
| att | gct | gaa | acc | ggt | acc | tcc | gct | ttc | ggt | atc | aac | caa | acc | act | ttc | 1200 |
| Ile | Ala | Glu | Thr | Gly | Thr | Ser | Ala | Phe | Gly | Ile | Asn | Gln | Thr | Thr | Phe | |
| 385 | | | | 390 | | | | | 395 | | | | | 400 | | |
| cca | aac | aac | acc | tac | ggt | atc | tct | caa | gtc | tta | tgg | ggt | tcc | att | ggt | 1248 |
| Pro | Asn | Asn | Thr | Tyr | Gly | Ile | Ser | Gln | Val | Leu | Trp | Gly | Ser | Ile | Gly | |
| | | | | 405 | | | | | 410 | | | | | 415 | | |
| ttc | acc | act | ggt | gct | acc | ttg | ggt | gct | gct | ttc | gct | gct | gaa | gaa | att | 1296 |
| Phe | Thr | Thr | Gly | Ala | Thr | Leu | Gly | Ala | Ala | Phe | Ala | Ala | Glu | Glu | Ile | |
| | | | 420 | | | | | 425 | | | | | 430 | | | |
| gat | cca | aag | aag | aga | gtt | atc | tta | ttc | att | ggt | gac | ggt | tct | ttg | caa | 1344 |
| Asp | Pro | Lys | Lys | Arg | Val | Ile | Leu | Phe | Ile | Gly | Asp | Gly | Ser | Leu | Gln | |
| | | 435 | | | | | 440 | | | | | 445 | | | | |
| ttg | act | gtt | caa | gaa | atc | tcc | acc | atg | atc | aga | tgg | ggc | ttg | aag | cca | 1392 |
| Leu | Thr | Val | Gln | Glu | Ile | Ser | Thr | Met | Ile | Arg | Trp | Gly | Leu | Lys | Pro | |
| 450 | | | | | 455 | | | | | 460 | | | | | | |
| tac | ttg | ttc | gtc | ttg | aac | aac | gat | ggt | tac | acc | att | gaa | aag | ttg | att | 1440 |
| Tyr | Leu | Phe | Val | Leu | Asn | Asn | Asp | Gly | Tyr | Thr | Ile | Glu | Lys | Leu | Ile | |
| 465 | | | | 470 | | | | | 475 | | | | | 480 | | |
| cac | ggt | cca | aag | gct | caa | tac | aac | gaa | att | caa | ggt | tgg | gac | cac | cta | 1488 |
| His | Gly | Pro | Lys | Ala | Gln | Tyr | Asn | Glu | Ile | Gln | Gly | Trp | Asp | His | Leu | |
| | | | 485 | | | | | 490 | | | | | 495 | | | |
| tcc | ttg | ttg | cca | act | ttc | ggt | gct | aag | gac | tat | gaa | acc | cac | aga | gtc | 1536 |
| Ser | Leu | Leu | Pro | Thr | Phe | Gly | Ala | Lys | Asp | Tyr | Glu | Thr | His | Arg | Val | |
| | | | 500 | | | | | 505 | | | | | 510 | | | |
| gct | acc | acc | ggt | gaa | tgg | gac | aag | ttg | acc | caa | gac | aag | tct | ttc | aac | 1584 |
| Ala | Thr | Thr | Gly | Glu | Trp | Asp | Lys | Leu | Thr | Gln | Asp | Lys | Ser | Phe | Asn | |
| | | 515 | | | | | 520 | | | | | 525 | | | | |
| gac | aac | tct | aag | atc | aga | atg | att | gaa | atc | atg | ttg | cca | gtc | ttc | gat | 1632 |
| Asp | Asn | Ser | Lys | Ile | Arg | Met | Ile | Glu | Ile | Met | Leu | Pro | Val | Phe | Asp | |
| | | 530 | | | | | 535 | | | | | 540 | | | | |
| gct | cca | caa | aac | ttg | gtt | gaa | caa | gct | aag | ttg | act | gct | gct | acc | aac | 1680 |
| Ala | Pro | Gln | Asn | Leu | Val | Glu | Gln | Ala | Lys | Leu | Thr | Ala | Ala | Thr | Asn | |
| 545 | | | | 550 | | | | | 555 | | | | | 560 | | |
| gct | aag | caa | taa | | | | | | | | | | | | | 1692 |
| Ala | Lys | Gln | | | | | | | | | | | | | | |

<210> SEQ ID NO 34
<211> LENGTH: 563
<212> TYPE: PRT
<213> ORGANISM: Saccharomyces cerevisiae

<400> SEQUENCE: 34

Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
                20                  25                  30

Leu Leu Asp Lys Ile Tyr Glu Val Glu Gly Met Arg Trp Ala Gly Asn
            35                  40                  45

Ala Asn Glu Leu Asn Ala Ala Tyr Ala Ala Asp Gly Tyr Ala Arg Ile
        50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
                100                 105                 110

Leu His His Thr Leu Gly Asn Gly Asp Phe Thr Val Phe His Arg Met
            115                 120                 125

Ser Ala Asn Ile Ser Glu Thr Thr Ala Met Ile Thr Asp Ile Ala Thr

```
                    130                 135                 140
Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                    165                 170                 175

Pro Ala Lys Leu Leu Gln Thr Pro Ile Asp Met Ser Leu Lys Pro Asn
                    180                 185                 190

Asp Ala Glu Ser Glu Lys Glu Val Ile Asp Thr Ile Leu Ala Leu Val
                    195                 200                 205

Lys Asp Ala Lys Asn Pro Val Ile Leu Ala Asp Ala Cys Cys Ser Arg
210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                    245                 250                 255

Pro Arg Tyr Gly Gly Val Tyr Val Gly Thr Leu Ser Lys Pro Glu Val
                    260                 265                 270

Lys Glu Ala Val Glu Ser Ala Asp Leu Ile Leu Ser Val Gly Ala Leu
                    275                 280                 285

Leu Ser Asp Phe Asn Thr Gly Ser Phe Ser Tyr Ser Tyr Lys Thr Lys
290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                    325                 330                 335

Ile Ala Asp Ala Ala Lys Gly Tyr Lys Pro Val Ala Val Pro Ala Arg
                    340                 345                 350

Thr Pro Ala Asn Ala Ala Val Pro Ala Ser Thr Pro Leu Lys Gln Glu
                    355                 360                 365

Trp Met Trp Asn Gln Leu Gly Asn Phe Leu Gln Glu Gly Asp Val Val
                    370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                    405                 410                 415

Phe Thr Thr Gly Ala Thr Leu Gly Ala Ala Phe Ala Ala Glu Glu Ile
                    420                 425                 430

Asp Pro Lys Lys Arg Val Ile Leu Phe Ile Gly Asp Gly Ser Leu Gln
                    435                 440                 445

Leu Thr Val Gln Glu Ile Ser Thr Met Ile Arg Trp Gly Leu Lys Pro
                    450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                    485                 490                 495

Ser Leu Leu Pro Thr Phe Gly Ala Lys Asp Tyr Glu Thr His Arg Val
                    500                 505                 510

Ala Thr Thr Gly Glu Trp Asp Lys Leu Thr Gln Asp Lys Ser Phe Asn
                    515                 520                 525

Asp Asn Ser Lys Ile Arg Met Ile Glu Ile Met Leu Pro Val Phe Asp
                    530                 535                 540

Ala Pro Gln Asn Leu Val Glu Gln Ala Lys Leu Thr Ala Ala Thr Asn
545                 550                 555                 560
```

Ala Lys Gln

<210> SEQ ID NO 35
<211> LENGTH: 1692
<212> TYPE: DNA
<213> ORGANISM: Artificial
<220> FEATURE:
<223> OTHER INFORMATION: Saccharomyces cerevisiae pyruvate decarboxylase Pdc codon optimised gene

<400> SEQUENCE: 35

| | | | | | |
|---|---|---|---|---|---|
| atgtccgaga | tcactctggg | caaatacctg | tttgaacgtc | tgaaacaggt | gaacgttaat | 60 |
| accgtattcg | gcctgccggg | tgatttcaac | ctgtccctgc | tggacaaaat | ctatgaagtt | 120 |
| gaaggtatgc | gttgggctgg | caacgctaac | gagctgaacg | cagcgtacgc | ggcagatggt | 180 |
| tacgctcgta | tcaaaggtat | gtcttgtatc | atcaccacct | cggtgttggt | tgagctgagc | 240 |
| gccctgaacg | catcgccgg | ctcctatgca | gagcacgtgg | gcgtgctgca | cgttgtgggt | 300 |
| gtaccgtcca | tcagcgccca | ggcaaaacag | ctgctgctgc | accacaccct | gggtaacggc | 360 |
| gactttaccg | ttttccatcg | tatgtctgcg | aacatcagcg | aaactactgc | aatgattact | 420 |
| gacatcgcta | cggcaccggc | agaaatcgac | cgttgcattc | gtaccacgta | cgttactcag | 480 |
| cgcccggttt | atctgggcct | gccagccaac | ctggtggatc | tgaacgtccc | ggctaaactg | 540 |
| ctgcagactc | cgatcgatat | gtctctgaaa | cctaacgacg | cagaatctga | aagaagtt | 600 |
| atcgatacta | ttctggctct | ggtgaaagat | gcaagaacc | cagttatcct | ggctgacgca | 660 |
| tgttgctctc | gtcatgatgt | aaaggcagaa | accaaaaagc | tgatcgacct | gacgcagttc | 720 |
| ccggcgttcg | ttaccccgat | gggcaagggt | tccatcgatg | agcagcaccc | gcgttatggt | 780 |
| ggtgtatacg | ttggcacgct | gtccaaaccg | gaggtaaaag | aagcggttga | aagcgcagat | 840 |
| ctgatcctgt | ctgttggtgc | actgctgagc | gacttcaaca | ccggttcttt | ctcctatagc | 900 |
| tacaagacca | aaaacattgt | ggagtttcac | tccgatcaca | tgaaaatccg | caacgcgacc | 960 |
| tttcctggtg | tgcagatgaa | attcgtactg | cagaaactgc | tgaccaccat | cgccgacgct | 1020 |
| gcgaaaggtt | ataaaccggt | agctgtgccg | gcacgtaccc | cggcgaacgc | cgcggttcct | 1080 |
| gcatccactc | cactgaagca | ggaatggatg | tggaatcagc | tgggtaattt | cctgcaagaa | 1140 |
| ggcgacgttg | taatcgcaga | aaccggcact | agcgcgtttg | gcattaacca | gacgaccttc | 1200 |
| ccaaacaaca | cctacggtat | cagccaagtc | ctgtggggct | ctatcggctt | caccaccggt | 1260 |
| gcaaccctgg | gtgcggcttt | cgctgctgag | gagatcgacc | cgaagaaacg | tgttatcctg | 1320 |
| ttcatcggtg | acggctccct | gcagctgacc | gtccaggaga | tttctaccat | gatccgctgg | 1380 |
| ggcctgaaac | cgtacctgtt | tgtgctgaac | aacgacggct | acactattga | gaaactgatc | 1440 |
| cacggtccga | agcacagta | taatgagatc | cagggttggg | atcatctgtc | tctgctgccg | 1500 |
| acctttggcg | ctaaagacta | cgagaccac | cgcgtggcta | ccaccggcga | gtgggataaa | 1560 |
| ctgacgcagg | ataaatcctt | caatgacaat | agcaagatc | gtatgatcga | aatcatgctg | 1620 |
| ccggtctttg | atgctccgca | gaacctggta | gagcaagcaa | aactgaccgc | ggcaactaac | 1680 |
| gctaaacagt | aa | | | | | 1692 |

<210> SEQ ID NO 36
<211> LENGTH: 1707
<212> TYPE: DNA
<213> ORGANISM: Zymomonas mobilis
<220> FEATURE:
<221> NAME/KEY: CDS
<222> LOCATION: (1)..(1707)

<400> SEQUENCE: 36

```
atg agt tat act gtc ggt acc tat tta gcg gag cgg ctt gtc cag att    48
Met Ser Tyr Thr Val Gly Thr Tyr Leu Ala Glu Arg Leu Val Gln Ile
1               5                   10                  15 ggt ctc aag cat cac ttc gca gtc gcg ggc gac tac aac ctc gtc ctt    96
Gly Leu Lys His His Phe Ala Val Ala Gly Asp Tyr Asn Leu Val Leu
            20                  25                  30 ctt gac aac ctg ctt ttg aac aaa aac atg gag cag gtt tat tgc tgt   144
Leu Asp Asn Leu Leu Leu Asn Lys Asn Met Glu Gln Val Tyr Cys Cys
        35                  40                  45 aac gaa ctg aac tgc ggt ttc agt gca gaa ggt tat gct cgt gcc aaa   192
Asn Glu Leu Asn Cys Gly Phe Ser Ala Glu Gly Tyr Ala Arg Ala Lys
50                  55                  60 ggc gca gca gca gcc gtc gtt acc tac agc gtc ggt gcg ctt tcc gca   240
Gly Ala Ala Ala Ala Val Val Thr Tyr Ser Val Gly Ala Leu Ser Ala
65                  70                  75                  80 ttt gat gct atc ggt ggc gcc tat gca gaa aac ctt ccg gtt atc ctg   288
Phe Asp Ala Ile Gly Gly Ala Tyr Ala Glu Asn Leu Pro Val Ile Leu
                85                  90                  95 atc tcc ggt gct ccg aac aac aat gat cac gct gct ggt cac gtg ttg   336
Ile Ser Gly Ala Pro Asn Asn Asn Asp His Ala Ala Gly His Val Leu
            100                 105                 110 cat cac gct ctt ggc aaa acc gac tat cac tat cag ttg gaa atg gcc   384
His His Ala Leu Gly Lys Thr Asp Tyr His Tyr Gln Leu Glu Met Ala
        115                 120                 125 aag aac atc acg gcc gcc gct gaa gcg att tac acc ccg gaa gaa gct   432
Lys Asn Ile Thr Ala Ala Ala Glu Ala Ile Tyr Thr Pro Glu Glu Ala
    130                 135                 140 ccg gct aaa atc gat cac gtg att aaa act gct ctt cgt gag aag aag   480
Pro Ala Lys Ile Asp His Val Ile Lys Thr Ala Leu Arg Glu Lys Lys
145                 150                 155                 160 ccg gtt tat ctc gaa atc gct tgc aac att gct tcc atg ccc tgc gcc   528
Pro Val Tyr Leu Glu Ile Ala Cys Asn Ile Ala Ser Met Pro Cys Ala
                165                 170                 175 gct cct gga ccg gca agc gca ttg ttc aat gac gaa gcc agc gac gaa   576
Ala Pro Gly Pro Ala Ser Ala Leu Phe Asn Asp Glu Ala Ser Asp Glu
            180                 185                 190 gct tct ttg aat gca gcg gtt gaa gaa acc ctg aaa ttc atc gcc aac   624
Ala Ser Leu Asn Ala Ala Val Glu Glu Thr Leu Lys Phe Ile Ala Asn
        195                 200                 205 cgc gac aaa gtt gcc gtc ctc gtc ggc agc aag ctg cgc gca gct ggt   672
Arg Asp Lys Val Ala Val Leu Val Gly Ser Lys Leu Arg Ala Ala Gly
    210                 215                 220 gct gaa gaa gct gct gtc aaa ttt gct gat gct ctc ggt ggc gca gtt   720
Ala Glu Glu Ala Ala Val Lys Phe Ala Asp Ala Leu Gly Gly Ala Val
225                 230                 235                 240 gct acc atg gct gct gca aaa agc ttc ttc cca gaa gaa aac ccg cat   768
Ala Thr Met Ala Ala Ala Lys Ser Phe Phe Pro Glu Glu Asn Pro His
                245                 250                 255 tac atc ggc acc tca tgg ggt gaa gtc agc tat ccg ggc gtt gaa aag   816
Tyr Ile Gly Thr Ser Trp Gly Glu Val Ser Tyr Pro Gly Val Glu Lys
            260                 265                 270 acg atg aaa gaa gcc gat gcg gtt atc gct ctg gct cct gtc ttc aac   864
Thr Met Lys Glu Ala Asp Ala Val Ile Ala Leu Ala Pro Val Phe Asn
        275                 280                 285 gac tac tcc acc act ggt tgg acg gat att cct gat cct aag aaa ctg   912
Asp Tyr Ser Thr Thr Gly Trp Thr Asp Ile Pro Asp Pro Lys Lys Leu
    290                 295                 300 gtt ctc gct gaa ccg cgt tct gtc gtc gtt aac ggc att cgc ttc ccc   960
Val Leu Ala Glu Pro Arg Ser Val Val Val Asn Gly Ile Arg Phe Pro
```

```
                    305                 310                 315                 320
agc gtc cat ctg aaa gac tat ctg acc cgt ttg gct cag aaa gtt tcc              1008
Ser Val His Leu Lys Asp Tyr Leu Thr Arg Leu Ala Gln Lys Val Ser
                325                 330                 335 aag aaa acc ggt gca ttg gac ttc ttc aaa tcc ctc aat gca ggt gaa              1056
Lys Lys Thr Gly Ala Leu Asp Phe Phe Lys Ser Leu Asn Ala Gly Glu
            340                 345                 350 ctg aag aaa gcc gct ccg gct gat ccg agt gct ccg ttg gtc aac gca              1104
Leu Lys Lys Ala Ala Pro Ala Asp Pro Ser Ala Pro Leu Val Asn Ala
        355                 360                 365 gaa atc gcc cgt cag gtc gaa gct ctt ctg acc ccg aac acg acg gtt              1152
Glu Ile Ala Arg Gln Val Glu Ala Leu Leu Thr Pro Asn Thr Thr Val
370                 375                 380 att gct gaa acc ggt gac tct tgg ttc aat gct cag cgc atg aag ctc              1200
Ile Ala Glu Thr Gly Asp Ser Trp Phe Asn Ala Gln Arg Met Lys Leu
385                 390                 395                 400 ccg aac ggt gct cgc gtt gaa tat gaa atg cag tgg ggt cac att ggt              1248
Pro Asn Gly Ala Arg Val Glu Tyr Glu Met Gln Trp Gly His Ile Gly
            405                 410                 415 tgg tcc gtt cct gcc gcc ttc ggt tat gcc gtc ggt gct ccg gaa cgt              1296
Trp Ser Val Pro Ala Ala Phe Gly Tyr Ala Val Gly Ala Pro Glu Arg
        420                 425                 430 cgc aac atc ctc atg gtt ggt gat ggt tcc ttc cag ctg acg gct cag              1344
Arg Asn Ile Leu Met Val Gly Asp Gly Ser Phe Gln Leu Thr Ala Gln
        435                 440                 445 gaa gtc gct cag atg gtt cgc ctg aaa ctg ccg gtt atc atc ttc ttg              1392
Glu Val Ala Gln Met Val Arg Leu Lys Leu Pro Val Ile Ile Phe Leu
        450                 455                 460 atc aat aac tat ggt tac acc gcc gaa gtt atg atc cat gat ggt ccg              1440
Ile Asn Asn Tyr Gly Tyr Thr Ala Glu Val Met Ile His Asp Gly Pro
465                 470                 475                 480 tac aac aac atc aag aac tgg gat tat gcc ggt ctg atg gaa gtg ttc              1488
Tyr Asn Asn Ile Lys Asn Trp Asp Tyr Ala Gly Leu Met Glu Val Phe
            485                 490                 495 aac ggt aac ggt ggt tat gac agc ggt gct ggt aaa ggc ctg aag gct              1536
Asn Gly Asn Gly Gly Tyr Asp Ser Gly Ala Gly Lys Gly Leu Lys Ala
        500                 505                 510 aaa acc ggt ggc gaa ctg gca gaa gct atc aag gtt gct ctg gca aac              1584
Lys Thr Gly Gly Glu Leu Ala Glu Ala Ile Lys Val Ala Leu Ala Asn
        515                 520                 525 acc gac ggc cca acc ctg atc gaa tgc ttc atc ggt cgt gaa gac tgc              1632
Thr Asp Gly Pro Thr Leu Ile Glu Cys Phe Ile Gly Arg Glu Asp Cys
530                 535                 540 act gaa gaa ttg gtc aaa tgg ggt aag cgc gtt gct gcc gcc aac agc              1680
Thr Glu Glu Leu Val Lys Trp Gly Lys Arg Val Ala Ala Ala Asn Ser
545                 550                 555                 560 cgt aag cct gtt aac aag ctc ctc tag                                          1707
Arg Lys Pro Val Asn Lys Leu Leu
            565

<210> SEQ ID NO 37
<211> LENGTH: 568
<212> TYPE: PRT
<213> ORGANISM: Zymomonas mobilis

<400> SEQUENCE: 37

Met Ser Tyr Thr Val Gly Thr Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30
```

```
Leu Asp Asn Leu Leu Leu Asn Lys Asn Met Glu Gln Val Tyr Cys Cys
     35                  40                  45

Asn Glu Leu Asn Cys Gly Phe Ser Ala Glu Gly Tyr Ala Arg Ala Lys
 50                  55                  60

Gly Ala Ala Ala Val Val Thr Tyr Ser Val Gly Ala Leu Ser Ala
 65                  70                  75                  80

Phe Asp Ala Ile Gly Gly Ala Tyr Ala Glu Asn Leu Pro Val Ile Leu
                 85                  90                  95

Ile Ser Gly Ala Pro Asn Asn Asp His Ala Ala Gly His Val Leu
             100                 105                 110

His His Ala Leu Gly Lys Thr Asp Tyr His Tyr Gln Leu Glu Met Ala
             115                 120                 125

Lys Asn Ile Thr Ala Ala Glu Ala Ile Tyr Thr Pro Glu Glu Ala
 130                 135                 140

Pro Ala Lys Ile Asp His Val Ile Lys Thr Ala Leu Arg Glu Lys Lys
 145                 150                 155                 160

Pro Val Tyr Leu Glu Ile Ala Cys Asn Ile Ala Ser Met Pro Cys Ala
                 165                 170                 175

Ala Pro Gly Pro Ala Ser Ala Leu Phe Asn Asp Glu Ala Ser Asp Glu
             180                 185                 190

Ala Ser Leu Asn Ala Ala Val Glu Glu Thr Leu Lys Phe Ile Ala Asn
             195                 200                 205

Arg Asp Lys Val Ala Val Leu Val Gly Ser Lys Leu Arg Ala Ala Gly
 210                 215                 220

Ala Glu Glu Ala Ala Val Lys Phe Ala Asp Ala Leu Gly Gly Ala Val
 225                 230                 235                 240

Ala Thr Met Ala Ala Lys Ser Phe Phe Pro Glu Glu Asn Pro His
                 245                 250                 255

Tyr Ile Gly Thr Ser Trp Gly Glu Val Ser Tyr Pro Gly Val Glu Lys
                 260                 265                 270

Thr Met Lys Glu Ala Asp Ala Val Ile Ala Leu Ala Pro Val Phe Asn
         275                 280                 285

Asp Tyr Ser Thr Thr Gly Trp Thr Asp Ile Pro Asp Pro Lys Lys Leu
         290                 295                 300

Val Leu Ala Glu Pro Arg Ser Val Val Asn Gly Ile Arg Phe Pro
305                 310                 315                 320

Ser Val His Leu Lys Asp Tyr Leu Thr Arg Leu Ala Gln Lys Val Ser
                 325                 330                 335

Lys Lys Thr Gly Ala Leu Asp Phe Phe Lys Ser Leu Asn Ala Gly Glu
             340                 345                 350

Leu Lys Lys Ala Ala Pro Ala Asp Pro Ser Ala Pro Leu Val Asn Ala
             355                 360                 365

Glu Ile Ala Arg Gln Val Glu Ala Leu Leu Thr Pro Asn Thr Thr Val
 370                 375                 380

Ile Ala Glu Thr Gly Asp Ser Trp Phe Asn Ala Gln Arg Met Lys Leu
385                 390                 395                 400

Pro Asn Gly Ala Arg Val Glu Tyr Glu Met Gln Trp Gly His Ile Gly
                 405                 410                 415

Trp Ser Val Pro Ala Ala Phe Gly Tyr Ala Val Gly Ala Pro Glu Arg
             420                 425                 430

Arg Asn Ile Leu Met Val Gly Asp Gly Ser Phe Gln Leu Thr Ala Gln
             435                 440                 445

Glu Val Ala Gln Met Val Arg Leu Lys Leu Pro Val Ile Ile Phe Leu
 450                 455                 460
```

```
Ile Asn Asn Tyr Gly Tyr Thr Ala Glu Val Met Ile His Asp Gly Pro
465                 470                 475                 480

Tyr Asn Asn Ile Lys Asn Trp Asp Tyr Ala Gly Leu Met Glu Val Phe
                485                 490                 495

Asn Gly Asn Gly Gly Tyr Asp Ser Gly Ala Gly Lys Gly Leu Lys Ala
            500                 505                 510

Lys Thr Gly Gly Glu Leu Ala Glu Ala Ile Lys Val Ala Leu Ala Asn
        515                 520                 525

Thr Asp Gly Pro Thr Leu Ile Glu Cys Phe Ile Gly Arg Glu Asp Cys
    530                 535                 540

Thr Glu Glu Leu Val Lys Trp Gly Lys Arg Val Ala Ala Ala Asn Ser
545                 550                 555                 560

Arg Lys Pro Val Asn Lys Leu Leu
                565

<210> SEQ ID NO 38
<211> LENGTH: 1707
<212> TYPE: DNA
<213> ORGANISM: Artificial
<220> FEATURE:
<223> OTHER INFORMATION: Zymomonas mobilis pyruvate decarboxylase
      PdcI472A codon optimised gene

<400> SEQUENCE: 38
atgtcttata ctgttggtac ttatctggct gagcgtctgg tgcaaatcgg cctgaaacac      60
cactttgcag ttgctggcga ctacaacctg gttctgctgg ataacctgct gctgaacaaa     120
aacatggagc aagtttattg ctgtaacgag ctgaactgcg gcttctctgc ggagggttat     180
gcgcgtgcga aggtgccgc tgcagcagtc gtaacctact ctgtgggcgc tctgtccgcg     240
ttcgacgcaa tcggtggcgc ttacgctgaa aacctgccgg tgatcctgat agcggtgcg     300 ccgaataata cgaccatgc tgctggccac gttctgcacc acgccctggg taaaactgat     360
taccattacc agctggagat ggctaaaaac atcactgcag cagcagaagc gatctacacc     420
ccggaagagg ctccggcaaa aatcgaccac gtgattaaaa ccgctctgcg tgagaaaaag     480
ccggtatacc tggaaatcgc gtgcaacatc gcgtctatgc cgtgcgccgc accgggtccg     540
gcttctgccc tgttcaacga tgaggcgagc gatgaggcat ctctgaacgc agcagtagaa     600 gaaacccctga atttatcgc aaaccgtgac aaagtagcag tcctggtagg ttctaaactg     660
cgtgcggctg gtgcggaaga ggctgcggta aagttcgcgg atgctctggg cggtgcagtg     720
gcgaccatgg cagcggctaa atccttcttc ccagaggaga cccgcattta cattggtacc     780
tcctggggcg aagtttccta ccctggtgtg gagaaaacca tgaaagaagc cgatgctgtg     840
attgccctgg cgcctgtatt caacgattat ccaccaccg gttggaccga tatcccggac     900
ccgaagaaac tggtcctggc tgaaccgcgc tccgtagtag tgaatggcat tcgtttcccg     960
tccgtacacc tgaaggatta cctgacgcgt ctggcacaga agtatccaa gaaaactggc    1020 gcgctggact tctttaaatc cctgaacgct ggtgagctga aaaaggcggc tccggccgat    1080
ccgtccgcac cgctggtgaa cgcagagatt gcacgtcagg ttgaggcact gctgacgccg    1140
aacaccaccg taatcgcgga aacgggcgac tcttggttca acgcacagcg catgaaactg    1200
ccgaacggtg cccgcgttga atatgaaatg cagtggggtc acatcggctg gtctgtccca    1260
gcagcgtttg gttacgcggt tggtgcaccg gagcgtcgca acatcctgat ggtgggtgac    1320
ggctccttcc agctgactgc tcaggagtg gcgcagatgg tgcgcctgaa gctgccggtt    1380
atcattttcc tgatcaacaa ctacggctac accgccgagg taatgatcca cgatggtccg    1440
```

-continued

```
tacaacaaca tcaaaaactg ggactacgcc ggtctgatgg aggttttaa cggtaacggc    1500 ggttacgaca gcggtgctgg taagggtctg aaagccaaaa ccggtggcga actggcagag    1560
gcgattaaag ttgcgctggc aaacaccgat ggcccgaccc tgatcgagtg cttcatcggc    1620
cgtgaggact gcaccgagga gctggtcaaa tggggcaaac gtgtggcggc tgctaactct    1680
cgcaagccgg taaacaaact gctgtaa                                        1707
```

<210> SEQ ID NO 39
<211> LENGTH: 1644
<212> TYPE: DNA
<213> ORGANISM: Lactococcus lactis
<220> FEATURE:
<221> NAME/KEY: CDS
<222> LOCATION: (1)..(1644)

<400> SEQUENCE: 39

```
atg tat aca gta gga gat tac ctg tta gac cga tta cac gag ttg gga    48
Met Tyr Thr Val Gly Asp Tyr Leu Leu Asp Arg Leu His Glu Leu Gly
1               5                   10                  15 att gaa gaa att ttt gga gtt cct ggt gac tat aac tta caa ttt tta    96
Ile Glu Glu Ile Phe Gly Val Pro Gly Asp Tyr Asn Leu Gln Phe Leu
            20                  25                  30 gat caa att att tca cgc gaa gat atg aaa tgg att gga aat gct aat    144
Asp Gln Ile Ile Ser Arg Glu Asp Met Lys Trp Ile Gly Asn Ala Asn
        35                  40                  45 gaa tta aat gct tct tat atg gct gat ggt tat gct cgt act aaa aaa    192
Glu Leu Asn Ala Ser Tyr Met Ala Asp Gly Tyr Ala Arg Thr Lys Lys
    50                  55                  60 gct gcc gca ttt ctc acc aca ttt gga gtc ggc gaa ttg agt gcg atc    240
Ala Ala Ala Phe Leu Thr Thr Phe Gly Val Gly Glu Leu Ser Ala Ile
65                  70                  75                  80 aat gga ctg gca gga agt tat gcc gaa aat tta cca gta gta gaa att    288
Asn Gly Leu Ala Gly Ser Tyr Ala Glu Asn Leu Pro Val Val Glu Ile
                85                  90                  95 gtt ggt tca cca act tca aaa gta caa aat gac gga aaa ttt gtc cat    336
Val Gly Ser Pro Thr Ser Lys Val Gln Asn Asp Gly Lys Phe Val His
            100                 105                 110 cat aca cta gca gat ggt gat ttt aaa cac ttt atg aag atg cat gaa    384
His Thr Leu Ala Asp Gly Asp Phe Lys His Phe Met Lys Met His Glu
        115                 120                 125 cct gtt aca gca gcg cgg act tta ctg aca gca gaa aat gcc aca tat    432
Pro Val Thr Ala Ala Arg Thr Leu Leu Thr Ala Glu Asn Ala Thr Tyr
    130                 135                 140 gaa att gac cga gta ctt tct caa tta cta aaa gaa aga aaa cca gtc    480
Glu Ile Asp Arg Val Leu Ser Gln Leu Leu Lys Glu Arg Lys Pro Val
145                 150                 155                 160 tat att aac tta cca gtc gat gtt gct gca gca aaa gca gag aag cct    528
Tyr Ile Asn Leu Pro Val Asp Val Ala Ala Ala Lys Ala Glu Lys Pro
                165                 170                 175 gca tta tct tta gaa aaa gaa agc tct aca aca aat aca act gaa caa    576
Ala Leu Ser Leu Glu Lys Glu Ser Ser Thr Thr Asn Thr Thr Glu Gln
            180                 185                 190 gtg att ttg agt aag att gaa gaa agt ttg aaa aat gcc caa aaa cca    624
Val Ile Leu Ser Lys Ile Glu Glu Ser Leu Lys Asn Ala Gln Lys Pro
        195                 200                 205 gta gtg att gca gga cac gaa gta att agt ttt ggt tta gaa aaa acg    672
Val Val Ile Ala Gly His Glu Val Ile Ser Phe Gly Leu Glu Lys Thr
    210                 215                 220 gta act cag ttt gtt tca gaa aca aaa cta ccg att acg aca cta aat    720
Val Thr Gln Phe Val Ser Glu Thr Lys Leu Pro Ile Thr Thr Leu Asn
```

```
                  225                 230                 235                 240
ttt  ggt  aaa  agt  gct  gtt  gat  gaa  tct  ttg  ccc  tca  ttt  tta  gga  ata        768
Phe  Gly  Lys  Ser  Ala  Val  Asp  Glu  Ser  Leu  Pro  Ser  Phe  Leu  Gly  Ile
                    245                 250                 255 tat  aac  ggg  aaa  ctt  tca  gaa  atc  agt  ctt  aaa  aat  ttt  gtg  gag  tcc        816
Tyr  Asn  Gly  Lys  Leu  Ser  Glu  Ile  Ser  Leu  Lys  Asn  Phe  Val  Glu  Ser
               260                 265                 270 gca  gac  ttt  atc  cta  atg  ctt  gga  gtg  aag  ctt  acg  gac  tcc  tca  aca        864
Ala  Asp  Phe  Ile  Leu  Met  Leu  Gly  Val  Lys  Leu  Thr  Asp  Ser  Ser  Thr
          275                 280                 285 ggt  gca  ttc  aca  cat  cat  tta  gat  gaa  aat  aaa  atg  att  tca  cta  aac        912
Gly  Ala  Phe  Thr  His  His  Leu  Asp  Glu  Asn  Lys  Met  Ile  Ser  Leu  Asn
     290                 295                 300 ata  gat  gaa  gga  ata  att  ttc  aat  aaa  gtg  gta  gaa  gat  ttt  gat  ttt        960
Ile  Asp  Glu  Gly  Ile  Ile  Phe  Asn  Lys  Val  Val  Glu  Asp  Phe  Asp  Phe
305                 310                 315                 320 aga  gca  gtg  gtt  tct  tct  tta  tca  gaa  tta  aaa  gga  ata  gaa  tat  gaa       1008
Arg  Ala  Val  Val  Ser  Ser  Leu  Ser  Glu  Leu  Lys  Gly  Ile  Glu  Tyr  Glu
                    325                 330                 335 gga  caa  tat  att  gat  aag  caa  tat  gaa  gaa  ttt  att  cca  tca  agt  gct       1056
Gly  Gln  Tyr  Ile  Asp  Lys  Gln  Tyr  Glu  Glu  Phe  Ile  Pro  Ser  Ser  Ala
               340                 345                 350 ccc  tta  tca  caa  gac  cgt  cta  tgg  cag  gca  gtt  gaa  agt  ttg  act  caa       1104
Pro  Leu  Ser  Gln  Asp  Arg  Leu  Trp  Gln  Ala  Val  Glu  Ser  Leu  Thr  Gln
          355                 360                 365 agc  aat  gaa  aca  atc  gtt  gct  gaa  caa  gga  acc  tca  ttt  ttt  gga  gct       1152
Ser  Asn  Glu  Thr  Ile  Val  Ala  Glu  Gln  Gly  Thr  Ser  Phe  Phe  Gly  Ala
     370                 375                 380 tca  aca  att  ttc  tta  aaa  tca  aat  agt  cgt  ttt  att  gga  caa  cct  tta       1200
Ser  Thr  Ile  Phe  Leu  Lys  Ser  Asn  Ser  Arg  Phe  Ile  Gly  Gln  Pro  Leu
385                 390                 395                 400 tgg  ggt  tct  att  gga  tat  act  ttt  cca  gcg  gct  tta  gga  agc  caa  att       1248
Trp  Gly  Ser  Ile  Gly  Tyr  Thr  Phe  Pro  Ala  Ala  Leu  Gly  Ser  Gln  Ile
                    405                 410                 415 gcg  gat  aaa  gag  agc  aga  cac  ctt  tta  ttt  att  ggt  gat  ggt  tca  ctt       1296
Ala  Asp  Lys  Glu  Ser  Arg  His  Leu  Leu  Phe  Ile  Gly  Asp  Gly  Ser  Leu
               420                 425                 430 caa  ctt  acc  gta  caa  gaa  tta  gga  cta  tca  atc  aga  gaa  aaa  ctc  aat       1344
Gln  Leu  Thr  Val  Gln  Glu  Leu  Gly  Leu  Ser  Ile  Arg  Glu  Lys  Leu  Asn
          435                 440                 445 cca  att  tgt  ttt  atc  ata  aat  aat  gat  ggt  tat  aca  gtt  gaa  aga  gaa       1392
Pro  Ile  Cys  Phe  Ile  Ile  Asn  Asn  Asp  Gly  Tyr  Thr  Val  Glu  Arg  Glu
     450                 455                 460 atc  cac  gga  cct  act  caa  agt  tat  aac  gac  att  cca  atg  tgg  aat  tac       1440
Ile  His  Gly  Pro  Thr  Gln  Ser  Tyr  Asn  Asp  Ile  Pro  Met  Trp  Asn  Tyr
465                 470                 475                 480 tcg  aaa  tta  cca  gaa  aca  ttt  gga  gca  aca  gaa  gat  cgt  gta  gta  tca       1488
Ser  Lys  Leu  Pro  Glu  Thr  Phe  Gly  Ala  Thr  Glu  Asp  Arg  Val  Val  Ser
                    485                 490                 495 aaa  att  gtt  aga  aca  gag  aat  gaa  ttt  gtg  tct  gtc  atg  aaa  gaa  gcc       1536
Lys  Ile  Val  Arg  Thr  Glu  Asn  Glu  Phe  Val  Ser  Val  Met  Lys  Glu  Ala
               500                 505                 510 caa  gca  gat  gtc  aat  aga  atg  tat  tgg  ata  gaa  cta  gtt  ttg  gaa  aaa       1584
Gln  Ala  Asp  Val  Asn  Arg  Met  Tyr  Trp  Ile  Glu  Leu  Val  Leu  Glu  Lys
          515                 520                 525 gaa  gat  gcg  cca  aaa  tta  ctg  aaa  aaa  atg  ggt  aaa  tta  ttt  gct  gag       1632
Glu  Asp  Ala  Pro  Lys  Leu  Leu  Lys  Lys  Met  Gly  Lys  Leu  Phe  Ala  Glu
     530                 535                 540 caa  aat  aaa  tag                                                                    1644
Gln  Asn  Lys
```

545

<210> SEQ ID NO 40
<211> LENGTH: 547
<212> TYPE: PRT
<213> ORGANISM: Lactococcus lactis

<400> SEQUENCE: 40

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Glu Asp Met Lys Trp Ile Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Ile
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Asp Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Tyr
    130                 135                 140

Glu Ile Asp Arg Val Leu Ser Gln Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ala Leu Ser Leu Glu Lys Glu Ser Ser Thr Thr Asn Thr Thr Glu Gln
            180                 185                 190

Val Ile Leu Ser Lys Ile Glu Glu Ser Leu Lys Asn Ala Gln Lys Pro
        195                 200                 205

Val Val Ile Ala Gly His Glu Val Ile Ser Phe Gly Leu Glu Lys Thr
    210                 215                 220

Val Thr Gln Phe Val Ser Glu Thr Lys Leu Pro Ile Thr Thr Leu Asn
225                 230                 235                 240

Phe Gly Lys Ser Ala Val Asp Glu Ser Leu Pro Ser Phe Leu Gly Ile
                245                 250                 255

Tyr Asn Gly Lys Leu Ser Glu Ile Ser Leu Lys Asn Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asp Glu Asn Lys Met Ile Ser Leu Asn
    290                 295                 300

Ile Asp Glu Gly Ile Ile Phe Asn Lys Val Val Glu Asp Phe Asp Phe
305                 310                 315                 320

Arg Ala Val Val Ser Ser Leu Ser Glu Leu Lys Gly Ile Glu Tyr Glu
                325                 330                 335

Gly Gln Tyr Ile Asp Lys Gln Tyr Glu Glu Phe Ile Pro Ser Ser Ala
            340                 345                 350

Pro Leu Ser Gln Asp Arg Leu Trp Gln Ala Val Glu Ser Leu Thr Gln
        355                 360                 365

Ser Asn Glu Thr Ile Val Ala Glu Gln Gly Thr Ser Phe Phe Gly Ala

```
                        370                 375                 380
Ser Thr Ile Phe Leu Lys Ser Asn Ser Arg Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ser Ile Arg Glu Lys Leu Asn
                435                 440                 445

Pro Ile Cys Phe Ile Ile Asn Asn Asp Gly Tyr Thr Val Glu Arg Glu
        450                 455                 460

Ile His Gly Pro Thr Gln Ser Tyr Asn Asp Ile Pro Met Trp Asn Tyr
465                 470                 475                 480

Ser Lys Leu Pro Glu Thr Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Val Asn Arg Met Tyr Trp Ile Glu Leu Val Leu Glu Lys
                515                 520                 525

Glu Asp Ala Pro Lys Leu Leu Lys Lys Met Gly Lys Leu Phe Ala Glu
        530                 535                 540

Gln Asn Lys
545

<210> SEQ ID NO 41
<211> LENGTH: 1644
<212> TYPE: DNA
<213> ORGANISM: Artificial
<220> FEATURE:
<223> OTHER INFORMATION: Lactococcus lactis branched chain
      alpha-ketoacid decarboxylase KdcA codon optimised gene

<400> SEQUENCE: 41
atgtatactg ttggtgatta tctgctggac cgtctgcatg aactgggcat tgaagaaatc     60
ttcggtgtcc aggcgactac aacctgcag ttcctggacc agatcatctc ccgcgaagat     120
atgaaatgga tcggtaacgc aaacgagctg aacgcgtctt atatggctga tggttatgct     180
cgcaccaaaa aggctgcggc ctttctgacc acctttggtg tgggcgagct gagcgcgatc     240
aacggcctgg caggttccta cgctgagaac ctgccggtag tagaaatcgt tggttccccg     300
acctctaagg ttcagaacga cggcaaattc gtacatcaca ccctggcgga cggcgatttt     360
aagcacttta tgaaaatgca cgaaccggtc accgccgctc gcactctgct gaccgcggaa     420
aacgcaacgt acgagatcga tcgtgtactg tcccagctgc tgaaagaacg taaaccggtg     480
tatatcaatc tgccggttga tgtcgctgcg gccaaagcag agaaaccggc actgtccctg     540
gagaaggaga gctccactac taacaccacc gaacaggtta tcctgtccaa aattgaagaa     600
tctctgaaaa acgcacagaa accggtggtt atcgcaggtc acgaggttat ctccttcggc     660
ctggagaaaa ctgttactca attcgtctct gaaacgaaac tgccgatcac gaccctgaac     720
tttggcaagt ccgcagttga cgaatctctg ccttcttttcc tgggcattta caacggcaaa     780
ctgtccgaga tctccctgaa gaacttcgta gaatccgctg actttatcct gatgctgggt     840
gtgaaactga ccgactcctc taccggtgcg ttcacgcacc atctggatga aacaaaaatg     900
atcagcctga catcgacga gggtatcatc ttcaacaagg tagttgaaga tttcgacttc     960
cgtgctgttg tcagcagcct gtccgagctg aaaggcattg agtacgaggg tcaatacatc    1020
```

-continued

```
gataaacagt acgaagagtt tattccgtct tctgcaccgc tgagccagga ccgcctgtgg    1080
caggcagttg agtccctgac gcagtccaac gaaactatcg tagcggaaca aggtacctct    1140
ttcttcggtg cttctaccat ctttctgaag tccaactctc gctttatcgg tcagccgctg    1200
tggggttcta tcggttacac gttcccggct gcgctgggta gccagatcgc tgataaagag    1260
tctcgtcatc tgctgttcat cggtgatggt tccctgcagc tgactgtaca ggaactgggt    1320
ctgtctatcc gtgaaaaact gaacccgatt tgttttatca tcaataacga tggctacact    1380
gttgagcgtg aaattcatgg tccgactcag tcttacaacg atattccgat gtggaactac    1440
tctaaactgc cggaaacctt cggtgcaact gaggatcgcg tcgtgagcaa gattgtgcgt    1500
actgagaacg agttcgtatc tgttatgaaa gaggcgcagg cagatgtgaa ccgcatgtac    1560
tggatcgaac tggttctgga aaagaggat gcaccgaaac tgctgaagaa aatgggtaaa     1620
ctgtttgcgg agcagaacaa gtaa                                          1644
```

```
<210> SEQ ID NO 42
<211> LENGTH: 1647
<212> TYPE: DNA
<213> ORGANISM: Lactococcus lactis
<220> FEATURE:
<221> NAME/KEY: CDS
<222> LOCATION: (1)..(1647)

<400> SEQUENCE: 42
```

| atg tat aca gta gga gat tac cta tta gac cga tta cac gag tta gga | 48 |
|---|---|
| Met Tyr Thr Val Gly Asp Tyr Leu Leu Asp Arg Leu His Glu Leu Gly | |
| 1               5                   10                  15      | |

| att gaa gaa att ttt gga gtc cct gga gac tat aac tta caa ttt tta | 96 |
|---|---|
| Ile Glu Glu Ile Phe Gly Val Pro Gly Asp Tyr Asn Leu Gln Phe Leu | |
|                 20                  25                  30      | |

| gat caa att att tcc cac aag gat atg aaa tgg gtc gga aat gct aat | 144 |
|---|---|
| Asp Gln Ile Ile Ser His Lys Asp Met Lys Trp Val Gly Asn Ala Asn | |
|             35                  40                  45          | |

| gaa tta aat gct tca tat atg gct gat ggc tat gct cgt act aaa aaa | 192 |
|---|---|
| Glu Leu Asn Ala Ser Tyr Met Ala Asp Gly Tyr Ala Arg Thr Lys Lys | |
|         50                  55                  60              | |

| gct gcc gca ttt ctt aca acc ttt gga gta ggt gaa ttg agt gca gtt | 240 |
|---|---|
| Ala Ala Ala Phe Leu Thr Thr Phe Gly Val Gly Glu Leu Ser Ala Val | |
| 65                  70                  75                  80  | |

| aat gga tta gca gga agt tac gcc gaa aat tta cca gta gta gaa ata | 288 |
|---|---|
| Asn Gly Leu Ala Gly Ser Tyr Ala Glu Asn Leu Pro Val Val Glu Ile | |
|                 85                  90                  95      | |

| gtg gga tca cct aca tca aaa gtt caa aat gaa gga aaa ttt gtt cat | 336 |
|---|---|
| Val Gly Ser Pro Thr Ser Lys Val Gln Asn Glu Gly Lys Phe Val His | |
|             100                 105                 110         | |

| cat acg ctg gct gac ggt gat ttt aaa cac ttt atg aaa atg cac gaa | 384 |
|---|---|
| His Thr Leu Ala Asp Gly Asp Phe Lys His Phe Met Lys Met His Glu | |
|         115                 120                 125             | |

| cct gtt aca gca gct cga act tta ctg aca gca gaa aat gca acc gtt | 432 |
|---|---|
| Pro Val Thr Ala Ala Arg Thr Leu Leu Thr Ala Glu Asn Ala Thr Val | |
| 130                 135                 140                     | |

| gaa att gac cga gta ctt tct gca cta tta aaa gaa aga aaa cct gtc | 480 |
|---|---|
| Glu Ile Asp Arg Val Leu Ser Ala Leu Leu Lys Glu Arg Lys Pro Val | |
| 145                 150                 155                 160 | |

| tat atc aac tta cca gtt gat gtt gct gct gca aaa gca gag aaa ccc | 528 |
|---|---|
| Tyr Ile Asn Leu Pro Val Asp Val Ala Ala Ala Lys Ala Glu Lys Pro | |
|                 165                 170                 175     | |

| tca ctc cct ttg aaa aag gaa aac tca act tca aat aca agt gac caa | 576 |
|---|---|
| Ser Leu Pro Leu Lys Lys Glu Asn Ser Thr Ser Asn Thr Ser Asp Gln | |
|             180                 185                 190         | |

-continued

| | |
|---|---|
| gaa att ttg aac aaa att caa gaa agc ttg aaa aat gcc aaa aaa cca<br>Glu Ile Leu Asn Lys Ile Gln Glu Ser Leu Lys Asn Ala Lys Lys Pro<br>195                      200                    205 | 624 |
| atc gtg att aca gga cat gaa ata att agt ttt ggc tta gaa aaa aca<br>Ile Val Ile Thr Gly His Glu Ile Ile Ser Phe Gly Leu Glu Lys Thr<br>210                      215                    220 | 672 |
| gtc act caa ttt att tca aag aca aaa cta cct att acg aca tta aac<br>Val Thr Gln Phe Ile Ser Lys Thr Lys Leu Pro Ile Thr Thr Leu Asn<br>225                      230                    235                    240 | 720 |
| ttt ggt aaa agt tca gtt gat gaa gcc ctc cct tca ttt tta gga atc<br>Phe Gly Lys Ser Ser Val Asp Glu Ala Leu Pro Ser Phe Leu Gly Ile<br>                    245                    250                    255 | 768 |
| tat aat ggt aca ctc tca gag cct aat ctt aaa gaa ttc gtg gaa tca<br>Tyr Asn Gly Thr Leu Ser Glu Pro Asn Leu Lys Glu Phe Val Glu Ser<br>                260                    265                    270 | 816 |
| gcc gac ttc atc ttg atg ctt gga gtt aaa ctc aca gac tct tca aca<br>Ala Asp Phe Ile Leu Met Leu Gly Val Lys Leu Thr Asp Ser Ser Thr<br>                    275                    280                    285 | 864 |
| gga gcc ttc act cat cat tta aat gaa aat aaa atg att tca ctg aat<br>Gly Ala Phe Thr His His Leu Asn Glu Asn Lys Met Ile Ser Leu Asn<br>290                      295                    300 | 912 |
| ata gat gaa gga aaa ata ttt aac gaa aga atc caa aat ttt gat ttt<br>Ile Asp Glu Gly Lys Ile Phe Asn Glu Arg Ile Gln Asn Phe Asp Phe<br>305                      310                    315                    320 | 960 |
| gaa tcc ctc atc tcc tct ctc tta gac cta agc gaa ata gaa tac aaa<br>Glu Ser Leu Ile Ser Ser Leu Leu Asp Leu Ser Glu Ile Glu Tyr Lys<br>                    325                    330                    335 | 1008 |
| gga aaa tat atc gat aaa aag caa gaa gac ttt gtt cca tca aat gcg<br>Gly Lys Tyr Ile Asp Lys Lys Gln Glu Asp Phe Val Pro Ser Asn Ala<br>                    340                    345                    350 | 1056 |
| ctt tta tca caa gac cgc cta tgg caa gca gtt gaa aac cta act caa<br>Leu Leu Ser Gln Asp Arg Leu Trp Gln Ala Val Glu Asn Leu Thr Gln<br>                    355                    360                    365 | 1104 |
| agc aat gaa aca atc gtt gct gaa caa ggg aca tca ttc ttt ggc gct<br>Ser Asn Glu Thr Ile Val Ala Glu Gln Gly Thr Ser Phe Phe Gly Ala<br>370                      375                    380 | 1152 |
| tca tca att ttc tta aaa tca aag agt cat ttt att ggt caa ccc tta<br>Ser Ser Ile Phe Leu Lys Ser Lys Ser His Phe Ile Gly Gln Pro Leu<br>385                      390                    395                    400 | 1200 |
| tgg gga tca att gga tat aca ttc cca gca gca tta gga agc caa att<br>Trp Gly Ser Ile Gly Tyr Thr Phe Pro Ala Ala Leu Gly Ser Gln Ile<br>                    405                    410                    415 | 1248 |
| gca gat aaa gaa agc aga cac ctt tta ttt att ggt gat ggt tca ctt<br>Ala Asp Lys Glu Ser Arg His Leu Leu Phe Ile Gly Asp Gly Ser Leu<br>                    420                    425                    430 | 1296 |
| caa ctt aca gtg caa gaa tta gga tta gca atc aga gaa aaa att aat<br>Gln Leu Thr Val Gln Glu Leu Gly Leu Ala Ile Arg Glu Lys Ile Asn<br>                    435                    440                    445 | 1344 |
| cca att tgc ttt att atc aat aat gat ggt tat aca gtc gaa aga gaa<br>Pro Ile Cys Phe Ile Ile Asn Asn Asp Gly Tyr Thr Val Glu Arg Glu<br>450                      455                    460 | 1392 |
| att cat gga cca aat caa agc tac aat gat att cca atg tgg aat tac<br>Ile His Gly Pro Asn Gln Ser Tyr Asn Asp Ile Pro Met Trp Asn Tyr<br>465                      470                    475                    480 | 1440 |
| tca aaa tta cca gaa tcg ttt gga gca aca gaa gat cga gta gtc tca<br>Ser Lys Leu Pro Glu Ser Phe Gly Ala Thr Glu Asp Arg Val Val Ser<br>                    485                    490                    495 | 1488 |
| aaa atc gtt aga act gaa aat gaa ttt gtg tct gtc atg aaa gaa gct<br>Lys Ile Val Arg Thr Glu Asn Glu Phe Val Ser Val Met Lys Glu Ala<br>                    500                    505                    510 | 1536 |

```
caa gca gat cca aat aga atg tac tgg att gag tta att ttg gca aaa    1584
Gln Ala Asp Pro Asn Arg Met Tyr Trp Ile Glu Leu Ile Leu Ala Lys
        515                 520                 525 gaa ggt gca cca aaa gta ctg aaa aaa atg ggc aaa cta ttt gct gaa    1632
Glu Gly Ala Pro Lys Val Leu Lys Lys Met Gly Lys Leu Phe Ala Glu
    530                 535                 540 caa aat aaa tca taa                                                1647
Gln Asn Lys Ser
545

<210> SEQ ID NO 43
<211> LENGTH: 548
<212> TYPE: PRT
<213> ORGANISM: Lactococcus lactis

<400> SEQUENCE: 43

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asp Glu Gly Lys Ile Phe Asn Glu Arg Ile Gln Asn Phe Asp Phe
305                 310                 315                 320
```

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
            405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
            485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Gly Ala Pro Lys Val Leu Lys Lys Met Gly Lys Leu Phe Ala Glu
        530                 535                 540

Gln Asn Lys Ser
545

<210> SEQ ID NO 44
<211> LENGTH: 1647
<212> TYPE: DNA
<213> ORGANISM: Artificial
<220> FEATURE:
<223> OTHER INFORMATION: Lactococcus lactis -ketoisovalerate
      decarboxylase KivD codon optimised gene

<400> SEQUENCE: 44
atgtatactg ttggtgatta cctgctggat cgtctgcatg aactgggcat cgaggaaatt      60
ttcggcgtac ctggtgacta taacctgcag ttcctggatc agatcatttc ccacaaagat     120
atgaaatggg ttggtaacgc gaacgagctg aatgcaagct acatggctga cggttatgca     180
cgcaccaaga agctgcggc gttcctgact acttttggcg tcggcgagct gtctgcggta      240
aacggtctgg ccggctccta cgcggaaaac ctgccggtag tagaaatcgt cggttccccg     300
acctctaaag ttcagaacga gggtaaattc gtgcaccata ctctggccga tggtgacttc     360
aaacacttca tgaagatgca cgaaccggtc actgctgctc gtacgctgct gaccgcggaa     420
aatgcgactg tcgagattga tcgtgtactg agcgcactgc tgaaagaacg caagcctgta     480
tacatcaacc tgccggttga tgtcgcggcc gccaaagcgg aaaaccatc tctgccgctg      540 aaaaaggaga cagcacctc taacaccagc gaccaggaaa tcctgaacaa gatccaggag     600
tctctgaaga acgctaaaaa gccgatcgta atcaccggcc atgagattat ctctttcggt     660
ctggagaaaa ctgtcaccca gttcatcagc aaaaccaaac tgccgatcac caccctgaac      720

-continued

```
ttcggtaaat cctccgttga cgaagcgctg ccgtcctttc tgggtattta caacggcact      780
ctgtctgagc cgaacctgaa agagttcgtg gagtctgcgg attttatcct gatgctgggc      840
gtgaaactga cggattcctc caccggtgca ttcacccacc acctgaatga gaataaaatg      900
atctctctga acattgatga gggcaaaatc ttcaacgagc gtattcagaa cttcgatttc      960
gaatccctga tctcctccct gctggatctg tccgagattg aatataaagg caaatacatt     1020
gataagaagc aagaggactt cgtaccgtct aacgcgctgc tgagccagga ccgtctgtgg     1080
caagctgtgg aaaacctgac ccagtccaac gaaaccatcg tggcggaaca gggtacctcc     1140
ttcttcggtg ctagctctat cttcctgaaa tctaaaagcc acttcatcgg tcagccactg     1200
tggggctcta ttggctacac cttcccggca gcgctgggtt cccaaatcgc agacaaagaa     1260
tcccgccacc tgctgttcat tggtgacggc tctctgcaac tgaccgtaca ggagctgggt     1320
ctggcgattc gtgagaaaat caacccgatt tgtttcatca tcaacaacga tggctacact     1380
gttgagcgtg agatccacgg cccgaaccag tcctacaacg acattccgat gtggaactac     1440
tctaaactgc cggaatcctt cggtgcgact gaagaccgtg tcgtaagcaa gatcgtccgt     1500
accgaaaacg aattcgtgtc tgtcatgaaa gaagcacagg cggacccgaa ccgcatgtac     1560
tggatcgagc tgattctggc taaagagggc gcgccaaaag tactgaaaaa gatgggtaaa     1620
ctgttcgcag aacagaacaa atcctaa                                          1647
```

<210> SEQ ID NO 45
<211> LENGTH: 3696
<212> TYPE: DNA
<213> ORGANISM: Mycobacterium tuberculosis
<220> FEATURE:
<221> NAME/KEY: CDS
<222> LOCATION: (1)..(3696)

<400> SEQUENCE: 45

```
gtg gcc aac ata agt tca cca ttc ggg caa aac gaa tgg ctg gtc gaa       48
Val Ala Asn Ile Ser Ser Pro Phe Gly Gln Asn Glu Trp Leu Val Glu
1               5                   10                  15 gag atg tac cgc aag ttc cgc gac gac ccc tcc tcg gtc gat ccc agc       96
Glu Met Tyr Arg Lys Phe Arg Asp Asp Pro Ser Ser Val Asp Pro Ser
            20                  25                  30 tgg cac gag ttc ctg gtt gac tac agc ccc gaa ccc acc tcc caa cca      144
Trp His Glu Phe Leu Val Asp Tyr Ser Pro Glu Pro Thr Ser Gln Pro
        35                  40                  45 gct gcc gaa cca acc cgg gtt acc tcg cca ctc gtt gcc gag cgg gcc      192
Ala Ala Glu Pro Thr Arg Val Thr Ser Pro Leu Val Ala Glu Arg Ala
    50                  55                  60 gct gcg gcc gcc ccg cag gca ccc ccc aag ccg gcc gac acc gcg gcc      240
Ala Ala Ala Ala Pro Gln Ala Pro Pro Lys Pro Ala Asp Thr Ala Ala
65                  70                  75                  80 gcg ggc aac ggc gtg gtc gcc gca ctg gcc gcc aaa act gcc gtt ccc      288
Ala Gly Asn Gly Val Val Ala Ala Leu Ala Ala Lys Thr Ala Val Pro
                85                  90                  95 ccg cca gcc gaa ggt gac gag gta gcg gtg ctg cgc ggc gcc gcc gcg      336
Pro Pro Ala Glu Gly Asp Glu Val Ala Val Leu Arg Gly Ala Ala Ala
            100                 105                 110 gcc gtc gtc aag aac atg tcc gcg tcg ttg gag gtg ccg acg gcg acc      384
Ala Val Val Lys Asn Met Ser Ala Ser Leu Glu Val Pro Thr Ala Thr
        115                 120                 125 agc gtc cgg gcg gtc ccg gcc aag cta ctg atc gac aac cgg atc gtc      432
Ser Val Arg Ala Val Pro Ala Lys Leu Leu Ile Asp Asn Arg Ile Val
    130                 135                 140
```

```
atc aac aac cag ttg aag cgg acc cgc ggc ggc aag atc tcg ttc acg    480
Ile Asn Asn Gln Leu Lys Arg Thr Arg Gly Gly Lys Ile Ser Phe Thr
145                 150                 155                 160 cat ttg ctg ggc tac gcc ctg gtg cag gcg gtg aag aaa ttc ccg aac    528
His Leu Leu Gly Tyr Ala Leu Val Gln Ala Val Lys Lys Phe Pro Asn
                165                 170                 175 atg aac cgg cac tac acc gaa gtc gac ggc aag ccc acc gcg gtc acg    576
Met Asn Arg His Tyr Thr Glu Val Asp Gly Lys Pro Thr Ala Val Thr
            180                 185                 190 ccg gcg cac acc aat ctc ggc ctg gcg atc gac ctg caa ggc aag gac    624
Pro Ala His Thr Asn Leu Gly Leu Ala Ile Asp Leu Gln Gly Lys Asp
        195                 200                 205 ggg aag cgt tcc ctg gtg gtg gcc ggc atc aag cgg tgc gag acc atg    672
Gly Lys Arg Ser Leu Val Val Ala Gly Ile Lys Arg Cys Glu Thr Met
    210                 215                 220 cga ttc gcg cag ttc gtc acg gcc tac gaa gac atc gta cgc cgg gcc    720
Arg Phe Ala Gln Phe Val Thr Ala Tyr Glu Asp Ile Val Arg Arg Ala
225                 230                 235                 240 cgc gac ggc aag ctg acc act gaa gac ttt gcc ggc gtg acg att tcg    768
Arg Asp Gly Lys Leu Thr Thr Glu Asp Phe Ala Gly Val Thr Ile Ser
                245                 250                 255 ctg acc aat ccc gga acc atc ggc acc gtg cat tcg gtg ccg cgg ctg    816
Leu Thr Asn Pro Gly Thr Ile Gly Thr Val His Ser Val Pro Arg Leu
            260                 265                 270 atg ccc ggc cag ggc gcc atc atc ggc gtg ggc gcc atg gaa tac ccc    864
Met Pro Gly Gln Gly Ala Ile Ile Gly Val Gly Ala Met Glu Tyr Pro
        275                 280                 285 gcc gag ttt caa ggc gcc agc gag gaa cgc atc gcc gag ctg ggc atc    912
Ala Glu Phe Gln Gly Ala Ser Glu Glu Arg Ile Ala Glu Leu Gly Ile
    290                 295                 300 ggc aaa ttg atc act ttg acc tcc acc tac gac cac cgc atc atc cag    960
Gly Lys Leu Ile Thr Leu Thr Ser Thr Tyr Asp His Arg Ile Ile Gln
305                 310                 315                 320 ggc gcg gaa tcg ggc gac ttc ctg cgc acc atc cac gag ttg ctg ctc   1008
Gly Ala Glu Ser Gly Asp Phe Leu Arg Thr Ile His Glu Leu Leu Leu
                325                 330                 335 tcg gat ggc ttc tgg gac gag gtc ttc cgc gaa ctg agc atc cca tat   1056
Ser Asp Gly Phe Trp Asp Glu Val Phe Arg Glu Leu Ser Ile Pro Tyr
            340                 345                 350 ctg ccg gtg cgc tgg agc acc gac aac ccc gac tcg atc gtc gac aag   1104
Leu Pro Val Arg Trp Ser Thr Asp Asn Pro Asp Ser Ile Val Asp Lys
        355                 360                 365 aac gct cgc gtc atg aac ttg atc gcg gcc tac cgc aac cgc ggc cat   1152
Asn Ala Arg Val Met Asn Leu Ile Ala Ala Tyr Arg Asn Arg Gly His
    370                 375                 380 ctg atg gcc gat acc gac ccg ctg cgg ttg gac aaa gct cgg ttc cgc   1200
Leu Met Ala Asp Thr Asp Pro Leu Arg Leu Asp Lys Ala Arg Phe Arg
385                 390                 395                 400 agt cac ccc gac ctc gaa gtg ctg acc cac ggc ctg acg ctg tgg gat   1248
Ser His Pro Asp Leu Glu Val Leu Thr His Gly Leu Thr Leu Trp Asp
                405                 410                 415 ctc gat cgg gtg ttc aag gtc gac ggc ttt gcc ggt gcg cag tac aag   1296
Leu Asp Arg Val Phe Lys Val Asp Gly Phe Ala Gly Ala Gln Tyr Lys
            420                 425                 430 aaa ctg cgc gac gtg ctg ggc ttg ctg cgc gat gcc tac tgc cgc cac   1344
Lys Leu Arg Asp Val Leu Gly Leu Leu Arg Asp Ala Tyr Cys Arg His
        435                 440                 445 atc ggc gtg gag tac gcc cat atc ctc gac ccc gaa caa aag gag tgg   1392
Ile Gly Val Glu Tyr Ala His Ile Leu Asp Pro Glu Gln Lys Glu Trp
    450                 455                 460
```

```
ctc gaa caa cgg gtc gag acc aag cac gtc aaa ccc act gtg gcc caa      1440
Leu Glu Gln Arg Val Glu Thr Lys His Val Lys Pro Thr Val Ala Gln
465                 470                 475                 480 cag aaa tac atc ctc agc aag ctc aac gcc gcc gag gcc ttt gaa acg      1488
Gln Lys Tyr Ile Leu Ser Lys Leu Asn Ala Ala Glu Ala Phe Glu Thr
                485                 490                 495 ttc cta cag acc aag tac gtc ggc cag aag cgg ttc tcg ctg gaa ggc      1536
Phe Leu Gln Thr Lys Tyr Val Gly Gln Lys Arg Phe Ser Leu Glu Gly
                500                 505                 510 gcc gaa agc gtg atc ccg atg atg gac gcg gcg atc gac cag tgc gct      1584
Ala Glu Ser Val Ile Pro Met Met Asp Ala Ala Ile Asp Gln Cys Ala
            515                 520                 525 gag cac ggc ctc gac gag gtg gtc atc ggg atg ccg cac cgg ggc cgg      1632
Glu His Gly Leu Asp Glu Val Val Ile Gly Met Pro His Arg Gly Arg
        530                 535                 540 ctc aac gtg ctg gcc aac atc gtc ggc aag ccg tac tcg cag atc ttc      1680
Leu Asn Val Leu Ala Asn Ile Val Gly Lys Pro Tyr Ser Gln Ile Phe
545                 550                 555                 560 acc gag ttc gag ggc aac ctg aat ccg tcg cag gcg cac ggc tcc ggt      1728
Thr Glu Phe Glu Gly Asn Leu Asn Pro Ser Gln Ala His Gly Ser Gly
                565                 570                 575 gac gtc aag tac cac ctg ggc gcc acc ggg ctg tac ctg cag atg ttc      1776
Asp Val Lys Tyr His Leu Gly Ala Thr Gly Leu Tyr Leu Gln Met Phe
                580                 585                 590 ggc gac aac gac att cag gtg tcg ctg acc gcc aac ccg tcg cat ctg      1824
Gly Asp Asn Asp Ile Gln Val Ser Leu Thr Ala Asn Pro Ser His Leu
                595                 600                 605 gag gcc gtc gac ccg gtg ctg gag gga ttg gtg cgg gcc aag cag gat      1872
Glu Ala Val Asp Pro Val Leu Glu Gly Leu Val Arg Ala Lys Gln Asp
        610                 615                 620 ctg ctc gac cac gga agc atc gac agc gac ggc caa cgg gcg ttc tcg      1920
Leu Leu Asp His Gly Ser Ile Asp Ser Asp Gly Gln Arg Ala Phe Ser
625                 630                 635                 640 gtg gtg ccg ctg atg ttg cat ggc gat gcc gcg ttc gcc ggt cag ggt      1968
Val Val Pro Leu Met Leu His Gly Asp Ala Ala Phe Ala Gly Gln Gly
                645                 650                 655 gtg gtc gcc gag acg ctg aac ctg gcg aat ctg ccg ggc tac cgc gtc      2016
Val Val Ala Glu Thr Leu Asn Leu Ala Asn Leu Pro Gly Tyr Arg Val
            660                 665                 670 ggc ggc acc atc cac atc atc gtc aac aac cag atc ggc ttc acc acc      2064
Gly Gly Thr Ile His Ile Ile Val Asn Asn Gln Ile Gly Phe Thr Thr
        675                 680                 685 gcg ccc gag tat tcc agg tcc agc gag tac tgc acc gac gtc gca aag      2112
Ala Pro Glu Tyr Ser Arg Ser Ser Glu Tyr Cys Thr Asp Val Ala Lys
690                 695                 700 atg atc ggg gca ccg atc ttt cac gtc aac ggc gac gac ccg gag gcg      2160
Met Ile Gly Ala Pro Ile Phe His Val Asn Gly Asp Asp Pro Glu Ala
705                 710                 715                 720 tgt gtc tgg gtg gcg cgg ttg gcg gtg gac ttc cga caa cgg ttc aag      2208
Cys Val Trp Val Ala Arg Leu Ala Val Asp Phe Arg Gln Arg Phe Lys
                725                 730                 735 aag gac gtc gtc atc gac atg ctg tgc tac cgc cgc cgc ggg cac aac      2256
Lys Asp Val Val Ile Asp Met Leu Cys Tyr Arg Arg Arg Gly His Asn
                740                 745                 750 gag ggt gac gac ccg tcg atg acc aac ccc tac gtg tac gac gtc gtc      2304
Glu Gly Asp Asp Pro Ser Met Thr Asn Pro Tyr Val Tyr Asp Val Val
                755                 760                 765 gac acc aag cgc ggg gcc cgc aaa agc tac acc gaa gcc ctg atc gga      2352
Asp Thr Lys Arg Gly Ala Arg Lys Ser Tyr Thr Glu Ala Leu Ile Gly
770                 775                 780
```

-continued

| | |
|---|---|
| cgt ggc gac atc tcg atg aag gag gcc gag gac gcg ctg cgc gac tac<br>Arg Gly Asp Ile Ser Met Lys Glu Ala Glu Asp Ala Leu Arg Asp Tyr<br>785                  790                  795                  800 | 2400 |
| cag ggc cag ctg gaa cgg gtg ttc aac gaa gtg cgc gag ctg gag aag<br>Gln Gly Gln Leu Glu Arg Val Phe Asn Glu Val Arg Glu Leu Glu Lys<br>                  805                  810                  815 | 2448 |
| cac ggt gtg cag ccg agc gag tcg gtc gag tcc gac cag atg att ccc<br>His Gly Val Gln Pro Ser Glu Ser Val Glu Ser Asp Gln Met Ile Pro<br>        820                  825                  830 | 2496 |
| gcg ggg ctg gcc act gcg gtg gac aag tcg ctg ctg gcc cgg atc ggc<br>Ala Gly Leu Ala Thr Ala Val Asp Lys Ser Leu Leu Ala Arg Ile Gly<br>835                  840                  845 | 2544 |
| gat gcg ttc ctc gcc ttg ccg aac ggc ttc acc gcg cac ccg cga gtc<br>Asp Ala Phe Leu Ala Leu Pro Asn Gly Phe Thr Ala His Pro Arg Val<br>850                  855                  860 | 2592 |
| caa ccg gtg ctg gag aag cgc cgg gag atg gcc tat gaa ggc aag atc<br>Gln Pro Val Leu Glu Lys Arg Arg Glu Met Ala Tyr Glu Gly Lys Ile<br>865                  870                  875                  880 | 2640 |
| gac tgg gcc ttt ggc gag ctg ctg gcg ctg ggc tcg ctg gtg gcc gaa<br>Asp Trp Ala Phe Gly Glu Leu Leu Ala Leu Gly Ser Leu Val Ala Glu<br>                  885                  890                  895 | 2688 |
| ggc aag ctg gtg cgc ttg tcg ggg cag gac agc cgc cgc ggc acc ttc<br>Gly Lys Leu Val Arg Leu Ser Gly Gln Asp Ser Arg Arg Gly Thr Phe<br>900                  905                  910 | 2736 |
| tcc cag cgg cat tcg gtt ctc atc gac cgc cac act ggc gag gag ttc<br>Ser Gln Arg His Ser Val Leu Ile Asp Arg His Thr Gly Glu Glu Phe<br>915                  920                  925 | 2784 |
| aca cca ctg cag ctg ctg gcg acc aac tcc gac ggc agc ccg acc ggc<br>Thr Pro Leu Gln Leu Leu Ala Thr Asn Ser Asp Gly Ser Pro Thr Gly<br>930                  935                  940 | 2832 |
| gga aag ttc ctg gtc tac gac tcg cca ctg tcg gag tac gcc gcc gtc<br>Gly Lys Phe Leu Val Tyr Asp Ser Pro Leu Ser Glu Tyr Ala Ala Val<br>945                  950                  955                  960 | 2880 |
| ggc ttc gag tac ggc tac act gtg ggc aat ccg gac gcc gtg gtg ctc<br>Gly Phe Glu Tyr Gly Tyr Thr Val Gly Asn Pro Asp Ala Val Val Leu<br>                  965                  970                  975 | 2928 |
| tgg gag gcg cag ttc ggc gac ttc gtc aac ggc gcg cag tcg atc atc<br>Trp Glu Ala Gln Phe Gly Asp Phe Val Asn Gly Ala Gln Ser Ile Ile<br>                  980                  985                  990 | 2976 |
| gac gag ttc atc agc tcc ggt gag gcc aag tgg ggc caa ttg tcc aac<br>Asp Glu Phe Ile Ser Ser Gly Glu Ala Lys Trp Gly Gln Leu Ser Asn<br>                  995                  1000                1005 | 3024 |
| gtc gtg ctg ctg tta ccg cac ggg cac gag ggg cag gga ccc gac<br>Val Val Leu Leu Leu Pro His Gly His Glu Gly Gln Gly Pro Asp<br>     1010                   1015                   1020 | 3069 |
| cac act tct gcc cgg atc gaa cgc ttc ttg cag ttg tgg gcg gaa<br>His Thr Ser Ala Arg Ile Glu Arg Phe Leu Gln Leu Trp Ala Glu<br>1025                   1030                   1035 | 3114 |
| ggt tcg atg acc atc gcg atg ccg tcg act ccg tcg aac tac ttc<br>Gly Ser Met Thr Ile Ala Met Pro Ser Thr Pro Ser Asn Tyr Phe<br>     1040                   1045                   1050 | 3159 |
| cac ctg cta cgc cgg cat gcc ctg gac ggc atc caa cgc ccg ctg<br>His Leu Leu Arg Arg His Ala Leu Asp Gly Ile Gln Arg Pro Leu<br>1055                   1060                   1065 | 3204 |
| atc gtg ttc acg ccc aag tcg atg ttg cgt cac aag gcc gcc gtc<br>Ile Val Phe Thr Pro Lys Ser Met Leu Arg His Lys Ala Ala Val<br>     1070                   1075                   1080 | 3249 |
| agc gaa atc aag gac ttc acc gag atc aag ttc cgc tca gtg ctg<br>Ser Glu Ile Lys Asp Phe Thr Glu Ile Lys Phe Arg Ser Val Leu<br>1085                   1090                   1095 | 3294 |

| | | | | | | | | | | | | |
|---|---|---|---|---|---|---|---|---|---|---|---|---|
| gag | gaa | ccc | acc | tat | gag | gac | ggc | atc | gga | gac | cgc | aac aag gtc | 3339 |
| Glu | Glu | Pro | Thr | Tyr | Glu | Asp | Gly | Ile | Gly | Asp | Arg | Asn Lys Val |
| | 1100 | | | | 1105 | | | | 1110 | | | |
| agc | cgg | atc | ctg | ctg | acc | agt | ggc | aag | ctg | tat | tac | gag ctg gcc | 3384 |
| Ser | Arg | Ile | Leu | Leu | Thr | Ser | Gly | Lys | Leu | Tyr | Tyr | Glu Leu Ala |
| | 1115 | | | | 1120 | | | | 1125 | | | |
| gcc | cgc | aag | gcc | aag | gac | aac | cgc | aat | gac | ctc | gcg | atc gtg cgg | 3429 |
| Ala | Arg | Lys | Ala | Lys | Asp | Asn | Arg | Asn | Asp | Leu | Ala | Ile Val Arg |
| | 1130 | | | | 1135 | | | | 1140 | | | |
| ctt | gaa | cag | ctc | gcc | ccg | ctg | ccc | agg | cgt | cga | ctg | cgt gaa acg | 3474 |
| Leu | Glu | Gln | Leu | Ala | Pro | Leu | Pro | Arg | Arg | Arg | Leu | Arg Glu Thr |
| | 1145 | | | | 1150 | | | | 1155 | | | |
| ctg | gac | cgc | tac | gag | aac | gtc | aag | gag | ttc | ttc | tgg | gtc caa gag | 3519 |
| Leu | Asp | Arg | Tyr | Glu | Asn | Val | Lys | Glu | Phe | Phe | Trp | Val Gln Glu |
| | 1160 | | | | 1165 | | | | 1170 | | | |
| gaa | ccg | gcc | aac | cag | ggt | gcg | tgg | ccg | cga | ttc | ggg | ctc gaa cta | 3564 |
| Glu | Pro | Ala | Asn | Gln | Gly | Ala | Trp | Pro | Arg | Phe | Gly | Leu Glu Leu |
| | 1175 | | | | 1180 | | | | 1185 | | | |
| ccc | gag | ctg | ctg | cct | gac | aag | ttg | gcc | ggg | atc | aag | cga atc tcg | 3609 |
| Pro | Glu | Leu | Leu | Pro | Asp | Lys | Leu | Ala | Gly | Ile | Lys | Arg Ile Ser |
| | 1190 | | | | 1195 | | | | 1200 | | | |
| cgc | cgg | gcg | atg | tca | gcc | ccg | tcg | tca | ggc | tcg | tcg | aag gtg cac | 3654 |
| Arg | Arg | Ala | Met | Ser | Ala | Pro | Ser | Ser | Gly | Ser | Ser | Lys Val His |
| | 1205 | | | | 1210 | | | | 1215 | | | |
| gcc | gtc | gaa | cag | cag | gag | atc | ctc | gac | gag | gcg | ttc | ggc tga | 3696 |
| Ala | Val | Glu | Gln | Gln | Glu | Ile | Leu | Asp | Glu | Ala | Phe | Gly |
| | 1220 | | | | 1225 | | | | 1230 | | | |

<210> SEQ ID NO 46
<211> LENGTH: 1231
<212> TYPE: PRT
<213> ORGANISM: Mycobacterium tuberculosis

<400> SEQUENCE: 46

Val Ala Asn Ile Ser Ser Pro Phe Gly Gln Asn Glu Trp Leu Val Glu
1               5                   10                  15

Glu Met Tyr Arg Lys Phe Arg Asp Asp Pro Ser Ser Val Asp Pro Ser
            20                  25                  30

Trp His Glu Phe Leu Val Asp Tyr Ser Pro Glu Pro Thr Ser Gln Pro
        35                  40                  45

Ala Ala Glu Pro Thr Arg Val Thr Ser Pro Leu Val Ala Glu Arg Ala
    50                  55                  60

Ala Ala Ala Ala Pro Gln Ala Pro Pro Lys Pro Ala Asp Thr Ala Ala
65                  70                  75                  80

Ala Gly Asn Gly Val Val Ala Ala Leu Ala Ala Lys Thr Ala Val Pro
                85                  90                  95

Pro Pro Ala Glu Gly Asp Glu Val Ala Val Leu Arg Gly Ala Ala Ala
            100                 105                 110

Ala Val Val Lys Asn Met Ser Ala Ser Leu Glu Val Pro Thr Ala Thr
        115                 120                 125

Ser Val Arg Ala Val Pro Ala Lys Leu Leu Ile Asp Asn Arg Ile Val
    130                 135                 140

Ile Asn Asn Gln Leu Lys Arg Thr Arg Gly Gly Lys Ile Ser Phe Thr
145                 150                 155                 160

His Leu Leu Gly Tyr Ala Leu Val Gln Ala Val Lys Lys Phe Pro Asn
                165                 170                 175

Met Asn Arg His Tyr Thr Glu Val Asp Gly Lys Pro Thr Ala Val Thr
            180                 185                 190

```
Pro Ala His Thr Asn Leu Gly Leu Ala Ile Asp Leu Gln Gly Lys Asp
        195                 200                 205
Gly Lys Arg Ser Leu Val Val Ala Gly Ile Lys Arg Cys Glu Thr Met
210                 215                 220
Arg Phe Ala Gln Phe Val Thr Ala Tyr Glu Asp Ile Val Arg Arg Ala
225                 230                 235                 240
Arg Asp Gly Lys Leu Thr Thr Glu Asp Phe Ala Gly Val Thr Ile Ser
            245                 250                 255
Leu Thr Asn Pro Gly Thr Ile Gly Thr Val His Ser Val Pro Arg Leu
                260                 265                 270
Met Pro Gly Gln Gly Ala Ile Ile Gly Val Gly Ala Met Glu Tyr Pro
            275                 280                 285
Ala Glu Phe Gln Gly Ala Ser Glu Glu Arg Ile Ala Glu Leu Gly Ile
    290                 295                 300
Gly Lys Leu Ile Thr Leu Thr Ser Thr Tyr Asp His Arg Ile Ile Gln
305                 310                 315                 320
Gly Ala Glu Ser Gly Asp Phe Leu Arg Thr Ile His Glu Leu Leu Leu
                325                 330                 335
Ser Asp Gly Phe Trp Asp Glu Val Phe Arg Glu Leu Ser Ile Pro Tyr
                340                 345                 350
Leu Pro Val Arg Trp Ser Thr Asp Asn Pro Asp Ser Ile Val Asp Lys
                355                 360                 365
Asn Ala Arg Val Met Asn Leu Ile Ala Ala Tyr Arg Asn Arg Gly His
370                 375                 380
Leu Met Ala Asp Thr Asp Pro Leu Arg Leu Asp Lys Ala Arg Phe Arg
385                 390                 395                 400
Ser His Pro Asp Leu Glu Val Leu Thr His Gly Leu Thr Leu Trp Asp
                405                 410                 415
Leu Asp Arg Val Phe Lys Val Asp Gly Phe Ala Gly Ala Gln Tyr Lys
                420                 425                 430
Lys Leu Arg Asp Val Leu Gly Leu Leu Arg Asp Ala Tyr Cys Arg His
            435                 440                 445
Ile Gly Val Glu Tyr Ala His Ile Leu Asp Pro Glu Gln Lys Glu Trp
        450                 455                 460
Leu Glu Gln Arg Val Glu Thr Lys His Val Lys Pro Thr Val Ala Gln
465                 470                 475                 480
Gln Lys Tyr Ile Leu Ser Lys Leu Asn Ala Ala Glu Ala Phe Glu Thr
                485                 490                 495
Phe Leu Gln Thr Lys Tyr Val Gly Gln Lys Arg Phe Ser Leu Glu Gly
                500                 505                 510
Ala Glu Ser Val Ile Pro Met Met Asp Ala Ala Ile Asp Gln Cys Ala
            515                 520                 525
Glu His Gly Leu Asp Glu Val Val Ile Gly Met Pro His Arg Gly Arg
530                 535                 540
Leu Asn Val Leu Ala Asn Ile Val Gly Lys Pro Tyr Ser Gln Ile Phe
545                 550                 555                 560
Thr Glu Phe Glu Gly Asn Leu Asn Pro Ser Gln Ala His Gly Ser Gly
                565                 570                 575
Asp Val Lys Tyr His Leu Gly Ala Thr Gly Leu Tyr Leu Gln Met Phe
            580                 585                 590
Gly Asp Asn Asp Ile Gln Val Ser Leu Thr Ala Asn Pro Ser His Leu
            595                 600                 605
Glu Ala Val Asp Pro Val Leu Glu Gly Leu Val Arg Ala Lys Gln Asp
610                 615                 620
```

```
Leu Leu Asp His Gly Ser Ile Asp Ser Asp Gly Gln Arg Ala Phe Ser
625                 630                 635                 640

Val Val Pro Leu Met Leu His Gly Asp Ala Ala Phe Ala Gly Gln Gly
            645                 650                 655

Val Val Ala Glu Thr Leu Asn Leu Ala Asn Leu Pro Gly Tyr Arg Val
        660                 665                 670

Gly Gly Thr Ile His Ile Ile Val Asn Asn Gln Ile Gly Phe Thr Thr
    675                 680                 685

Ala Pro Glu Tyr Ser Arg Ser Ser Glu Tyr Cys Thr Asp Val Ala Lys
690                 695                 700

Met Ile Gly Ala Pro Ile Phe His Val Asn Gly Asp Asp Pro Glu Ala
705                 710                 715                 720

Cys Val Trp Val Ala Arg Leu Ala Val Asp Phe Arg Gln Arg Phe Lys
                725                 730                 735

Lys Asp Val Val Ile Asp Met Leu Cys Tyr Arg Arg Gly His Asn
                740                 745                 750

Glu Gly Asp Asp Pro Ser Met Thr Asn Pro Tyr Val Tyr Asp Val Val
            755                 760                 765

Asp Thr Lys Arg Gly Ala Arg Lys Ser Tyr Thr Glu Ala Leu Ile Gly
770                 775                 780

Arg Gly Asp Ile Ser Met Lys Glu Ala Glu Asp Ala Leu Arg Asp Tyr
785                 790                 795                 800

Gln Gly Gln Leu Glu Arg Val Phe Asn Glu Val Arg Glu Leu Glu Lys
                805                 810                 815

His Gly Val Gln Pro Ser Glu Ser Val Glu Ser Asp Gln Met Ile Pro
            820                 825                 830

Ala Gly Leu Ala Thr Ala Val Asp Lys Ser Leu Leu Ala Arg Ile Gly
        835                 840                 845

Asp Ala Phe Leu Ala Leu Pro Asn Gly Phe Thr Ala His Pro Arg Val
850                 855                 860

Gln Pro Val Leu Glu Lys Arg Arg Glu Met Ala Tyr Glu Gly Lys Ile
865                 870                 875                 880

Asp Trp Ala Phe Gly Glu Leu Leu Ala Leu Gly Ser Leu Val Ala Glu
                885                 890                 895

Gly Lys Leu Val Arg Leu Ser Gly Gln Asp Ser Arg Arg Gly Thr Phe
            900                 905                 910

Ser Gln Arg His Ser Val Leu Ile Asp Arg His Thr Gly Glu Glu Phe
        915                 920                 925

Thr Pro Leu Gln Leu Leu Ala Thr Asn Ser Asp Gly Ser Pro Thr Gly
930                 935                 940

Gly Lys Phe Leu Val Tyr Asp Ser Pro Leu Ser Glu Tyr Ala Ala Val
945                 950                 955                 960

Gly Phe Glu Tyr Gly Tyr Thr Val Gly Asn Pro Asp Ala Val Val Leu
                965                 970                 975

Trp Glu Ala Gln Phe Gly Asp Phe Val Asn Gly Ala Gln Ser Ile Ile
            980                 985                 990

Asp Glu Phe Ile Ser Ser Gly Glu Ala Lys Trp Gly Gln Leu Ser Asn
        995                 1000                1005

Val Val Leu Leu Leu Pro His Gly His Glu Gly Gln Gly Pro Asp
    1010                1015                1020

His Thr Ser Ala Arg Ile Glu Arg Phe Leu Gln Leu Trp Ala Glu
    1025                1030                1035

Gly Ser Met Thr Ile Ala Met Pro Ser Thr Pro Ser Asn Tyr Phe
```

|   |   |   |   |   |   |   |   |   |   |   |
|---|---|---|---|---|---|---|---|---|---|---|
| His | Leu | Leu | Arg | Arg | His | Ala | Leu | Asp | Gly | Ile | Gln | Arg | Pro | Leu |
| 1055 | | | | | 1060 | | | | | 1065 |

His Leu Leu Arg Arg His Ala Leu Asp Gly Ile Gln Arg Pro Leu
1055                1060                1065

Ile Val Phe Thr Pro Lys Ser Met Leu Arg His Lys Ala Ala Val
1070                1075                1080

Ser Glu Ile Lys Asp Phe Thr Glu Ile Lys Phe Arg Ser Val Leu
1085                1090                1095

Glu Glu Pro Thr Tyr Glu Asp Gly Ile Gly Asp Arg Asn Lys Val
1100                1105                1110

Ser Arg Ile Leu Leu Thr Ser Gly Lys Leu Tyr Tyr Glu Leu Ala
1115                1120                1125

Ala Arg Lys Ala Lys Asp Asn Arg Asn Asp Leu Ala Ile Val Arg
1130                1135                1140

Leu Glu Gln Leu Ala Pro Leu Pro Arg Arg Leu Arg Glu Thr
1145                1150                1155

Leu Asp Arg Tyr Glu Asn Val Lys Glu Phe Phe Trp Val Gln Glu
1160                1165                1170

Glu Pro Ala Asn Gln Gly Ala Trp Pro Arg Phe Gly Leu Glu Leu
1175                1180                1185

Pro Glu Leu Leu Pro Asp Lys Leu Ala Gly Ile Lys Arg Ile Ser
1190                1195                1200

Arg Arg Ala Met Ser Ala Pro Ser Ser Gly Ser Ser Lys Val His
1205                1210                1215

Ala Val Glu Gln Gln Glu Ile Leu Asp Glu Ala Phe Gly
1220                1225                1230

<210> SEQ ID NO 47
<211> LENGTH: 3696
<212> TYPE: DNA
<213> ORGANISM: Artificial
<220> FEATURE:
<223> OTHER INFORMATION: Mycobacterium tuberculosis -ketoglutarate
      decarboxylase Kgd codon optimised gene

<400> SEQUENCE: 47

```
atggctaata tctcctctcc gtttggtcag aatgaatggc tggtagaaga aatgtaccgt     60
aaattccgcg atgacccgtc ctctgtggac ccgtcctggc atgaattcct ggtagactac    120
agcccggagc cgaccagcca accggcagcg gaaccaaccc gcgttacttc tccgctggta    180
gcggaacgtg cagctgctgc cgcgcctcag gcgccgccta accggcgga tactgccgca    240
gccggtaacg gtgtggtggc cgcactggct gctaagactg cggttccgcc gccagcagaa    300
ggcgatgaag ttgcagtcct gcgcggtgcg cgggctgcag tggtgaaaaa catgagcgcg    360
tccctggagg taccgaccgc cacgagcgtg cgcgcggtcc ctgctaaact gctgattgat    420
aaccgtattg tgatcaacaa ccagctgaaa cgtacccgtg gtgcaagat ctccttcact    480
catctgctgg gttatgcact ggtacaagcg gttaagaaat ccctaacat gaaccgtcat    540
tacactgagg tcgacggtaa accgacggct gttactccgg cacacacgaa cctgggcctg    600
gcgatcgacc tgcaaggtaa agatggtaag cgctccctgg tagttgcggg tattaaacgt    660
tgcgaaacca tgcgtttcgc acaattcgta accgcctacg aggacattgt ccgccgtgct    720
cgtgatggca aactgaccac cgaagatttt gcgggcgtta ctattagcct gaccaaccca    780
ggcaccatcg cgaccgtgca cagcgtacct cgtctgatgc gggccaaggt gcgattatc    840
ggtgtgggtg ccatggagta cccggcagaa tttcagggtg cttctgaaga gcgcatcgcc    900
gagctgggta ttggtaaact gatcaccctg acttctacct atgaccaccg catcattcag    960
```

```
ggcgcagaat ccggtgactt cctgcgcact attcacgaac tgctgctgtc cgacggtttc    1020
tgggatgaag tttttcgtga actgagcatc ccatatctgc cagttcgctg gtccaccgac    1080
aatccggact ctatcgttga caaaaacgct cgcgtaatga acctgatcgc tgcttatcgt    1140
aatcgtggtc acctgatggc tgatacggat ccgctgcgcc tggataaagc tcgtttccgt    1200
tcccacccgg acctggaagt gctgacccat ggtctgactc tgtgggatct ggaccgcgtg    1260
ttcaaagtag atggtttcgc gggtgctcag tacaagaagc tgccgtgacgt gctgggtctg    1320 ctgcgtgatg cgtactgtcg tcacattggt gtggagtacg cccacattct ggatccggaa    1380
cagaaagaat ggctggagca gcgtgtcgag accaaacacg taaaaccgac cgtagcgcag    1440
cagaaatata tcctgtccaa actgaacgcc gccgaggctt tcgaaacttt cctgcagacc    1500
aagtacgtgg gccagaaacg cttcagcctg gagggtgcgg aaagcgttat tccgatgatg    1560
gatgcagcta tcgatcagtg cgcggaacat ggtctggatg aagtcgttat cggtatgccg    1620
caccgtggtc gcctgaacgt actggcaaac atcgtcggta aaccatattc tcagatcttc    1680
acggaattcg agggcaacct gaacccgtcc caagcccacg gctccggcga cgtaaaatat    1740
catctgggtg ctaccggcct gtatctgcag atgttcggtg ataacgacat ccaggtatct    1800
ctgactgcta acccgagcca cctggaggcg gttgatcctg ttctggaagg tctggttcgc    1860
gccaaacagg atctgctgga ccacggctct atcgacagcg atggccagcg tgcattcagc    1920
gttgtaccgc tgatgctgca tggcgacgcg gcgttcgccg gtcagggtgt cgtagcagaa    1980
actctgaacc tggcgaacct gcctggctat cgcgtgggtg gcaccattca catcatcgtt    2040
aacaaccaaa tcggtttcac cacggcaccg gagtatagcc gttctagcga atattgcacc    2100
gacgtagcca aaatgatcgg tgcgccgatc ttccatgtaa acggtgacga tccagaggcc    2160
tgcgtgtggg tggctcgtct ggccgtagac ttccgccagc gttttaagaa agatgtggtt    2220
atcgacatgc tgtgctaccg ccgtcgtggt cacaacgaag gtgatgatcc gtctatgact    2280
aacccgtatg tctatgacgt ggtggacacc aagcgtggtg cacgcaaatc ttacacggag    2340
gccctgatcg tcgtggcga catctctatg aaagaagcgg aagacgctct gcgtgattac    2400
cagggtcagc tggaacgtgt gttcaatgag gtgcgtgagc tggaaaagca cggcgtacaa    2460
ccgtccgaat ccgtagagtc cgatcagatg atccctgctg gtctggcaac tgctgttgat    2520
aaaagcctgc tggcgcgtat cggcgacgca ttcctggcgc tgccgaatgg ctttaccgcg    2580
cacccgcgcg tacagccggt actgaaaaaa cgtcgtgaaa tggcctacga aggtaaaatc    2640
gattgggcct tcggtgagct gctggccctg ggctctctgg tggctgaggg caagctggta    2700
cgcctgagcg gccaggactc ccgtcgcggc acttttctc agcgtcacag cgtcctgatc    2760
gatcgtcaca ccggcgaaga attcacgccg ctgcaactgc tggctactaa ctccgatggt    2820
agcccgaccg gtggtaagtt cctggtgtac gattccccgc tgtccgaata tgctgcagtt    2880
ggtttcgagt atggttacac cgttggcaac ccggacgcag tggttctgtg ggaagcgcag    2940
ttcggcgatt tcgttaacgg tgcccagtcc attatcgatg agtttattag cagcggcgag    3000
gccaaatggg gccagctgtc taacgttgtg ctgctgctgc ctcacggcca cgagggtcaa    3060
ggcccggacc acacctccgc ccgtatcgaa cgcttcctgc agctgtgggc tgaaggctct    3120
atgaccatcg cgatgccgtc taccccaagc aactacttcc acctgctgcg tcgccacgca    3180
ctggacggca ttcagcgccc gctgatcgtt ttcacccca aatccatgct gcgccacaaa    3240
gcagctgttt ctgaaatcaa agattttacg gaaattaaat ccgttctgt gctggaagaa    3300 ccaacctacg aagacggtat tggcgaccgc aacaaggtaa gccgtatcct gctgacctcc    3360
```

```
ggcaaactgt actacgagct ggcagcacgt aaggcaaaag ataaccgcaa cgacctggcc    3420
atcgtccgcc tggaacagct ggcgccactg ccacgccgtc gcctgcgtga aaccctggat    3480
cgctacgaaa acgtaaaaga attcttctgg gtgcaggaag aaccggcaaa ccagggtgcg    3540
tggccgcgct ttggtctgga actgccggaa ctgctgccgg ataaactggc aggtatcaag    3600
cgcatcagcc gtcgcgctat gagcgccccg tcttctggta gctctaaagt acacgctgta    3660
gaacagcaag agatcctgga tgaggccttc ggctaa                              3696

<210> SEQ ID NO 48
<211> LENGTH: 74
<212> TYPE: DNA
<213> ORGANISM: Artificial sequence
<220> FEATURE:
<223> OTHER INFORMATION: Forward primer for amplification of Bacillus
      subtilis aminotransferase x

<400> SEQUENCE: 48
ggggacaagt ttgtacaaaa aagcaggcta ggaggaatta accatgaagg ttttagtcaa    60
tggccggctg attg                                                      74

<210> SEQ ID NO 49
<211> LENGTH: 62
<212> TYPE: DNA
<213> ORGANISM: Artificial sequence
<220> FEATURE:
<223> OTHER INFORMATION: Reverse primer for amplification of Bacillus
      subtilis aminotransferase x

<400> SEQUENCE: 49
ggggaccact ttgtacaaga aagctgggtt tatgaaatgc tagcagcctg ttgaatgctt    60
tc                                                                   62

<210> SEQ ID NO 50
<211> LENGTH: 82
<212> TYPE: DNA
<213> ORGANISM: Artificial sequence
<220> FEATURE:
<223> OTHER INFORMATION: Forward primer for amplification of Bacillus
      subtilis aminotransferase y

<400> SEQUENCE: 50
ggggacaagt ttgtacaaaa aagcaggcta ggaggaatta accatgactc atgatttgat    60
agaaaaaagt aaaaagcacc tc                                             82

<210> SEQ ID NO 51
<211> LENGTH: 57
<212> TYPE: DNA
<213> ORGANISM: Artificial sequence
<220> FEATURE:
<223> OTHER INFORMATION: Reverse primer for amplification of Bacillus
      subtilis aminotransferase y

<400> SEQUENCE: 51
ggggaccact ttgtacaaga aagctgggtt caatcttcaa ggctcgtaac ctcgtgg       57

<210> SEQ ID NO 52
<211> LENGTH: 64
<212> TYPE: DNA
<213> ORGANISM: Artificial sequence
<220> FEATURE:
<223> OTHER INFORMATION: Forward primer for amplification of Rhodobacter
      sphaeroides aminotransferase
```

-continued

<400> SEQUENCE: 52 gggacaagt tgtacaaaa aagcaggcta ggaggaatta accatgcccg gttgcggggg    60
cttg                                                              64

<210> SEQ ID NO 53
<211> LENGTH: 51
<212> TYPE: DNA
<213> ORGANISM: Artificial sequence
<220> FEATURE:
<223> OTHER INFORMATION: Reverse primer for amplification of Rhodobacter
      sphaeroides aminotransferase

<400> SEQUENCE: 53
ggggaccact ttgtacaaga aagctgggtt cagacggcgg ccggttcttt c            51

<210> SEQ ID NO 54
<211> LENGTH: 78
<212> TYPE: DNA
<213> ORGANISM: Artificial sequence
<220> FEATURE:
<223> OTHER INFORMATION: Forward primer for amplification of Legionella
      pneumophila aminotransferase

<400> SEQUENCE: 54
ggggacaagt ttgtacaaaa aagcaggcta ggaggaatta accatgagta tcgcatttgt    60
taacggcaag tattgttg                                                  78

<210> SEQ ID NO 55
<211> LENGTH: 67
<212> TYPE: DNA
<213> ORGANISM: Artificial sequence
<220> FEATURE:
<223> OTHER INFORMATION: Reverse primer for amplification of Legionella
      pneumophila aminotransferase

<400> SEQUENCE: 55
ggggaccact ttgtacaaga aagctgggtt tagtttacta gttgttggta ggaatcatta    60
attatcc                                                              67

<210> SEQ ID NO 56
<211> LENGTH: 76
<212> TYPE: DNA
<213> ORGANISM: Artificial sequence
<220> FEATURE:
<223> OTHER INFORMATION: Forward primer for amplification of
      Nitrosomonas europaea aminotransferase

<400> SEQUENCE: 56
ggggacaagt ttgtacaaaa aagcaggcta ggaggaatta accatgattt acctcaatgg    60
caaatttctg ccgatg                                                    76

<210> SEQ ID NO 57
<211> LENGTH: 50
<212> TYPE: DNA
<213> ORGANISM: Artificial sequence
<220> FEATURE:
<223> OTHER INFORMATION: Reverse primer for amplification of
      Nitrosomonas europaea aminotransferase

<400> SEQUENCE: 57
ggggaccact ttgtacaaga aagctgggtt tactggcgtg gagcatgccc              50

<210> SEQ ID NO 58
<211> LENGTH: 79

```
<212> TYPE: DNA
<213> ORGANISM: Artificial sequence
<220> FEATURE:
<223> OTHER INFORMATION: Forward primer for amplification of Neisseria
      gonorrhoeae aminotransferase

<400> SEQUENCE: 58 gggacaagt ttgtacaaaa aagcaggcta ggaggaatta accatgagga taaatatgaa    60
ccgtaacgaa attttattc                                                79

<210> SEQ ID NO 59
<211> LENGTH: 56
<212> TYPE: DNA
<213> ORGANISM: Artificial sequence
<220> FEATURE:
<223> OTHER INFORMATION: Reverse primer for amplification of Neisseria
      gonorrhoeae aminotransferase

<400> SEQUENCE: 59
ggggaccact ttgtacaaga aagctgggtt catgcagcca tcgccttgaa cacttc        56

<210> SEQ ID NO 60
<211> LENGTH: 66
<212> TYPE: DNA
<213> ORGANISM: Artificial sequence
<220> FEATURE:
<223> OTHER INFORMATION: Forward primer for amplification of Pseudomonas
      aeruginosa aminotransferase

<400> SEQUENCE: 60
ggggacaagt ttgtacaaaa aagcaggcta ggaggaatta accatgtcga tggccgatcg    60
tgatgg                                                               66

<210> SEQ ID NO 61
<211> LENGTH: 53
<212> TYPE: DNA
<213> ORGANISM: Artificial sequence
<220> FEATURE:
<223> OTHER INFORMATION: Reverse primer for amplification of Pseudomonas
      aeruginosa aminotransferase

<400> SEQUENCE: 61
ggggaccact ttgtacaaga aagctgggtt tacttgacca gggtacgcca ctc           53

<210> SEQ ID NO 62
<211> LENGTH: 67
<212> TYPE: DNA
<213> ORGANISM: Artificial sequence
<220> FEATURE:
<223> OTHER INFORMATION: Forward primer for amplification of
      Rhodopseudomonas palustris aminotransferase

<400> SEQUENCE: 62
ggggacaagt ttgtacaaaa aagcaggcta ggaggaatta accatgaagc tgataccgtg    60
ccgcgcc                                                              67

<210> SEQ ID NO 63
<211> LENGTH: 51
<212> TYPE: DNA
<213> ORGANISM: Artificial sequence
<220> FEATURE:
<223> OTHER INFORMATION: Reverse primer for amplification of
      Rhodopseudomonas palustris aminotransferase

<400> SEQUENCE: 63
ggggaccact ttgtacaaga aagctgggtt caggcgaccg cgcggatcac c             51
```

<210> SEQ ID NO 64
<211> LENGTH: 1353
<212> TYPE: DNA
<213> ORGANISM: Bacillus subtilis

<400> SEQUENCE: 64

| | | |
|---|---|---|
| atggagatga tgggatgga aaacattcag caaaatcagg gattaaagca aaaagatgag | 60 |
| caatttgtgt ggcatgccat gaagggagcg catcaagcgg acagcctgat agcccagaag | 120 |
| gccgaagggg cctgggtaac cgacacagac ggacgccgct atttggatgc gatgtccggt | 180 |
| ttgtggtgcg tcaacattgg ttacggcaga aaggagcttg cggaggctgc ctatgagcaa | 240 |
| ctaaaggagc tgccttacta cccgttaacg caaagtcacg cacccgcaat tcaactggcg | 300 |
| gaaaagctga atgaatggct tggcggcgat tatgttattt ttttttccaa cagcggatcg | 360 |
| gaagcaaacg aaactgcttt taaaattgcc cgccagtacc atctgcaaaa cggcgaccac | 420 |
| agccgttata aattcatctc aagatatcgg gcataccacg caatacatt gggagcgctc | 480 |
| tcagctaccg gacaggcgca gcggaaatat aaatacgagc ctttgagcca agggttcctg | 540 |
| catgcagctc cgccagatat ataccggaat cctgatgatg cagacacgct tgaaagcgca | 600 |
| aatgaaatcg accgcatcat gacatgggaa ttaagcgaaa cgattgccgg ggtcattatg | 660 |
| gagcccatca ttacaggcgg aggcatccta atgccgccgg acggatatat gaagaaggtg | 720 |
| gaggacattt gccggcgcca cggagcccctt ttgatttgcg atgaagtgat ctgcgggttt | 780 |
| ggacggacag gtgagccgtt cgggtttatg cactacggtg tgaagcctga tatcattacg | 840 |
| atggcaaagg gaatcacaag cgcgtatctg ccattgtcag cgactgctgt gaaacgggac | 900 |
| attttcgaag cgtatcaggg ggaagctcct tatgaccgtt ccgccacgt gaacacgttc | 960 |
| ggcggaagcc cggctgcctg tgctttggcg ttgaaaaacc tgcaaattat ggaggacgaa | 1020 |
| cagctgattc agcgatcccg tgatcttgga gcaaagcttt taggtgagct tcaagctctg | 1080 |
| agagaacacc cggcagtcgg ggatgttaga ggaaagggc tgctgatcgg aatcgaactc | 1140 |
| gtcaaagaca aattgactaa agagccggct gatgccgcca agtaaaacca agtggttgcg | 1200 |
| gcgtgcaaag aaaaagggct gatcatcggc aaaaacggcg atacagtcgc cggctacaac | 1260 |
| aatgtcatcc acgttgcgcc gccattttgc ctgacagaag aggacctttc ctttatcgtg | 1320 |
| aaaacggtga agaaagctt tcaaacgata taa | 1353 |

<210> SEQ ID NO 65
<211> LENGTH: 450
<212> TYPE: PRT
<213> ORGANISM: Bacillus subtilis

<400> SEQUENCE: 65

Met Glu Met Met Gly Met Glu Asn Ile Gln Gln Asn Gln Gly Leu Lys
1               5                   10                  15

Gln Lys Asp Glu Gln Phe Val Trp His Ala Met Lys Gly Ala His Gln
            20                  25                  30

Ala Asp Ser Leu Ile Ala Gln Lys Ala Glu Gly Ala Trp Val Thr Asp
        35                  40                  45

Thr Asp Gly Arg Arg Tyr Leu Asp Ala Met Ser Gly Leu Trp Cys Val
    50                  55                  60

Asn Ile Gly Tyr Gly Arg Lys Glu Leu Ala Glu Ala Ala Tyr Glu Gln
65                  70                  75                  80

Leu Lys Glu Leu Pro Tyr Tyr Pro Leu Thr Gln Ser His Ala Pro Ala
                85                  90                  95

```
Ile Gln Leu Ala Glu Lys Leu Asn Glu Trp Leu Gly Gly Asp Tyr Val
        100                 105                 110
Ile Phe Phe Ser Asn Ser Gly Ser Glu Ala Asn Glu Thr Ala Phe Lys
        115                 120                 125
Ile Ala Arg Gln Tyr His Leu Gln Asn Gly Asp His Ser Arg Tyr Lys
        130                 135                 140
Phe Ile Ser Arg Tyr Arg Ala Tyr His Gly Asn Thr Leu Gly Ala Leu
145                 150                 155                 160
Ser Ala Thr Gly Gln Ala Gln Arg Lys Tyr Lys Tyr Glu Pro Leu Ser
                165                 170                 175
Gln Gly Phe Leu His Ala Ala Pro Pro Asp Ile Tyr Arg Asn Pro Asp
            180                 185                 190
Asp Ala Asp Thr Leu Glu Ser Ala Asn Glu Ile Asp Arg Ile Met Thr
        195                 200                 205
Trp Glu Leu Ser Glu Thr Ile Ala Gly Val Ile Met Glu Pro Ile Ile
210                 215                 220
Thr Gly Gly Gly Ile Leu Met Pro Pro Asp Gly Tyr Met Lys Lys Val
225                 230                 235                 240
Glu Asp Ile Cys Arg Arg His Gly Ala Leu Leu Ile Cys Asp Glu Val
                245                 250                 255
Ile Cys Gly Phe Gly Arg Thr Gly Glu Pro Phe Gly Phe Met His Tyr
            260                 265                 270
Gly Val Lys Pro Asp Ile Ile Thr Met Ala Lys Gly Ile Thr Ser Ala
        275                 280                 285
Tyr Leu Pro Leu Ser Ala Thr Ala Val Lys Arg Asp Ile Phe Glu Ala
290                 295                 300
Tyr Gln Gly Glu Ala Pro Tyr Asp Arg Phe Arg His Val Asn Thr Phe
305                 310                 315                 320
Gly Gly Ser Pro Ala Ala Cys Ala Leu Ala Leu Lys Asn Leu Gln Ile
                325                 330                 335
Met Glu Asp Glu Gln Leu Ile Gln Arg Ser Arg Asp Leu Gly Ala Lys
            340                 345                 350
Leu Leu Gly Glu Leu Gln Ala Leu Arg Glu His Pro Ala Val Gly Asp
        355                 360                 365
Val Arg Gly Lys Gly Leu Leu Ile Gly Ile Glu Leu Val Lys Asp Lys
370                 375                 380
Leu Thr Lys Glu Pro Ala Asp Ala Ala Lys Val Asn Gln Val Val Ala
385                 390                 395                 400
Ala Cys Lys Glu Lys Gly Leu Ile Ile Gly Lys Asn Gly Asp Thr Val
                405                 410                 415
Ala Gly Tyr Asn Asn Val Ile His Val Ala Pro Pro Phe Cys Leu Thr
            420                 425                 430
Glu Glu Asp Leu Ser Phe Ile Val Lys Thr Val Lys Glu Ser Phe Gln
        435                 440                 445
Thr Ile
    450

<210> SEQ ID NO 66
<211> LENGTH: 1407
<212> TYPE: DNA
<213> ORGANISM: Pseudomonas aeruginosa

<400> SEQUENCE: 66
atgaacgcaa gactgcacgc cacgtccccc ctcggcgacg ccgacctggt ccgtgccgac      60
```

-continued

```
caggcccact acatgcacgg ctaccacgtg ttcgacgacc accgcgtcaa cggctcgctg      120
aacatcgccg ccggcgacgg cgcctatatc tacgacaccg ccggcaaccg ctacctcgac      180
gcggtgggcg gcatgtggtg caccaacatc ggcctggggc gcgaggaaat ggctcgcacc      240
gtggccgagc agaccgcct gctggcctat tccaatccct tctgcgacat ggccaacccg       300
cgcgccatcg aactctgccg caagctcgcc gagctggccc ccggcgacct cgaccacgtg      360
ttcctcacca ccgcggttc caccgccgtg acaccgcga tccgcctcat gcactactac        420
cagaactgcc gcggcaagcg cgccaagaag cacgtcatca cgcggatcaa cgcctaccac     480
ggctcgacct tcctcggcat gtcgctgggc ggcaagagcg ccgaccggcc ggccgagttc      540
gacttcctcg acgagcgcat ccaccacctc gcctgtccct attactaccg cgctccggaa      600
gggctgggcg aagccgagtt cctcgatggc ctggtggacg agttcgaacg caagatcctc      660
gaactgggcg ccgaccgggt gggggcgttc atctccgagc cggtgttcgg ctccggcggc      720
gtgatcgtcc cgcccgcggg ctaccacagg cggatgtggg agctgtgcca gcgctacgac      780
gtgctgtaca tctccgacga agtggtgacc tccttcggcc gcctcggcca cttcttcgcc      840
agccaggcgg tgttcggcgt acagccggac atcatcctca ccgccaaggg cctcacctcc      900
ggctaccagc cgctgggcgc gtgcatcttc tcccggcgca tctgggaggt gatcgccgag     960
ccggacaagg gccgctgctt cagccatggt ttcacctact ccggccaccc ggtggcctgc      1020
gcggcggcgc tgaagaacat cgagatcatc gagcgcgagg gcttgctcgc ccacgccgac     1080
gaggtcggcc gctacttcga ggagcgcctg caaagcctcc gcgacctgcc catcgtcggc      1140
gacgtgcgcg ggatgcgctt catggcctgt gtcgagttcg tcgccgacaa ggcgagcaag     1200
gcgctgtttc cggaaagcct gaacatcggc gagtgggtcc acctgcgggc gcagaagcgc     1260
ggcctgctgg ttcgtccgat cgtccacctg aacgtgatgt cgccgccgct gatcctcacc     1320
cgcgaacagg tcgataccgt ggtccgggtg ctgcgcgaga gcatcgagga aaccgtggag     1380
gatcttgtcc gcgccggtca ccggtaa                                         1407
```

<210> SEQ ID NO 67
<211> LENGTH: 468
<212> TYPE: PRT
<213> ORGANISM: Pseudomonas aeruginosa

<400> SEQUENCE: 67

```
Met Asn Ala Arg Leu His Ala Thr Ser Pro Leu Gly Asp Ala Asp Leu
1               5                  10                  15

Val Arg Ala Asp Gln Ala His Tyr Met His Gly Tyr His Val Phe Asp
            20                  25                  30

Asp His Arg Val Asn Gly Ser Leu Asn Ile Ala Ala Gly Asp Gly Ala
        35                  40                  45

Tyr Ile Tyr Asp Thr Ala Gly Asn Arg Tyr Leu Asp Ala Val Gly Gly
    50                  55                  60

Met Trp Cys Thr Asn Ile Gly Leu Gly Arg Glu Glu Met Ala Arg Thr
65                  70                  75                  80

Val Ala Glu Gln Thr Arg Leu Leu Ala Tyr Ser Asn Pro Phe Cys Asp
                85                  90                  95

Met Ala Asn Pro Arg Ala Ile Glu Leu Cys Arg Lys Leu Ala Glu Leu
            100                 105                 110

Ala Pro Gly Asp Leu Asp His Val Phe Leu Thr Thr Gly Gly Ser Thr
        115                 120                 125

Ala Val Asp Thr Ala Ile Arg Leu Met His Tyr Tyr Gln Asn Cys Arg
    130                 135                 140
```

```
Gly Lys Arg Ala Lys Lys His Val Ile Thr Arg Ile Asn Ala Tyr His
145                 150                 155                 160

Gly Ser Thr Phe Leu Gly Met Ser Leu Gly Lys Ser Ala Asp Arg
            165                 170                 175

Pro Ala Glu Phe Asp Phe Leu Asp Glu Arg Ile His His Leu Ala Cys
            180                 185                 190

Pro Tyr Tyr Tyr Arg Ala Pro Glu Gly Leu Gly Glu Ala Glu Phe Leu
            195                 200                 205

Asp Gly Leu Val Asp Glu Phe Glu Arg Lys Ile Leu Glu Leu Gly Ala
    210                 215                 220

Asp Arg Val Gly Ala Phe Ile Ser Glu Pro Val Phe Gly Ser Gly Gly
225                 230                 235                 240

Val Ile Val Pro Pro Ala Gly Tyr His Arg Arg Met Trp Glu Leu Cys
            245                 250                 255

Gln Arg Tyr Asp Val Leu Tyr Ile Ser Asp Glu Val Val Thr Ser Phe
            260                 265                 270

Gly Arg Leu Gly His Phe Phe Ala Ser Gln Ala Val Phe Gly Val Gln
            275                 280                 285

Pro Asp Ile Ile Leu Thr Ala Lys Gly Leu Thr Ser Gly Tyr Gln Pro
    290                 295                 300

Leu Gly Ala Cys Ile Phe Ser Arg Arg Ile Trp Glu Val Ile Ala Glu
305                 310                 315                 320

Pro Asp Lys Gly Arg Cys Phe Ser His Gly Phe Thr Tyr Ser Gly His
            325                 330                 335

Pro Val Ala Cys Ala Ala Ala Leu Lys Asn Ile Glu Ile Ile Glu Arg
            340                 345                 350

Glu Gly Leu Leu Ala His Ala Asp Glu Val Gly Arg Tyr Phe Glu Glu
            355                 360                 365

Arg Leu Gln Ser Leu Arg Asp Leu Pro Ile Val Gly Asp Val Arg Gly
    370                 375                 380

Met Arg Phe Met Ala Cys Val Glu Phe Val Ala Asp Lys Ala Ser Lys
385                 390                 395                 400

Ala Leu Phe Pro Glu Ser Leu Asn Ile Gly Glu Trp Val His Leu Arg
            405                 410                 415

Ala Gln Lys Arg Gly Leu Leu Val Arg Pro Ile Val His Leu Asn Val
            420                 425                 430

Met Ser Pro Pro Leu Ile Leu Thr Arg Glu Gln Val Asp Thr Val Val
            435                 440                 445

Arg Val Leu Arg Glu Ser Ile Glu Glu Thr Val Glu Asp Leu Val Arg
    450                 455                 460

Ala Gly His Arg
465

<210> SEQ ID NO 68
<211> LENGTH: 1335
<212> TYPE: DNA
<213> ORGANISM: Pseudomonas aeruginosa

<400> SEQUENCE: 68
atgacaatga atgacgagcc gcagtcgagc agcctcgaca acttctggat gcccttcacc      60
gccaaccgcc agttcaaggc gcggccgcgc ctgctggaaa gcgccgaagg catccactat     120
atcgcccagg gcgggcgccg catcctcgac ggcaccgccg gcctctggtg ctgcaatgcc     180
ggccacggcc ggcgcgagat cagcgaagcg gtggcccggc agatcgccac cctcgactac     240
```

```
gccccgccgt tccagatggg tcacccgctg ccgttcgaac tcgccgcgcg gctgacggaa      300
atcgccccgc cgagcctgaa caaagtattc ttcaccaact ccggctcgga atcggcggac      360
accgcgctga agatcgccct tgcctaccag cgcgccatcg gccagggcac ccgcacccgc      420
ctgatcggcc gcgaactggg ctaccacggg gtcggcttcg gcggcctgtc ggtaggcggt      480
atggtcaaca accgcaaggc cttctccgcc aacctgctgc cggggggtcga ccacctgccg      540 cacaccctgg acgtcgcccg caacgccttc ccgtcggcc tgcccgagca tggcgtggaa       600
aaggccgagg agctggaacg cctggtgacc ctgcacggcg ccgagaatat cgccgcggtg      660
atcgtcgagc cgatgtccgg ctcggccggc gtggtgctgc cgcccaaggg ctaccttcag      720
cggctgcgcg agataacccg caagcatggc atcctgctga tcttcgacga agtgatcacc      780
ggtttcggcc gcgtcggcga agccttcgcc gcgcagcgct ggggcgtcgt cccggacctg      840
ctgacctgcg ccaaggggct gaccaacggc agcatcccga tgggcgccgt attcgtcgac      900
gagaagatcc atgctgcctt catgcaaggc ccgcagggcg ccatcgagtt cttccacggc      960
tatacctatt ccggccatcc ggtagcctgc gccgccgccc tggcgacccct ggacatctac    1020 cgtcgcgacg acctgttcca gcgggccgtc gaactggaag gctactggca ggacgcgctg     1080
ttcagcctgc gcgacctgcc caacgtggtc gacatccgcg ccgtaggcct ggtcggcggc     1140
gtgcaactgg cgccgcacgc ggacggcccc ggcaagcgcg gctacgacgt cttcgagcgc     1200
tgcttctggg agcacgacct gatggtccgg gtgaccggcg acatcatcgc catgtcgccg     1260
ccgctgatca tcgacaagcc ccacatcgac cagatcgtcg agcgcctggc ccaggccatc     1320
cgcgccagcg tctga                                                      1335
```

<210> SEQ ID NO 69
<211> LENGTH: 444
<212> TYPE: PRT
<213> ORGANISM: Pseudomonas aeruginosa

<400> SEQUENCE: 69

```
Met Thr Met Asn Asp Glu Pro Gln Ser Ser Leu Asp Asn Phe Trp
 1               5                  10                  15

Met Pro Phe Thr Ala Asn Arg Gln Phe Lys Ala Arg Pro Arg Leu Leu
             20                  25                  30

Glu Ser Ala Glu Gly Ile His Tyr Ile Ala Gln Gly Gly Arg Arg Ile
         35                  40                  45

Leu Asp Gly Thr Ala Gly Leu Trp Cys Cys Asn Ala Gly His Gly Arg
     50                  55                  60

Arg Glu Ile Ser Glu Ala Val Ala Arg Gln Ile Ala Thr Leu Asp Tyr
 65                  70                  75                  80

Ala Pro Pro Phe Gln Met Gly His Pro Leu Pro Phe Glu Leu Ala Ala
                 85                  90                  95

Arg Leu Thr Glu Ile Ala Pro Pro Ser Leu Asn Lys Val Phe Phe Thr
            100                 105                 110

Asn Ser Gly Ser Glu Ser Ala Asp Thr Ala Leu Lys Ile Ala Leu Ala
        115                 120                 125

Tyr Gln Arg Ala Ile Gly Gln Gly Thr Arg Thr Arg Leu Ile Gly Arg
    130                 135                 140

Glu Leu Gly Tyr His Gly Val Gly Phe Gly Gly Leu Ser Val Gly Gly
145                 150                 155                 160

Met Val Asn Asn Arg Lys Ala Phe Ser Ala Asn Leu Leu Pro Gly Val
                165                 170                 175

Asp His Leu Pro His Thr Leu Asp Val Ala Arg Asn Ala Phe Thr Val
```

```
                    180                 185                 190
Gly Leu Pro Glu His Gly Val Glu Lys Ala Glu Leu Glu Arg Leu
            195                 200                 205
Val Thr Leu His Gly Ala Glu Asn Ile Ala Ala Val Ile Val Glu Pro
        210                 215                 220
Met Ser Gly Ser Ala Gly Val Val Leu Pro Pro Lys Gly Tyr Leu Gln
225                 230                 235                 240
Arg Leu Arg Glu Ile Thr Arg Lys His Gly Ile Leu Leu Ile Phe Asp
                245                 250                 255
Glu Val Ile Thr Gly Phe Gly Arg Val Gly Glu Ala Phe Ala Ala Gln
            260                 265                 270
Arg Trp Gly Val Val Pro Asp Leu Leu Thr Cys Ala Lys Gly Leu Thr
        275                 280                 285
Asn Gly Ser Ile Pro Met Gly Ala Val Phe Val Asp Glu Lys Ile His
        290                 295                 300
Ala Ala Phe Met Gln Gly Pro Gln Gly Ala Ile Glu Phe Phe His Gly
305                 310                 315                 320
Tyr Thr Tyr Ser Gly His Pro Val Ala Cys Ala Ala Ala Leu Ala Thr
                325                 330                 335
Leu Asp Ile Tyr Arg Arg Asp Asp Leu Phe Gln Arg Ala Val Glu Leu
            340                 345                 350
Glu Gly Tyr Trp Gln Asp Ala Leu Phe Ser Leu Arg Asp Leu Pro Asn
        355                 360                 365
Val Val Asp Ile Arg Ala Val Gly Leu Val Gly Gly Val Gln Leu Ala
        370                 375                 380
Pro His Ala Asp Gly Pro Gly Lys Arg Gly Tyr Asp Val Phe Glu Arg
385                 390                 395                 400
Cys Phe Trp Glu His Asp Leu Met Val Arg Val Thr Gly Asp Ile Ile
                405                 410                 415
Ala Met Ser Pro Pro Leu Ile Ile Asp Lys Pro His Ile Asp Gln Ile
            420                 425                 430
Val Glu Arg Leu Ala Gln Ala Ile Arg Ala Ser Val
        435                 440

<210> SEQ ID NO 70
<211> LENGTH: 71
<212> TYPE: DNA
<213> ORGANISM: Artificial sequence
<220> FEATURE:
<223> OTHER INFORMATION: Forward primer for amplification of Bacillus
      subtilis aminotransferase (gi16077991)

<400> SEQUENCE: 70
ggggacaagt ttgtacaaaa aagcaggcta ggaggaatta accatggaga tgatggggat         60
ggaaaacatt c                                                              71

<210> SEQ ID NO 71
<211> LENGTH: 65
<212> TYPE: DNA
<213> ORGANISM: Artificial sequence
<220> FEATURE:
<223> OTHER INFORMATION: Reverse primer for amplification of Bacillus
      subtilis aminotransferase (gi16077991)

<400> SEQUENCE: 71
ggggaccact ttgtacaaga aagctgggtt tatatcgttt gaaagctttc tttcaccgtt         60
ttcac                                                                     65
```

```
<210> SEQ ID NO 72
<211> LENGTH: 66
<212> TYPE: DNA
<213> ORGANISM: Artificial sequence
<220> FEATURE:
<223> OTHER INFORMATION: Forward primer for amplification of Pseudomonas
      aeruginosa aminotransferase (gi9951072)

<400> SEQUENCE: 72
ggggacaagt ttgtacaaaa aagcaggcta ggaggaatta accatgaacg caagactgca      60
cgccac                                                                 66

<210> SEQ ID NO 73
<211> LENGTH: 48
<212> TYPE: DNA
<213> ORGANISM: Artificial sequence
<220> FEATURE:
<223> OTHER INFORMATION: Reverse primer for amplification of Pseudomonas
      aeruginosa aminotransferase (gi9951072)

<400> SEQUENCE: 73
ggggaccact ttgtacaaga aagctgggtt taccggtgac cggcgcgg                   48

<210> SEQ ID NO 74
<211> LENGTH: 69
<212> TYPE: DNA
<213> ORGANISM: Artificial sequence
<220> FEATURE:
<223> OTHER INFORMATION: Forward primer for amplification of Pseudomonas
      aeruginosa aminotransferase (gi9951630)

<400> SEQUENCE: 74
ggggacaagt ttgtacaaaa aagcaggcta ggaggaatta accatgacaa tgaatgacga      60
gccgcagtc                                                              69

<210> SEQ ID NO 75
<211> LENGTH: 49
<212> TYPE: DNA
<213> ORGANISM: Artificial sequence
<220> FEATURE:
<223> OTHER INFORMATION: Reverse primer for amplification of Pseudomonas
      aeruginosa aminotransferase (gi9951630)

<400> SEQUENCE: 75
ggggaccact ttgtacaaga aagctgggtt cagacgctgg cgcggatgg                  49

<210> SEQ ID NO 76
<211> LENGTH: 57
<212> TYPE: DNA
<213> ORGANISM: Artificial sequence
<220> FEATURE:
<223> OTHER INFORMATION: Forward primer

<400> SEQUENCE: 76
aaatttacta gtaagaattt ttgaggaggc aatataaatg aataaaccac agtcttg         57

<210> SEQ ID NO 77
<211> LENGTH: 32
<212> TYPE: DNA
<213> ORGANISM: Artificial sequence
<220> FEATURE:
<223> OTHER INFORMATION: Reverse primer

<400> SEQUENCE: 77
aaatttggat cctacaagaa agctgggttt ac                                    32
```

```
<210> SEQ ID NO 78
<211> LENGTH: 58
<212> TYPE: DNA
<213> ORGANISM: Artificial sequence
<220> FEATURE:
<223> OTHER INFORMATION: Forward primer

<400> SEQUENCE: 78
aaatttacta gtaagaattt ttgaggaggc aatataaatg aacagccaaa tcaccaac          58

<210> SEQ ID NO 79
<211> LENGTH: 37
<212> TYPE: DNA
<213> ORGANISM: Artificial sequence
<220> FEATURE:
<223> OTHER INFORMATION: Reverse primer

<400> SEQUENCE: 79
aaatttggat ccactttgta caagaaagct gggttca                                 37

<210> SEQ ID NO 80
<211> LENGTH: 57
<212> TYPE: DNA
<213> ORGANISM: Artificial sequence
<220> FEATURE:
<223> OTHER INFORMATION: Forward primer

<400> SEQUENCE: 80
aaatttggat ccgttgagga ggcctcaaaa atgtccgaga tcactctggg caaatac           57

<210> SEQ ID NO 81
<211> LENGTH: 35
<212> TYPE: DNA
<213> ORGANISM: Artificial sequence
<220> FEATURE:
<223> OTHER INFORMATION: Reverse primer

<400> SEQUENCE: 81
aaatttggcg cgccattact gtttagcgtt agttg                                   35

<210> SEQ ID NO 82
<211> LENGTH: 52
<212> TYPE: DNA
<213> ORGANISM: Artificial sequence
<220> FEATURE:
<223> OTHER INFORMATION: Forward primer

<400> SEQUENCE: 82
aaatttggat ccgttgagga ggcctcaaaa atgtatactg ttggtgatta tc                52

<210> SEQ ID NO 83
<211> LENGTH: 37
<212> TYPE: DNA
<213> ORGANISM: Artificial sequence
<220> FEATURE:
<223> OTHER INFORMATION: Reverse primer

<400> SEQUENCE: 83
aaatttggcg cgccattact tgttctgctc cgcaaac                                 37
```

PREPARATION OF 6-AMINOCAPROIC ACID FROM 5-FORMYLVALERIC ACID

This application is the U.S. national phase of International Application No. PCT/NL2009/050117, filed 11 Mar. 2009, which designated the U.S. and claims priority to European Application No. 08152584.2, filed 11 Mar. 2008, the entire contents of each of which are hereby incorporated by reference.

The invention relates to a method for preparing 6-aminocaproic acid (hereinafter also referred to as '6-ACA'). The invention further relates to a method for preparing ε-caprolactam (hereafter referred to as 'caprolactam') from 6-ACA. The invention further relates to a host cell which may be used in the preparation of 6-ACA or caprolactam.

Caprolactam is a lactam which may be used for the production of polyamide, for instance nylon-6 or nylon-6, 12 (a copolymer of caprolactam and laurolactam). Various manners of preparing caprolactam from bulk chemicals are known in the art and include the preparation of caprolactam from cyclohexanone, toluene, phenol, cyclohexanol, benzene or cyclohexane. These intermediate compounds are generally obtained from mineral oil. In view of a growing desire to prepare materials using more sustainable technology it would be desirable to provide a method wherein caprolactam is prepared from an intermediate compound that can be obtained from a biologically renewable source or at least from an intermediate compound that is converted into caprolactam using a biochemical method. Further, it would be desirable to provide a method that requires less energy than conventional chemical processes making use of bulk chemicals from petrochemical origin.

It is known to prepare caprolactam from 6-ACA, e.g. as described in U.S. Pat. No. 6,194,572. As disclosed in WO 2005/068643, 6-ACA may be prepared biochemically by converting 6-aminohex-2-enoic acid (6-AHEA) in the presence of an enzyme having $\alpha,\beta$-enoate reductase activity. The 6-AHEA may be prepared from lysine, e.g. biochemically or by pure chemical synthesis. Although the preparation of 6-ACA via the reduction of 6-AHEA is feasible by the methods disclosed in WO 2005/068643, the inventors have found that—under the reduction reaction conditions—6-AHEA may spontaneously and substantially irreversibly cyclise to form an undesired side-product, notably β-homoproline. This cyclisation may be a bottleneck in the production of 6-ACA, and may lead to a considerable loss in yield.

It is an object of the invention to provide a novel method for preparing 6-ACA or caprolactam—which may, inter alia, be used for the preparation of polyamide—or an intermediate compound for the preparation of 6-ACA or caprolactam, that can serve as an alternative for known methods.

It is a further object to provide a novel method that would overcome one or more of the drawbacks mentioned above.

One or more further objects which may be solved in accordance with the invention, will follow from the description, below.

It has now been found possible to prepare 6-ACA from a specific starting compound, namely it has been found possible to prepare 6-aminocaproic acid (6-ACA), wherein the 6-aminocaproic acid is prepared from 2-oxo-heptanedioic acid also known as α-ketopimelic acid (AKP). In particular, the preparation may be carried out in two or more reaction steps. For instance, a method is provided wherein AKP is first converted into 5-formylpentanoate (5-formylvaleric acid, 5-FVA), which 5-FVA is converted into 6-ACA. Further a method is provided wherein AKP is first converted into alpha-aminopimelic acid (AAP). Thereafter, AAP is converted into 6-ACA.

The inventors realised that in principle, it is possible to prepare 6-ACA from AKP in an entirely chemical (i.e. without the use of a biocatalyst) manner. Examples of suitable chemical ways of carrying out individual reaction steps are given herein below. However, the inventors also realised that it is possible to prepare 6-ACA biochemically from AKP.

Accordingly, the present invention in particular relates to a method for preparing 6-ACA, wherein the 6-ACA is prepared from AKP, using at least one biocatalyst.

The invention further relates to a method, wherein 6-ACA is prepared from 5-formylpentanoate (5-formylvaleric acid, 5-FVA), using a biocatalyst. As indicated above, the 5-FVA may be obtained from AKP.

In an embodiment, 6-ACA prepared in a method of the invention is used for preparing caprolactam. Such method comprises cyclising the 6-amino-caproic acid, optionally in the presence of a biocatalyst.

When referring herein to carboxylic acids or carboxylates, e.g. 6-ACA, 2-aminoheptanedioic acid (α-aminopimelic acid, herein after abbreviated as 'AAP'), another amino acid, 5-FVA or AKP, these terms are meant to include the protonated carboxylic acid group (i.e. the neutral group), their corresponding carboxylate (their conjugated bases) as well as salts thereof. When referring herein to amino acids, e.g. 6-ACA, this term is meant to include amino acids in their zwitterionic form (in which the amino group is in the protonated and the carboxylate group is in the deprotonated form), the amino acid in which the amino group is protonated and the carboxylic group is in its neutral form, and the amino acid in which the amino group is in its neutral form and the carboxylate group is in the deprotonated form, as well as salts thereof.

In accordance with the invention, no problems have been noticed with respect to an undesired cyclisation of an intermediate product, when forming 6-ACA and optionally caprolactam, resulting in a loss of yield.

It is envisaged that a method of the invention allows a comparable or even better yield than the method described in WO 2005/68643. It is envisaged that a method of the invention may in particular be favourable if a use is made of a living organism—in particular in a method wherein growth and maintenance of the organism is taken into account.

It is further envisaged that in an embodiment of the invention the productivity of 6-ACA (g/l.h formed) in a method of the invention may be improved.

The term "or" as used herein is defined as "and/or" unless specified otherwise.

The term "a" or "an" as used herein is defined as "at least one" unless specified otherwise.

When referring to a noun (e.g. a compound, an additive, etc.) in the singular, the plural is meant to be included.

When referring to a compound of which stereoisomers exist, the compound may be any of such stereoisomers or a combination thereof. Thus, when referred to, e.g., an amino acid of which enantiomers exist, the amino acid may be the L-enantiomer, the D-enantiomer or a combination thereof. In case a natural stereoisomer exists, the compound is preferably a natural stereoisomer.

When an enzyme is mentioned with reference to an enzyme class (EC) between brackets, the enzyme class is a class wherein the enzyme is classified or may be classified, on the basis of the Enzyme Nomenclature provided by the Nomenclature Committee of the International Union of Biochemistry and Molecular Biology (NC-IUBMB), which nomenclature may be found at URL: chem[dot]qmul[dot]ac

[dot]uk[slash]iubmb[slash]enzyme[slash]. Other suitable enzymes that have not (yet) been classified in a specified class but may be classified as such, are meant to be included.

The term "homologue" is used herein in particular for polynucleotides or polypeptides having a sequence identity of at least 30%, preferably at least 40%, more preferably at least 60%, more preferably at least 65%, more preferably at least 70%, more preferably at least 75%, more preferably at least 80%, in particular at least 85%, more in particular at least 90%, at least 91%, at least 92%, at least 93%, at least 94%, at least 95%, at least 96%, at least 97%, at least 98% or at least 99%. The term homologue is also meant to include nucleic acid sequences (polynucleotide sequences) which differ from another nucleic acid sequence due to the degeneracy of the genetic code and encode the same polypeptide sequence.

Sequence identity or similarity is herein defined as a relationship between two or more polypeptide sequences or two or more nucleic acid sequences, as determined by comparing the sequences. Usually, sequence identities or similarities are compared over the whole length of the sequences, but may however also be compared only for a part of the sequences aligning with each other. In the art, "identity" or "similarity" also means the degree of sequence relatedness between polypeptide sequences or nucleic acid sequences, as the case may be, as determined by the match between such sequences. Preferred methods to determine identity or similarity are designed to give the largest match between the sequences tested. In context of this invention a preferred computer program method to determine identity and similarity between two sequences includes BLASTP and BLASTN (Altschul, S. F. et al., J. Mol. Biol. 1990, 215, 403-410, publicly available from NCBI and other sources (BLAST Manual, Altschul, S., et al., NCBI NLM NIH Bethesda, Md. 20894). Preferred parameters for polypeptide sequence comparison using BLASTP are gap open 10.0, gap extend 0.5, Blosum 62 matrix. Preferred parameters for nucleic acid sequence comparison using BLASTN are gap open 10.0, gap extend 0.5, DNA full matrix (DNA identity matrix).

In accordance with the invention, a biocatalyst is used, i.e. at least one reaction step in the method is catalysed by a biological material or moiety derived from a biological source, for instance an organism or a biomolecule derived there from. The biocatalyst may in particular comprise one or more enzymes. The biocatalyst may be used in any form. In an embodiment, one or more enzymes are used isolated from the natural environment (isolated from the organism it has been produced in), for instance as a solution, an emulsion, a dispersion, (a suspension of) freeze-dried cells, as a lysate, or immobilised on a support. In an embodiment, one or more enzymes form part of a living organism (such as living whole cells).

The enzymes may perform a catalytic function inside the cell. It is also possible that the enzyme may be secreted into a medium, wherein the cells are present.

Living cells may be growing cells, resting or dormant cells (e.g. spores) or cells in a stationary phase. It is also possible to use an enzyme forming part of a permeabilised cell (i.e. made permeable to a substrate for the enzyme or a precursor for a substrate for the enzyme or enzymes).

A biocatalyst used in a method of the invention may in principle be any organism, or be obtained or derived from any organism. The organism may be eukaryotic or prokaryotic. In particular the organism may be selected from animals (including humans), plants, bacteria, archaea, yeasts and fungi.

In an embodiment a biocatalyst originates from an animal, in particular from a part thereof—e.g. liver, pancreas, brain, kidney, heart or other organ. The animal may in particular be selected from the group of mammals, more in particular selected from the group of *Leporidae, Muridae, Suidae* and *Bovidae*.

Suitable plants in particular include plants selected from the group of *Asplenium*; Cucurbitaceae, in particular *Curcurbita*, e.g. *Curcurbita moschata* (squash), or *Cucumis; Mercurialis*, e.g. *Mercurialis perennis; Hydnocarpus*; and *Ceratonia*.

Suitable bacteria may in particular be selected amongst the group of *Vibrio, Pseudomonas, Bacillus, Corynebacterium, Brevibacterium, Enterococcus, Streptococcus, Klebsiella, Lactococcus, Lactobacillus, Clostridium, Escherichia, Thermus, Mycobacterium, Zymomonas, Proteus, Agrobacterium, Geobacillus, Acinetobacter, Ralstonia, Rhodobacter, Paracoccus, Novosphingobium, Nitrosomonas, Legionella, Neisseria, Rhodopseudomonas, Staphylococcus, Deinococcus* and *Salmonella*.

Suitable archaea may in particular be selected amongst the group of *Archaeoglobus, Aeropyrum, Halobacterium, Methanosarcina, Methanococcus, Thermoplasma, Pyrobaculum, Methanocaldococcus, Methanobacterium, Methanosphaera, Methanopyrus* and *Methanobrevibacter*.

Suitable fungi may in particular be selected amongst the group of *Rhizopus, Neurospora, Penicillium* and *Aspergillus*.

A suitable yeast may in particular be selected amongst the group of *Candida, Hansenula, Kluyveromyces* and *Saccharomyces*.

It will be clear to the person skilled in the art that use can be made of a naturally occurring biocatalyst (wild type) or a mutant of a naturally occurring biocatalyst with suitable activity in a method according to the invention. Properties of a naturally occurring biocatalyst may be improved by biological techniques known to the skilled person in the art, such as e.g. molecular evolution or rational design. Mutants of wild-type biocatalysts can for example be made by modifying the encoding DNA of an organism capable of acting as a biocatalyst or capable of producing a biocatalytic moiety (such as an enzyme) using mutagenesis techniques known to the person skilled in the art (random mutagenesis, site-directed mutagenesis, directed evolution, gene recombination, etc.). In particular the DNA may be modified such that it encodes an enzyme that differs by at least one amino acid from the wild-type enzyme, so that it encodes an enzyme that comprises one or more amino acid substitutions, deletions and/or insertions compared to the wild-type, or such that the mutants combine sequences of two or more parent enzymes or by effecting the expression of the thus modified DNA in a suitable (host) cell. The latter may be achieved by methods known to the skilled person in the art such as codon optimisation or codon pair optimisation, e.g. based on a method as described in WO 2008/000632.

A mutant biocatalyst may have improved properties, for instance with respect to one or more of the following aspects: selectivity towards the substrate, activity, stability, solvent tolerance, pH profile, temperature profile, substrate profile, susceptibility to inhibition, cofactor utilisation and substrate-affinity. Mutants with improved properties can be identified by applying e.g. suitable high through-put screening or selection methods based on such methods known to the skilled person in the art.

When referred to a biocatalyst, in particular an enzyme, from a particular source, recombinant biocatalysts, in particular enzymes, originating from a first organism, but actually produced in a (genetically modified) second organism, are specifically meant to be included as biocatalysts, in particular enzymes, from that first organism.

In a preferred method of the invention, the preparation comprises a biocatalytic (usually an enzymatic) reaction in the presence of a biocatalyst capable of catalysing the decarboxylation of an α-keto acid or an amino acid (i.e. a compound comprising at least one carboxylic acid group and at least one amino group). An enzyme having such catalytic activity may therefore be referred to as an α-keto acid decarboxylase respectively an amino acid decarboxylase.

Said acid preferably is a diacid, wherein the said biocatalyst is selective towards the acid group next to the keto- or amino-group.

In general, a suitable decarboxylase has α-ketopimelate decarboxylase activity, capable of catalysing the conversion of AKP into 5-FVA or α-aminopimelate decarboxylase activity, capable of catalysing the conversion of AAP to 6-ACA.

An enzyme capable of decarboxylating an α-keto acid or an amino acid may in particular be selected from the group of decarboxylases (E.C. 4.1.1), preferably from the group of oxaloacetate decarboxylases (EC 4.1.1.3), diaminopimelate decarboxylases (EC 4.1.1.20), branched chain α-keto acid decarboxylases (EC 4.1.1.72), α-ketoisovalerate decarboxylases, α-ketoglutarate decarboxylases (EC 4.1.1.71), and pyruvate decarboxylases (EC 4.1.1.1).

One or more other suitable decarboxylases may be selected amongst the group of oxalate decarboxylases (EC 4.1.1.2), acetoacetate decarboxylases (EC 4.1.1.4), valine decarboxylases/leucine decarboxylases (EC 4.1.1.14), glutamate decarboxylases (EC 4.1.1.15), aspartate 1-decarboxylases (EC 4.1.1.11), 3-hydroxyglutamate decarboxylases (EC 4.1.1.16), ornithine decarboxylases (EC 4.1.1.17), lysine decarboxylases (EC 4.1.1.18), arginine decarboxylases (EC 4.1.1.19), 2-oxoglutarate decarboxylases (EC 4.1.1.71), and diaminobutyrate decarboxylases (EC 4.1.1.86).

A decarboxylase may in particular be a decarboxylase of an organism selected from the group of squashes; cucumbers; yeasts; fungi, e.g. *Saccharomyces cerevisiae, Candida flareri, Hansenula* sp., *Kluyveromyces marxianus, Rhizopus javanicus*, and *Neurospora crassa*; mammals, in particular from mammalian brain; and bacteria, such as *Escherichia coli, Lactococcus lactis, Mycobacterium tuberculosis, Pseudomonas* sp. and *Zymomonas mobilis*.

The pyruvate decarboxylase may originate from *Saccharomyces cerevisiae* or *Zymomonas mobilis*. In particular, pyruvate decarboxylase mutant I472A from *Zymomonas mobilis* may be used.

Glutamate decarboxylase, diaminopimelate decarboxylase or aspartate decarboxylase from *Escherichia coli* (*E. coli*) may be used.

Glutamate decarboxylase from *Neurospora crassa, Mycobacterium leprae, Clostridium perfringens, Lactobacillus brevis, Mycobacterium tuberculosis, Streptococcus* or *Lactococcus* may be used. Examples of *Lactococcus* species from which the glutamate decarboxylase may originate in particular include *Lactococcus lactis*, such as *Lactococcus lactis* strain B1157, *Lactococcus lactis* IFPL730, more in particular *Lactococcus lactis* var. *maltigenes* (formerly named *Streptococcus lactis* var. *maltigenes*).

An oxaloacetate decarboxylase from *Pseudomonas* may in particular be used.

A branched-chain alpha-keto acid decarboxylase from *Lactococcus lactis* may be used. More in particular, an alpha-ketoisovalerate decarboxylase from *Lactococcus lactis* may be used.

An alpha-ketoglutarate decarboxylase from *Mycobacterium tuberculosis* may in particular be used.

In a preferred method of the invention, the preparation of 6-ACA comprises an enzymatic reaction in the presence of an enzyme capable of catalysing a transamination reaction in the presence of an amino donor, selected from the group of aminotransferases (E.C. 2.6.1).

In general, a suitable aminotransferase has 6-aminocaproic acid 6-aminotransferase activity, capable of catalysing the conversion of 5-FVA into 6-ACA or α-aminopimelate 2-aminotransferase activity, capable of catalysing the conversion of AKP into AAP.

The aminotransferase may in particular be selected amongst the group of β-aminoisobutyrate:α-ketoglutarate aminotransferases, β-alanine aminotransferases, aspartate aminotransferases, 4-amino-butyrate aminotransferases (EC 2.6.1.19), L-lysine 6-aminotransferase (EC 2.6.1.36), 2-aminoadipate aminotransferases (EC 2.6.1.39), 5-aminovalerate aminotransferases (EC 2.6.1.48), 2-aminohexanoate aminotransferases (EC 2.6.1.67) and lysine:pyruvate 6-aminotransferases (EC 2.6.1.71).

In an embodiment an aminotransferase may be selected amongst the group of alanine aminotransferases (EC 2.6.1.2), leucine aminotransferases (EC 2.6.1.6), alanine-oxo-acid aminotransferases (EC 2.6.1.12), β-alanine-pyruvate aminotransferases (EC 2.6.1.18), (S)-3-amino-2-methylpropionate aminotransferases (EC 2.6.1.22), L,L-diaminopimelate aminotransferase (EC 2.6.1.83).

The aminotransferase may in particular be selected amongst aminotransferases from a mammal; *Mercurialis*, in particular *Mercurialis perennis*, more in particular shoots of *Mercurialis perennis*; *Asplenium*, more in particular *Asplenium unilaterale* or *Asplenium septentrionale*; *Ceratonia*, more in particular *Ceratonia siliqua*; *Rhodobacter*, in particular *Rhodobacter sphaeroides*, *Staphylococcus*, in particular *Staphylococcus aureus*; *Vibrio*, in particular *Vibrio fluvialis*; *Pseudomonas*, in particular *Pseudomonas aeruginosa*; *Rhodopseusomonas*; *Bacillus*, in particular *Bacillus weihenstephanensis* and *Bacillus subtilis*; *Legionella*; *Nitrosomas*; *Neisseria*; or yeast, in particular *Saccharomyces cerevisiae*.

In case the enzyme is of a mammal, it may in particular originate from mammalian kidney, from mammalian liver, from mammalian heart or from mammalian brain. For instance a suitable enzyme may be selected amongst the group of β-aminoisobutyrate:α-ketoglutarate aminotransferase from mammalian kidney, in particular β-aminoisobutyrate: α-ketoglutarate aminotransferase from hog kidney; β-alanine aminotransferase from mammalian liver, in particular β-alanine aminotransferase from rabbit liver; aspartate aminotransferase from mammalian heart; in particular aspartate aminotransferase from pig heart; 4-amino-butyrate aminotransferase from mammalian liver, in particular 4-aminobutyrate aminotransferase from pig liver; 4-amino-butyrate aminotransferase from mammalian brain, in particular 4-aminobutyrate aminotransferase from human, pig, or rat brain; α-ketoadipate-glutamate aminotransferase from *Neurospora*, in particular α-ketoadipate:glutamate aminotransferase from *Neurospora crassa*; 4-amino-butyrate aminotransferase from *E. coli*, or α-aminoadipate aminotransferase from *Thermus*, in particular α-aminoadipate aminotransferase from *Thermus thermophilus*, and 5-aminovalerate aminotransferase from *Clostridium* in particular from *Clostridium aminovalericum*. A suitable 2-aminoadipate aminotransferase may e.g. be provided by *Pyrobaculum islandicum*.

In particular, the amino donor can be selected from the group of ammonia, ammonium ions, amines and amino acids. Suitable amines are primary amines and secondary amines. The amino acid may have a D- or L-configuration. Examples of amino donors are alanine, glutamate, isopropylamine, 2-aminobutane, 2-aminoheptane, phenylmethanamine, 1-phenyl-1-aminoethane, glutamine, tyrosine, phenylalanine, aspartate, β-aminoisobutyrate, β-alanine, 4-aminobutyrate, and α-aminoadipate.

In a further preferred embodiment, the method for preparing 6-ACA comprises a biocatalytic reaction in the presence of an enzyme capable of catalysing a reductive amination reaction in the presence of an ammonia source, selected from the group of oxidoreductases acting on the CH—NH$_2$ group of donors (EC 1.4), in particular from the group of amino acid dehydrogenases (E.C. 1.4.1). In general, a suitable amino acid dehydrogenase has 6-aminocaproic acid 6-dehydrogenase activity, catalysing the conversion of 5-FVA into 6-ACA or has α-aminopimelate 2-dehydrogenase activity, catalysing the conversion of AKP into AAP. In particular a suitable amino acid dehydrogenase be selected amongst the group of diaminopimelate dehydrogenases (EC 1.4.1.16), lysine 6-dehydrogenases (EC 1.4.1.18), glutamate dehydrogenases (EC 1.4.1.3; EC 1.4.1.4), and leucine dehydrogenases (EC 1.4.1.9).

In an embodiment, an amino acid dehydrogenase may be selected amongst an amino acid dehydrogenases classified as glutamate dehydrogenases acting with NAD or NADP as acceptor (EC 1.4.1.3), glutamate dehydrogenases acting with NADP as acceptor (EC 1.4.1.4), leucine dehydrogenases (EC 1.4.1.9), diaminopimelate dehydrogenases (EC 1.4.1.16), and lysine 6-dehydrogenases (EC 1.4.1.18).

An amino acid dehydrogenase may in particular originate from an organism selected from the group of *Corynebacterium*, in particular *Corynebacterium glutamicum; Proteus*, in particular *Proteus vulgaris; Agrobacterium*, in particular *Agrobacterium tumefaciens; Geobacillus*, in particular *Geobacillus stearothermophilus; Acinetobacter*, in particular *Acinetobacter* sp. ADP1; *Ralstonia*, in particular *Ralstonia solanacearum; Salmonella*, in particular *Salmonella typhimurium; Saccharomyces*, in particular *Saccharomyces cerevisiae; Brevibacterium*, in particular *Brevibacterium flavum*; and *Bacillus*, in particular *Bacillus sphaericus, Bacillus cereus* or *Bacillus subtilis*. For instance a suitable amino acid dehydrogenase may be selected amongst diaminopimelate dehydrogenases from *Bacillus*, in particular *Bacillus sphaericus*; diaminopimelate dehydrogenases from *Brevibacterium* sp.; diaminopimelate dehydrogenases from *Corynebacterium*, in particular diaminopimelate dehydrogenases from *Corynebacterium glutamicum*; diaminopimelate dehydrogenases from *Proteus*, in particular diaminopimelate dehydrogenase from *Proteus vulgaris*; lysine 6-dehydrogenases from *Agrobacterium*, in particular *Agrobacterium tumefaciens*, lysine 6-dehydrogenases from *Geobacillus*, in particular from *Geobacillus stearothermophilus*; glutamate dehydrogenases acting with NADH or NADPH as cofactor (EC 1.4.1.3) from *Acinetobacter*, in particular glutamate dehydrogenases from *Acinetobacter* sp. ADP1; glutamate dehydrogenases (EC 1.4.1.3) from *Ralstonia*, in particular glutamate dehydrogenases from *Ralstonia solanacearum*; glutamate dehydrogenases acting with NADPH as cofactor (EC 1.4.1.4) from *Salmonella*, in particular glutamate dehydrogenases from *Salmonella typhimurium*; glutamate dehydrogenases (EC 1.4.1.4) from *Saccharomyces*, in particular glutamate dehydrogenases from *Saccharomyces cerevisiae*; glutamate dehydrogenases (EC 1.4.1.4) from *Brevibacterium*, in particular glutamate dehydrogenases from *Brevibacterium flavum*; and leucine dehydrogenases from *Bacillus*, in particular leucine dehydrogenases from *Bacillus cereus* or *Bacillus subtilis*.

In a specific embodiment, AKP is biocatalytically converted into 5-formylpentanoate (5-FVA) in the presence of a decarboxylase or other biocatalyst catalysing such conversion. A decarboxylase used in accordance with the invention may in particular be selected from the group of αketo acid decarboxylases from *Lactococcus lactis, Lactococcus lactis* var. *maltigenes* or *Lactococcus lactis* subsp. *cremoris*; branched chain α-keto acid decarboxylases from *Lactococcus lactis* strain B1157 or *Lactococcus lactis* IFPL730; pyruvate decarboxylases from *Saccharomyces cerevisiae, Candida flareri, Zymomonas mobilis, Hansenula* sp., *Rhizopus javanicus, Neurospora crassa*, or *Kluyveromyces marxianus*; α-ketoglutarate decarboxylases from *Mycobacterium tuberculosis*; glutamate decarboxylases from *E. coli, Lactobacillus* brevis, *Mycobacterium leprae, Neurospora crassa* or *Clostridium perfringens*; and aspartate decarboxylases from *E. coli*.

In particular, a decarboxylase from *Escherichia coli, Zymomonas mobilis, Saccharomyces cerevisiae, Mycobacterium tuberculosis, Pseudomonas* species, or *Lactococcus lactis* has been found suitable to catalyse the conversion of AKP into 5-FVA. More in particular, a biocatalyst comprising a decarboxylase having a amino acid sequence as identified by Sequence ID 31, Sequence ID 34, Sequence ID 37, Sequence ID 40, Sequence ID 43, Sequence ID 46 or a homologue thereof may be used. It is also envisaged that such decarboxylase may be used to prepare 6-ACA from AAP.

Thereafter 5-FVA is converted into 6-ACA. This can be done chemically: 6-ACA can be prepared in high yield by reductive amination of 5-FVA with ammonia over a hydrogenation catalyst, for example Ni on SiO$_2$/Al$_2$O$_3$ support, as described for 9-aminononanoic acid (9-aminopelargonic acid) and 12-aminododecanoic acid (12-aminolauric acid) in EP-A 628 535 or DE 4 322 065.

Alternatively, 6-ACA can be obtained by hydrogenation over PtO$_2$ of 6-oximocaproic acid, prepared by reaction of 5-FVA and hydroxylamine. (see e.g. F. O. Ayorinde, E. Y. Nana, P. D. Nicely, A. S. Woods, E. O. Price, C. P. Nwaonicha *J. Am. Oil Chem. Soc.* 1997, 74, 531-538 for synthesis of the homologous 12-aminododecanoic acid).

In an embodiment, the conversion of 5-FVA to 6-ACA is performed biocatalytically in the presence of (i) an amino donor and (ii) an aminotransferase, an amino acid dehydrogenase or another biocatalyst capable of catalysing such conversion. In particular in such an embodiment the aminotransferase may be selected from the group of aminotransferases from *Vibrio fluvialis, Pseudomonas aeruginosa, Bacillus subtilis, Bacillus weihenstephanensis* or *Escherichia coli*; β-aminoisobutyrate:α-ketoglutarate aminotransferase from hog kidney; β-alanine aminotransferase from rabbit liver; aminotransferase from shoots from *Mercurialis perennis*; 4-aminobutyrate aminotransferase from pig liver or from human, rat, or pig brain; β-alanine aminotransferase from rabbit liver; and L-lysine:α-ketoglutarate-ε-aminotransferase. In case an amino acid dehydrogenase is used, such amino acid dehydrogenase may in particular be selected from the group of lysine 6-dehydrogenases from *Agrobacterium tumefaciens* or *Geobacillus stearothermophilus*. Another suitable amino acid dehydrogenase may be selected from the group of diaminopimelate dehydrogenases from *Bacillus sphaericus, Brevibacterium* sp., *Corynebacterium glutamicum*, or *Proteus vulgaris*; from the group of glutamate dehydrogenases acting with NADH or NADPH as cofactor (EC 1.4.1.3) from *Acinetobacter* sp. ADP1 or *Ralstonia solanacearum*; from the group of glutamate dehydrogenases acting with NADPH as cofactor (EC 1.4.1.4) from *Salmonella typhimurium*; from the group of glutamate dehydrogenases (EC 1.4.1.4) from *Saccharomyces cerevisiae* or *Brevibacterium flavum*; or from the group of leucine dehydrogenases from *Bacillus cereus* or *Bacillus subtilis*.

In a specific embodiment, the conversion of 5-FVA to 6-ACA is catalysed by a biocatalyst comprising an aminotransferase comprising an amino acid sequence according to Sequence ID 2, Sequence ID 5, Sequence ID 8, Sequence ID 65, Sequence ID 67, Sequence ID 69 or a homologue of any of these sequences.

In a specific embodiment, AKP is chemically converted into 5-FVA. Efficient chemical decarboxylation of a 2-keto carboxylic acid into the corresponding aldehyde can be performed by intermediate enamine formation using a secondary amine, for instance morpholine, under azeotropic water removal and simultaneous loss of $CO_2$, e.g. based on a method as described in Tetrahedron Lett. 1982, 23(4), 459-462. The intermediate terminal enamide is subsequently hydrolysed to the corresponding aldehyde. 5-FVA may thereafter be biocatalytically converted into 6-ACA by transamination in the presence of an aminotransferase or by enzymatic reductive amination by an amino acid dehydrogenase or another biocatalyst able of catalysing such conversion. Such aminotransferase or amino acid dehydrogenase may in particular be selected from the biocatalysts mentioned above when describing the conversion of 5-FVA to 6-ACA.

Alternatively, the conversion of 5-FVA to 6-ACA may be performed by a chemical method, e.g. as mentioned above.

In a specific embodiment, AKP is biocatalytically converted into AAP in the presence of (i) an aminotransferase, an amino acid dehydrogenase, or another biocatalyst capable of catalysing such conversion and (ii) an amino donor. Such aminotransferase used in accordance with the invention for the conversion of AKP to AAP may in particular be selected from aminotransferases mentioned above, more in particular from the group of aspartate aminotransferases from pig heart; α-ketoadipate:glutamate aminotransferases from *Neurospora crassa* or yeast; aminotransferases from shoots from *Mercurialis perennis;* 4-aminobutyrate aminotransferases from *E. coli*; α-aminoadipate aminotransferases from *Thermus thermophilus*; aminotransferases from *Asplenium septentrionale* or *Asplenium unilaterale*; and aminotransferases from *Ceratonia siliqua.*

In a preferred embodiment, the aminotransferase for the conversion of AKP to AAP is selected from the group of aminotransferases from *Vibrio, Pseudomonas, Bacillus, Legionella, Nitrosomonas, Neisseria, Rhodobacter, Escherichia* and *Rhodopseudomonas.*

In particular, aminotransferases from an organism selected from the group of *Bacillus subtilis, Rhodobacter sphaeroides, Legionella pneumophila, Nitrosomonas europaea, Neisseria gonorrhoeae, Pseudomonas syringae, Rhodopseudomonas palustris, Vibrio fluvialis, Escherichia coli* and *Pseudomonas aeruginosa*, have been found suitable to catalyse the conversion of AKP to AAP.

In a specific embodiment, for the conversion of AKP to AAP an aminotransferase is used comprising an amino acid sequence according to Sequence ID 2, Sequence ID 8, Sequence ID 12, Sequence ID 15, Sequence ID 17, Sequence ID 19, Sequence ID 21, Sequence ID 23, Sequence ID 25, Sequence ID 27, Sequence ID 29 or a homologue of any of these sequences.

In a further embodiment, the method for preparing AAP comprises a biocatalytic reaction in the presence of an enzyme capable of catalysing a reductive amination reaction in the presence of an ammonia source, selected from the group of oxidoreductases acting on the $CH-NH_2$ group of donors (EC 1.4), in particular from the group of amino acid dehydrogenases (E.C. 1.4.1). In general, a suitable amino acid dehydrogenase has α-aminopimelate 2-dehydrogenase activity, catalysing the conversion of AKP into AAP.

In particular a suitable amino acid dehydrogenase may be selected from the group of diaminopimelate dehydrogenases (EC 1.4.1.16), glutamate dehydrogenases (EC 1.4.1.3; EC 1.4.1.4), and leucine dehydrogenases (EC 1.4.1.9).

In an embodiment, an amino acid dehydrogenase is selected amongst amino acid dehydrogenases classified as glutamate dehydrogenases acting with NAD or NADP as acceptor (EC 1.4.1.3), glutamate dehydrogenases acting with NADP as acceptor (EC 1.4.1.4), leucine dehydrogenases (EC 1.4.1.9), and diaminopimelate dehydrogenases (EC 1.4.1.16).

An amino acid dehydrogenase may in particular originate from an organism selected from the group of *Corynebacterium*, in particular *Corynebacterium glutamicum; Proteus*, in particular *Proteus vulgaris; Agrobacterium*, in particular *Agrobacterium tumefaciens; Geobacillus*, in particular *Geobacillus stearothermophilus; Acinetobacter*, in particular *Acinetobacter* sp. ADP1; *Ralstonia*, in particular *Ralstonia solanacearum; Salmonella*, in particular *Salmonella typhimurium; Saccharomyces*, in particular *Saccharomyces cerevisiae; Brevibacterium*, in particular *Brevibacterium flavum*; and *Bacillus*, in particular *Bacillus sphaericus, Bacillus cereus* or *Bacillus subtilis.*

For instance a suitable amino acid dehydrogenase may be selected amongst diaminopimelate dehydrogenases from *Bacillus*, in particular *Bacillus sphaericus*; diaminopimelate dehydrogenases from *Brevibacterium* sp.; diaminopimelate dehydrogenases from *Corynebacterium*, in particular diaminopimelate dehydrogenases from *Corynebacterium glutamicum*; diaminopimelate dehydrogenases from *Proteus*, in particular diaminopimelate dehydrogenase from *Proteus vulgaris*; glutamate dehydrogenases acting with NADH or NADPH as cofactor (EC 1.4.1.3) from *Acinetobacter*, in particular glutamate dehydrogenases from *Acinetobacter* sp. ADP1; glutamate dehydrogenases (EC 1.4.1.3) from *Ralstonia*, in particular glutamate dehydrogenases from *Ralstonia solanacearum*; glutamate dehydrogenases acting with NADPH as cofactor (EC 1.4.1.4) from *Salmonella*, in particular glutamate dehydrogenases from *Salmonella typhimurium*; glutamate dehydrogenases (EC 1.4.1.4) from *Saccharomyces*, in particular glutamate dehydrogenases from *Saccharomyces cerevisiae*; glutamate dehydrogenases (EC 1.4.1.4) from *Brevibacterium*, in particular glutamate dehydrogenases from *Brevibacterium flavum*; and leucine dehydrogenases from *Bacillus*, in particular leucine dehydrogenases from *Bacillus cereus* or *Bacillus subtilis.*

Another suitable amino acid dehydrogenase may be selected from the group of lysine 6-dehydrogenases from *Agrobacterium tumefaciens* or *Geobacillus stearothermophilus*; or from the group of leucine dehydrogenases from *Bacillus cereus* or *Bacillus subtilis.*

AAP prepared in a method of the invention may further be used for the preparation of 6-ACA. The inventors have realised that AAP, prepared from AKP, can be converted into 6-ACA by a decarboxylation reaction. This can be performed chemically, for instance by heating in a high boiling solvent in the presence of a ketone or aldehyde catalyst. For example, amino acids are decarboxylated in good yields in cyclohexanol at 150-160° C. with 1-2 v/v % of cyclohexenone as described by M. Hashimoto, Y. Eda, Y. Osanai, T. Iwai and S. Aoki in *Chem. Lett.* 1986, 893-896. Similar methods are described in Eur. Pat. Appl. 1586553, 2005 by Daiso, and by S. D. Brandt, D. Mansell, S. Freeman, I. A. Fleet, J. F. Alder *J. Pharm. Biomed. Anal.* 2006, 41, 872-882.

Alternatively, the decarboxylation of AAP to 6-ACA may be performed biocatalytically in the presence of a decarboxylase or other biocatalyst catalysing such decarboxylation.

The decarboxylase may be selected amongst decarboxylases capable of catalysing the decarboxylation of an α-amino acid. An enzyme capable of decarboxylating an alpha-amino acid may in particular be selected from the group of decarboxylases (E.C. 4.1.1), preferably from the group of pyruvate decarboxylases (EC 4.1.1.1), diaminopimelate decarboxylases (EC 4.1.1.20), diaminopimelate decarboxylases (EC 4.1.1.20), branched chain alpha-keto acid decarboxylases (EC 4.1.1.72), which include alpha-ketoisovalerate decarboxylases, and alpha-ketoglutarate decarboxylases (EC 4.1.1.71).

One or more other suitable decarboxylases may in particular be selected amongst the group of oxalate decarboxylases (EC 4.1.1.2), oxaloacetate decarboxylases (EC 4.1.1.3), acetoacetate decarboxylases (EC 4.1.1.4), aspartate 1-decarboxylases (EC 4.1.1.11), valine decarboxylases/leucine decarboxylases (EC 4.1.1.14), glutamate decarboxylases (EC 4.1.1.15), 3-hydroxyglutamate decarboxylases (EC 4.1.1.16), ornithine decarboxylases (EC 4.1.1.17), lysine decarboxylases (EC 4.1.1.18), arginine decarboxylases (EC 4.1.1.19), 2-oxoglutarate decarboxylases (EC 4.1.1.71), and diaminobutyrate decarboxylases (EC 4.1.1.86).

A decarboxylase may in particular be a decarboxylase of an organism selected from the group of squashes, e.g. *Curcurbita moschata*; cucumbers; yeasts; fungi, e.g. *Saccharomyces cerevisiae, Candida flareri, Hansenula* sp., *Kluyveromyces marxianus, Rhizopus javanicus*, and *Neurospora crassa*; mammals, in particular from mammalian brain; and bacteria such as *Escherichia coli, Lactococcus lactis, Mycobacterium tuberculosis, Pseudomonas* sp. and *Zymomonas mobilis*.

The pyruvate decarboxylase may originate from *Saccharomyces cerevisiae* or *Zymomonas mobilis*. In particular, pyruvate decarboxylase mutant I472A from *Zymomonas mobilis* may be used. An oxaloacetate decarboxylase from *Pseudomonas* may in particular be used. Glutamate decarboxylase or aspartate decarboxylase from *Escherichia coli* (*E. coli*) may be used, or glutamate decarboxylase from *Neurospora crassa, Mycobacterium leprae, Clostridium perfringens, Lactobacillus* brevis, *Mycobacterium tuberculosis, Streptococcus* or *Lactococcus* may be used. Examples of *Lactococcus* species from which the glutamate decarboxylase may originate in particular include *Lactococcus lactis*, such as *Lactococcus lactis* strain B1157, *Lactococcus lactis* IFPL730, more in particular *Lactococcus lactis* var. *maltigenes* (formerly named *Streptococcus lactis* var. *maltigenes*). A diaminopimelate decarboxylase may, e.g., be from an organism capable of synthesising lysine from diaminopimelate. Such organism may in particular be found amongst bacteria, archaea and plants. In particular, the diaminopimelate decarboxylase may be from a gram negative bacterium, for instance *E. coli*. Branched-chain alpha-keto acid decarboxylases from *Lactococcus lactis* may be used. More in particular, branched chain alpha-keto acid decarboxylases and alpha-ketoisovalerate decarboxylases from *Lactococcus lactis* may be used.

An alpha-ketoglutarate decarboxylase from *Mycobacterium tuberculosis* may in particular be used. The inventors have found that alpha-ketoglutarate decarboxylase (Kgd) from *Mycobacterium tuberculosis* may be used for converting AAP into 6-ACA. In particular, the inventors have found that such decarboxylase comprising a sequence as shown in SEQUENCE ID No. 46 or a functional analogue thereof may be capable of catalysing the formation of 6-ACA from AAP.

A glutamate decarboxylase may in particular be selected from *Curcurbita moschata*, cucumber, yeast, or calf brain; and diaminopimelate decarboxylases (EC 4.1.1.20).

A diaminopimelate decarboxylase may, e.g., be from an organism capable of synthesising lysine from diaminopimelate. Such organism may in particular be found amongst bacteria, archaea and plants.

In particular, the diaminopimelate decarboxylase may be from a gram negative bacterium, for instance *E. coli*.

In a specific embodiment, AKP is chemically converted into AAP. AAP can be prepared from 2-oxopimelic acid by catalytic Leuckart-Wallach reaction as described for similar compounds. This reaction is performed with ammonium formate in methanol and [RhCp*Cl$_2$]$_2$ as homogeneous catalyst (M. Kitamura, D. Lee, S. Hayashi, S. Tanaka, M. Yoshimura *J. Org. Chem.* 2002, 67, 8685-8687). Alternatively, the Leuckart-Wallach reaction can be performed with aqueous ammonium formate using [Ir$^{III}$Cp*(bPY)H$_2$O]SO$_4$ as catalyst as described by S. Ogo, K. Uehara and S. Fukuzumi in *J. Am. Chem. Soc.* 2004, 126, 3020-3021. Transformation of α-keto acids into (enantiomerically enriched) amino acids is also possible by reaction with (chiral) benzylamines and subsequent hydrogenation of the intermediate imine over Pd/C or Pd(OH)$_2$/C. See for example, R. G. Hiskey, R. C. Northrop *J. Am. Chem. Soc.* 1961, 83, 4798.

Thereafter AAP is biocatalytically converted into 6-ACA, in the presence of a decarboxylase or another biocatalyst capable of performing such decarboxylation. Such decarboxylase may in particular be selected amongst the biocatalysts referred to above, when describing biocatalysts for the conversion of AAP to 6-ACA.

Alternatively, the conversion of AAP to 6-ACA may be performed by a chemical method, e.g. as mentioned above.

In a specific embodiment, AKP is biocatalytically converted into 5-FVA in the presence of a decarboxylase or other biocatalyst capable of catalysing such conversion and 5-FVA is thereafter converted into 6-ACA in the presence of an aminotransferase, amino acid dehydrogenase, or other biocatalyst capable of catalysing such conversion. Decarboxylases suitable for these reactions may in particular be selected from the group of decarboxylases mentioned above, when describing the biocatalytic conversion of AKP into 5-FVA. A suitable aminotransferase or amino acid dehydrogenase for the conversion of 5-FVA may in particular be selected from those mentioned above, when describing the biocatalytic conversion of 5-FVA to 6-ACA.

In a specific embodiment, AKP is biocatalytically converted into AAP in the presence of an aminotransferase, amino acid dehydrogenase, or other biocatalyst capable of catalysing such conversion and AAP is thereafter converted into 6-ACA in the presence of a decarboxylase or other biocatalyst capable of catalysing such conversion.

Enzymes suitable for these reactions may in particular be selected from the group of aminotransferases, amino acid dehydrogenases, and decarboxylases which have been described above when describing the biocatalytic conversion of AKP into AAP and the biocatalytic conversion of AAP into 6-ACA respectively.

AKP used to prepare 6-ACA may in principle be obtained in any way. For instance, AKP may be obtained based on a method as described by H. Jäger et al. Chem. Ber. 1959, 92, 2492-2499. AKP can be prepared by alkylating cyclopentanone with diethyl oxalate using sodium ethoxide as a base, refluxing the resultant product in a strong acid (2 M HCl) and recovering the product, e.g. by crystallisation from toluene.

It is also possible to obtain AKP from a natural source, e.g. from methanogenic *Archaea*, from *Asplenium septentrionale*, or from *Hydnocarpus anthelminthica*. AKP may for instance be extracted from such organism, or a part thereof, e.g. from *Hydnocarpus anthelminthica* seeds. A suitable extraction method may e.g. be based on the method described in A. I. Virtanen and A. M. Berg in Acta Chemica Scandinavica 1954, 6, 1085-1086, wherein the extraction of amino acids and AKP from *Asplenium*, using 70% ethanol, is described.

In a specific embodiment, AKP is prepared in a method comprising converting alpha-ketoglutaric acid (AKG) into alpha-ketoadipic acid (AKA) and converting alpha-ketoadipic acid into alpha-ketopimelic acid. This reaction may be catalysed by a biocatalyst. AKG may, e.g., be prepared biocatalytically from a carbon source, such as a carbohydrate, in a manner known in the art per se.

A suitable biocatalyst for preparing AKP from AKG may in particular be selected amongst biocatalysts catalysing $C_1$-elongation of alpha-ketoglutaric acid into alpha-ketoadipic acid and/or $C_1$-elongation of alpha-ketoadipic acid into alpha-ketopimelic acid.

In a specific embodiment, the preparation of AKP is catalysed by a biocatalyst comprising a. an AksA enzyme or an homologue thereof;

b. at least one enzyme selected from the group of AksD enzymes, AksE enzymes, homologues of AksD enzymes and homologues of AksE enzymes; and c. an AksF enzyme or a homologue thereof.

One or more of the AksA, AksD, AksE, AksF enzymes or homologues thereof may be found in an organism selected from the group of methanogenic archaea, preferably selected from the group of *Methanococcus, Methanocaldococcus, Methanosarcina, Methanothermobacter, Methanosphaera, Methanopyrus* and *Methanobrevibacter.*

In a specific embodiment, the biocatalyst catalysing the preparation of AKP from alpha-ketoglutaric acid (AKG) comprises an enzyme system catalysing the conversion of alpha-ketoglutaric acid into alpha-ketoadipic acid, wherein said enzyme system forms part of the alpha-amino adipate pathway for lysine biosynthesis. The term 'enzyme system' is in particular used herein for a single enzyme or a group of enzymes whereby a specific conversion can be catalysed.

The preparation of AKP from AKG may comprise one or more biocatalytic reactions with known or unknown intermediates e.g. the conversion of AKG into AKA or the conversion of AKA into AKP. Such system may be present inside a cell or isolated from a cell. The enzyme system may in particular be from an organism selected from the group of yeasts, fungi, archaea and bacteria, in particular from the group of *Penicillium, Cephalosporium, Paelicomyces, Trichophytum, Aspergillus, Phanerochaete, Emericella, Ustilago, Schizosaccharomyces, Saccharomyces, Candida, Yarrowia, Pichia, Kluyveromyces, Thermus, Deinococcus, Pyrococcus, Sulfolobus, Thermococcus, Methanococcus, Methanocaldococcus, Methanosphaera, Methanopyrus, Methanobrevibacter, Methanosarcina* and *Methanothermobacter.*

In a specific embodiment, the biocatalyst catalysing the preparation of AKP from alpha-ketoglutaric acid comprises an enzyme system catalysing the conversion of alpha-ketoglutaric acid into alpha-ketoadipic acid, wherein at least one of the enzymes of the enzyme system originates from nitrogen fixing bacteria selected from the group of cyanobacteria, rhizobiales, γ-proteobacteria and actinobacteria, in particular from the group of *Anabaena, Microcystis, Synechocystis, Rhizobium, Bradyrhizobium, Pseudomonas, Azotobacter, Klebsiella* and *Frankia.*

Examples of homologues for these Aks enzymes and the genes encoding these enzymes are given in the Tables 1A and 1B on the following pages.

References to gene and protein can be found via URL:

TABLE 1A

| Enzyme name | Organism | gene | Protein |
|---|---|---|---|
| AksA | *Methanocaldococcus jannashii* | MJ0503 | NP_247479 |
| | *Methanothermobacter thermoautotropicum* ΔH | MTH1630 | NP_276742 |
| | *Methanococcus maripaludis* S2 | MMP0153 | NP_987273 |
| | *Methanococcus maripaludis* C5 | MmarC5_1522 | YP_001098033 |
| | *Methanococcus maripaludis* C7 | MmarC7_1153 | YP_001330370 |
| | *Methanosphaera stadtmanae* DSM 3091 | Msp_0199 | YP_447259 |
| | *Methanopyrus kandleri* AV19 | MK1209 | NP_614492 |
| | *Methanobrevibacter smithii* ATCC35061 | Msm_0722 | YP_001273295 |
| | *Methanococcus vannielii* SB | Mevan_1158 | YP_001323668 |
| | *Methanococcus aeolicus* Nankai 3 | Maeo_0994 | YP_001325184 |
| AksD | *Methanocaldococcus jannashii* | MJ1003 | NP_247997 |
| | *Methanothermobacter thermoautotropicum* ΔH | MTH1386 | NP_276502 |
| | *Methanococcus maripaludis* S2 | Mmp1480 | NP_988600 |
| | *Methanococcus maripaludis* C5 | MmarC5_0098 | YP_001096630 |
| | *Methanococcus maripaludis* C7 | MmarC7_0724 | YP_001329942 |
| | *Methanosphaera stadtmanae* DSM 3091 | Msp_1486 | YP_448499 |
| | *Methanopyrus kandleri* AV19 | MK1440 | NP_614723 |
| | *Methanobrevibacter smithii* ATCC35061 | Msm_0723 | YP_001273296 |
| | *Methanococcus vannielii* SB | Mevan_0789 | YP_001323307 |
| | *Methanococcus aeolicus* Nankai 3 | Maeo_0311 | YP_001324511 |

References to gene and protein can be found via URL: ncbi[dot]nlm[dot]nih[dot]gov[slash], (as available on 15 Apr. 2008)

TABLE 1B

| Enzyme name | Organism | gene | Protein |
|---|---|---|---|
| AksE | *Methanocaldococcus jannashii* | MJ1271 | NP_248267 |
| | *Methanothermobacter thermoautotropicum* ΔH | MTH1387 | NP_276503 |
| | *Methanococcus maripaludis* S2 | MMP0381 | NP_987501 |
| | *Methanococcus maripaludis* C5 | MmarC5_1257 | YP_001097769 |

TABLE 1B-continued

| Enzyme name | Organism | gene | Protein |
|---|---|---|---|
| | Methanococcus maripaludis C7 | MmarC7_1379 | YP_001330593 |
| | Methanosphaera stadtmanae DSM 3091 | Msp_1485 | YP_448498 |
| | Methanopyrus kandleri AV19 | MK0781 | NP_614065 |
| | Methanobrevibacter smithii ATCC35061 | Msm_0847 | YP_001273420 |
| | Methanococcus vannielii SB | Mevan_1368 | YP_001323877 |
| | Methanococcus aeolicus Nankai 3 | Maeo_0652 | YP_001324848 |
| AksF | Methanocaldococcus jannashii | MJ1596 | NP_248605 |
| | Methanothermobacter thermoautotropicum ΔH | MTH184 | NP_275327 |
| | Methanococcus maripaludis S2 | MMP0880 | NP988000 |
| | Methanococcus maripaludis C5 | MmarC5_0688 | YP001097214 |
| | Methanococcus maripaludis C7 | MmarC7_0128 | YP_001329349 |
| | Methanosphaera stadtmanae DSM 3091 | Msp_0674 | YP_447715 |
| | Methanopyrus kandleri AV19 | MK0782 | NP_614066 |
| | Methanobrevibacter smithii ATCC35061 | Msm_0373 | YP001272946 |
| | Methanococcus vannielii SB | Mevan_0040 | YP_001322567 |
| | Methanococcus aeolicus Nankai 3 | Maeo_1484 | YP_001325672 |

References to gene and protein can be found via URL: ncbi[dot]nlm[dot]nih[dot]gov[slash], (as available on 15 Apr. 2008)

If desired, 6-ACA obtained in accordance with the invention can be cyclised to form caprolactam, e.g. as described in U.S. Pat. No. 6,194,572.

Reaction conditions for any biocatalytic step in the context of the present invention may be chosen depending upon known conditions for the biocatalyst, in particular the enzyme, the information disclosed herein and optionally some routine experimentation.

In principle, the pH of the reaction medium used may be chosen within wide limits, as long as the biocatalyst is active under the pH conditions. Alkaline, neutral or acidic conditions may be used, depending on the biocatalyst and other factors. In case the method includes the use of a micro-organism, e.g. for expressing an enzyme catalysing a method of the invention, the pH is selected such that the micro-organism is capable of performing its intended function or functions. The pH may in particular be chosen within the range of four pH units below neutral pH and two pH units above neutral pH, i.e. between pH 3 and pH 9 in case of an essentially aqueous system at 25° C. A system is considered aqueous if water is the only solvent or the predominant solvent (>50 wt. %, in particular >90 wt. %, based on total liquids), wherein e.g. a minor amount of alcohol or another solvent (<50 wt. %, in particular <10 wt. %, based on total liquids) may be dissolved (e.g. as a carbon source) in such a concentration that micro-organisms which may be present remain active. In particular in case a yeast and/or a fungus is used, acidic conditions may be preferred, in particular the pH may be in the range of pH 3 to pH 8, based on an essentially aqueous system at 25° C. If desired, the pH may be adjusted using an acid and/or a base or buffered with a suitable combination of an acid and a base.

In principle, the incubation conditions can be chosen within wide limits as long as the biocatalyst shows sufficient activity and/or growth. This includes aerobic, micro-aerobic, oxygen limited and anaerobic conditions.

Anaerobic conditions are herein defined as conditions without any oxygen or in which substantially no oxygen is consumed by the biocatalyst, in particular a micro-organism, and usually corresponds to an oxygen consumption of less than 5 mmol/l·h, in particular to an oxygen consumption of less than 2.5 mmol/l·h, or less than 1 mmol/l·h.

Aerobic conditions are conditions in which a sufficient level of oxygen for unrestricted growth is dissolved in the medium, able to support a rate of oxygen consumption of at least 10 mmol/l·h, more preferably more than 20 mmol/l·h, even more preferably more than 50 mmol/l·h, and most preferably more than 100 mmol/l·h.

Oxygen-limited conditions are defined as conditions in which the oxygen consumption is limited by the oxygen transfer from the gas to the liquid. The lower limit for oxygen-limited conditions is determined by the upper limit for anaerobic conditions, i.e. usually at least 1 mmol/l·h, and in particular at least 2.5 mmol/l·h, or at least 5 mmol/l·h. The upper limit for oxygen-limited conditions is determined by the lower limit for aerobic conditions, i.e. less than 100 mmol/l·h, less than 50 mmol/l·h, less than 20 mmol/l·h, or less than to 10 mmol/l·h.

Whether conditions are aerobic, anaerobic or oxygen limited is dependent on the conditions under which the method is carried out, in particular by the amount and composition of ingoing gas flow, the actual mixing/mass transfer properties of the equipment used, the type of micro-organism used and the micro-organism density.

In principle, the temperature used is not critical, as long as the biocatalyst, in particular the enzyme, shows substantial activity. Generally, the temperature may be at least 0° C., in particular at least 15° C., more in particular at least 20° C. A desired maximum temperature depends upon the biocatalyst. In general such maximum temperature is known in the art, e.g. indicated in a product data sheet in case of a commercially available biocatalyst, or can be determined routinely based on common general knowledge and the information disclosed herein. The temperature is usually 90° C. or less, preferably 70° C. or less, in particular 50° C. or less, more in particular or 40° C. or less.

In particular if a biocatalytic reaction is performed outside a host organism, a reaction medium comprising an organic solvent may be used in a high concentration (e.g. more than 50%, or more than 90 wt. %), in case an enzyme is used that retains sufficient activity in such a medium.

In an advantageous method 6-ACA is prepared making use of a whole cell biotransformation of the substrate for 6-ACA or an intermediate for forming 6-ACA (AKP, AAP or 5-FVA), comprising a micro-organism wherein one or more biocatalysts (usually one or more enzymes) catalysing the biotransformation are produced, such as one or more biocatalysts selected from the group of biocatalysts capable of catalysing the conversion of AKP to AAP, biocatalysts capable of catalysing the conversion of AAP to 6-ACA, biocatalysts capable of catalysing the conversion of AKP to 5-FVA and biocatalysts capable of catalysing the conversion of 5-FVA to 6-ACA. In a preferred embodiment the micro-organism is capable of producing a decarboxylase and/or at least one enzyme selected from amino acid dehydrogenases and aminotransferases are produced. capable of catalysing a reaction step as described above, and a carbon source for the micro-organism.

The carbon source may in particular contain at least one compound selected from the group of monohydric alcohols, polyhydric alcohols, carboxylic acids, carbon dioxide, fatty acids, glycerides, including mixtures comprising any of said compounds. Suitable monohydric alcohols include methanol and ethanol, Suitable polyols include glycerol and carbohydrates. Suitable fatty acids or glycerides may in particular be provided in the form of an edible oil, preferably of plant origin.

In particular a carbohydrate may be used, because usually carbohydrates can be obtained in large amounts from a biologically renewable source, such as an agricultural product, preferably an agricultural waste-material. Preferably a carbohydrate is used selected from the group of glucose, fructose, sucrose, lactose, saccharose, starch, cellulose and hemi-cellulose. Particularly preferred are glucose, oligosaccharides comprising glucose and polysaccharides comprising glucose.

A cell, in particular a recombinant cell, comprising one or more biocatalysts (usually one or more enzymes) for catalysing a reaction step in a method of the invention can be constructed using molecular biological techniques, which are known in the art per se. For instance, if one or more biocatalysts are to be produced in a recombinant cell (which may be a heterologous system), such techniques can be used to provide a vector (such as a recombinant vector) which comprises one or more genes encoding one or more of said biocatalysts. One or more vectors may be used, each comprising one or more of such genes. Such vector can comprise one or more regulatory elements, e.g. one or more promoters, which may be operably linked to a gene encoding an biocatalyst.

As used herein, the term "operably linked" refers to a linkage of polynucleotide elements (or coding sequences or nucleic acid sequence) in a functional relationship. A nucleic acid sequence is "operably linked" when it is placed into a functional relationship with another nucleic acid sequence. For instance, a promoter or enhancer is operably linked to a coding sequence if it affects the transcription of the coding sequence.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skilled in the art to act directly or indirectly to regulate the amount of transcription from the promoter. A "constitutive" promoter is a promoter that is active under most environmental and developmental conditions. An "inducible" promoter is a promoter that is active under environmental or developmental regulation. The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain.

The promoter that could be used to achieve the expression of the nucleic acid sequences coding for an enzyme for use in a method of the invention, in particular an aminotransferase, an amino acid dehydrogenase or a decarboxylase, such as described herein above may be native to the nucleic acid sequence coding for the enzyme to be expressed, or may be heterologous to the nucleic acid sequence (coding sequence) to which it is operably linked. Preferably, the promoter is homologous, i.e. endogenous to the host cell.

If a heterologous promoter (to the nucleic acid sequence encoding for the enzyme of interest) is used, the heterologous promoter is preferably capable of producing a higher steady state level of the transcript comprising the coding sequence (or is capable of producing more transcript molecules, i.e. mRNA molecules, per unit of time) than is the promoter that is native to the coding sequence. Suitable promoters in this context include both constitutive and inducible natural promoters as well as engineered promoters, which are well known to the person skilled in the art.

A "strong constitutive promoter" is one which causes mRNAs to be initiated at high frequency compared to a native host cell. Examples of such strong constitutive promoters in Gram-positive micro-organisms include SP01-26, SP01-15, veg, pyc (pyruvate carboxylase promoter), and amyE.

Examples of inducible promoters in Gram-positive micro-organisms include, the IPTG inducible Pspac promoter, the xylose inducible PxylA promoter.

Examples of constitutive and inducible promoters in Gram-negative microorganisms include, but are not limited to, tac, tet, trp-tet, lpp, lac, lpp-lac, lacIq, T7, T5, T3, gal, trc, ara ($P_{BAD}$), SP6, $\lambda$-$P_R$, and $\lambda$-$P_L$.

Promoters for (filamentous) fungal cells are known in the art and can be, for example, the glucose-6-phosphate dehydrogenase gpdA promoters, protease promoters such as pepA, pepB, pepC, the glucoamylase glaA promoters, amylase amyA, amyB promoters, the catalase catR or catA promoters, glucose oxidase goxC promoter, beta-galactosidase lacA promoter, alpha-glucosidase aglA promoter, translation elongation factor tefA promoter, xylanase promoters such as xlnA, xlnB, xlnC, xlnD, cellulase promoters such as eglA, eglB, cbhA, promoters of transcriptional regulators such as areA, creA, xlnR, pacC, prtT, or another promotor, and can be found among others at the NCBI website (URL:ncbi[dot]nlm[dot]nih[dot]gov[slash]entrez[slash]).

The term "heterologous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are not endogenous to the cell into which it is introduced, but has been obtained from another cell or synthetically or recombinantly produced. Generally, though not necessarily, such nucleic acids encode proteins that are not normally produced by the cell in which the DNA is transcribed or expressed. Similarly exogenous RNA encodes for proteins not normally expressed in the cell in which the exogenous RNA is present. Heterologous nucleic acids and proteins may also be referred to as foreign nucleic acids or proteins. Any nucleic acid or protein that one of skill in the art would recognize as heterologous or foreign to the cell in which it is expressed is herein encompassed by the term heterologous nucleic acid or protein.

A method according to the invention may be carried out in a host organism, which may be novel.

Accordingly, the invention also relates to a host cell comprising one or more biocatalysts capable of catalysing at least one reaction step in a method of the invention, in particular capable of catalysing at least one reaction step in the conversion of AKP, AAP or 5-FVA to 6-ACA. The invention also relates to a novel vector comprising one or more genes encoding for one or more enzymes capable of catalysing at least one reaction step in a method of the invention, in particular capable of catalysing at least one reaction step in the conversion of AKP to 6-ACA and to a novel host cell comprising one or more genes encoding for one or more enzymes capable of catalysing at least one reaction step in a method of the invention, in particular capable of catalysing at least one reaction step in the conversion of AKP to 6-ACA (which one or more genes may form part of one or more vectors).

In a specific embodiment, a host cell according to the invention is a recombinant cell comprising a nucleic acid sequence encoding a biocatalyst capable of catalysing a transamination reaction or a reductive amination reaction to form alpha-aminopimelic acid from alpha-ketopimelic acid. Said sequence may be part of a vector or may have been inserted into the chromosomal DNA.

In particular, a host cell or vector according to the invention may comprise at least one nucleic acid sequence, in particular at least two nucleic acid sequences, selected from the group of nucleic acid sequences encoding an enzyme with α-ketopimelic acid decarboxylase activity, nucleic acid sequences encoding an enzyme with 5-formylpentanoate aminotransferase activity, nucleic acid sequences encoding an enzyme with α-ketopimelic acid aminotransferase activity, nucleic acid sequences encoding an enzyme with α-ketopimelic acid dehydrogenase activity and nucleic acid sequences encoding an enzyme with α-aminopimelic acid decarboxylase activity. Of these sequences, typically one or more, in particular two or more, are recombinant sequences.

In preferred embodiment the host cell, typically a recombinant host cell, or the vector according to the invention comprises a nucleic acid sequence encoding at least one biocatalyst having α-ketopimelic acid decarboxylase activity, and/or at least one nucleic acid sequence selected from sequences encoding a biocatalyst with 5-formylpentanoate aminotransferase activity.

In such an embodiment, the nucleic acid sequence encoding an enzyme with α-ketopimelic acid decarboxylase activity may in particular comprise an amino acid sequence according to Sequence ID 31, Sequence ID 34, Sequence ID 37, Sequence ID 40, Sequence ID 43 or Sequence ID 46 or a homologue of any of these sequences and/or the nucleic acid sequence encoding an enzyme with 5-formylpentanoate aminotransferase may in particular comprise an amino acid sequence according to Sequence ID 2, Sequence ID 5, Sequence ID 8, Sequence ID 65 Sequence ID 67, Sequence ID 69 or a homologue thereof. One or more of said nucleic acid sequences may form part of one or more recombinant vectors.

In a further preferred embodiment, the vector or host cell comprises a nucleic acid sequence encoding an enzyme with α-ketopimelic acid aminotransferase activity and/or a nucleic acid sequence encoding an enzyme with α-aminopimelic acid decarboxylase activity. The nucleic acid sequence encoding an enzyme with α-ketopimelic acid aminotransferase activity may in particular comprise an amino acid sequence according to Sequence ID 2, Sequence ID 8, Sequence ID 12, Sequence ID 15, Sequence ID 17, Sequence ID 19, Sequence ID 21, Sequence ID 23, Sequence ID 25, Sequence ID 27, Sequence ID 29, or a homologue thereof. One or more of said nucleic acid sequences may form part of one or more recombinant vectors.

In a specific preferred embodiment, a host cell according to the invention comprises a nucleic acid sequence encoding an enzyme with α-aminopimelate 2-dehydrogenase activity and a nucleic acid sequence encoding an enzyme with α-aminopimelate decarboxylase activity.

In a specific preferred embodiment, a host cell according to the invention comprises a nucleic acid sequence encoding an enzyme with 6-aminocaproic acid 6-dehydrogenase activity and a nucleic acid sequence encoding an enzyme with α-ketopimelic acid decarboxylase activity.

One or more suitable genes of a host cell or vectors according to the invention may in particular be selected amongst genes encoding an enzyme as mentioned herein above.

In a specific embodiment, the host cell is a recombinant cell comprising at least one nucleic acid sequence selected from the group of sequences as identified in any of Sequence ID 1, Sequence ID 3, Sequence ID 4, Sequence ID 6, Sequence ID 7, Sequence ID 11, Sequence ID 13, Sequence ID 14, Sequence ID 16, Sequence ID 18, Sequence ID 20, Sequence ID 22, Sequence ID 24, Sequence ID 26, Sequence ID 28, Sequence ID 30, Sequence ID 32, Sequence ID 33, Sequence ID 35, Sequence ID 36, Sequence ID 38, Sequence ID 39, Sequence ID 41, Sequence ID 42, Sequence ID 44, Sequence ID 45, Sequence ID 47, Sequence ID 64, Sequence ID 66, Sequence ID 68 and functional analogues thereof.

A nucleic acid sequence encoding an enzyme with 5-FVA aminotransferase activity, may in particular be a sequence selected from the group of sequences represented by any of the Sequence ID's 1, 3, 4, 6, 7, 64, 66, 68, and functional analogues of any of these sequences.

As used herein, the term "functional analogues" at least includes other sequences encoding an enzyme having the same amino acid sequence and other sequences encoding a homologue of such enzyme.

A nucleic acid sequence encoding an enzyme with AKP decarboxylase activity may in particular be a sequence selected from the group of sequences represented by any of the Sequence ID's 30, 32, 33, 35, 36, 38, 39, 41, 42, 44, 45, 47 and functional analogues of any of these sequences.

In a preferred embodiment, the host cell comprises a nucleic acid sequence encoding an enzyme, capable of catalysing the conversion of AAP to AKP, according to Sequence ID No.: 1, 3, 7, 11, 13, 14, 16, 18, 20, 22, 24, 26, 28, or a functional analogue thereof, which may be a wild type or non-wild type sequence In a specific embodiment, the host cell comprises at least one nucleic acid sequence encoding a biocatalyst having alpha-aminopimelic acid decarboxylase activity, which may be homologous or heterologous to the host cell. In particular such biocatalyst may be selected from the group of decarboxylases (E.C. 4.1.1), more in particular from the group of glutamate decarboxylases (EC 4.1.1.15), diaminopimelate decarboxylases (EC 4.1.1.20) aspartate 1-decarboxylases (EC 4.1.1.11), branched chain alpha-keto acid decarboxylases, alpha-ketoisovalerate decarboxylases, alpha-ketoglutarate decarboxylases, pyruvate decarboxylases (EC 4.1.1.1) and oxaloacetate decarboxylases (E.C. 4.1.1.3).

In a specific embodiment, the host cell comprises one or more enzymes catalysing the formation of AKP from AKG (see also above). Use may be made of an enzyme system forming part of the alpha-amino adipate pathway for lysine biosynthesis. The term 'enzyme system' is in particular used herein for a single enzyme or a group of enzymes whereby a specific conversion can be catalysed. Said conversion may comprise one or more chemical reactions with known or unknown intermediates e.g. the conversion of AKG into AKA or the conversion of AKA into AKP. Such system may be present inside a cell or isolated from a cell. It is known that aminotransferases often have a wide substrate range. If present, it may be desired to decrease activity of one or more such enzymes in a host cell such that activity in the conversion of AKA to alpha-aminoadipate (AAA) is reduced, whilst maintaining relevant catalytic functions for biosynthesis of other amino acids or cellular components. Also a host cell devoid of any other enzymatic activity resulting in the conversion of AKA to an undesired side product is preferred.

In a preferred host cell, suitable for preparing AAP making use of a whole cell biotransformation process, one or more biocatalysts capable of catalysing at least one reaction step in the preparation of alpha-ketopimelic acid from alpha-ketoglutaric acid are encoded for. Suitable biocatalysts are, e.g., as described above when discussing the preparation of AKP.

The host cell may for instance be selected from bacteria, yeasts or fungi. In particular the host cell may be selected from the genera selected from the group of *Aspergillus, Penicillium, Saccharomyces, Kluyveromyces, Pichia, Candida, Hansenula, Bacillus, Corynebacterium, Pseudomonas, Gluconobacter, Methanococcus, Methanobacterium, Methanocaldococcus* and *Methanosarcina* and *Escherichia*. Herein, usually one or more encoding nucleic acid sequences as mentioned above have been cloned and expressed.

In particular, the host strain and, thus, a host cell suitable for the biochemical synthesis of 6-ACA may be selected from the group of *Escherichia coli, Bacillus subtilis, Bacillus amyloliquefaciens, Corynebacterium glutamicum, Aspergillus niger, Penicillium chrysogenum, Saccharomyces cervisiae, Hansenula polymorpha, Candida albicans, Kluyveromyces lactis, Pichia stipitis, Pichia pastoris, Methanobacterium thermoautothrophicum* ΔH, *Methanococcus maripaludis, Methanococcus voltae, Methanosarcina acetivorans, Methanosarcina barkeri* and *Methanosarcina mazei* host cells. In a preferred embodiment, the host cell is capable of producing lysine (as a precursor).

The host cell may be in principle a naturally occurring organism or may be an engineered organism. Such an organism can be engineered using a mutation screening or metabolic engineering strategies known in the art. In a specific embodiment, the host cell naturally comprises (or is capable of producing) one or more of the enzymes suitable for catalysing a reaction step in a method of the invention, such as one or more activities selected from the group of decarboxylases, aminotransferases and amino acid dehydrogenases capable of catalysing a reaction step in a method of the invention. For instance *E. coli* may naturally be capable of producing an enzyme catalysing a transamination in a method of the invention. It is also possible to provide a recombinant host cell with both a recombinant gene encoding an aminotransferase or amino acid dehydrogenase capable of catalysing a reaction step in a method of the invention and a recombinant gene encoding a decarboxylase gene capable of catalysing a reaction step in a method of the invention.

For instance a host cell may be selected of the genus *Corynebacterium*, in particular *C. glutamicum*, enteric bacteria, in particular *Escherichia coli, Bacillus*, in particular *B. subtilis* and *B. methanolicus*, and *Saccharomyces*, in particular *S. cerevisiae*. Particularly suitable are *C. glutamicum* or *B. methanolicus* strains which have been developed for the industrial production of lysine.

The invention further relates to a micro-organism, which may be a wild-type micro-organism isolated from its natural environment or a recombinant micro-organism, comprising DNA containing a nucleic acid sequence as identified in any Sequence ID selected from the group of Sequence ID 3, Sequence ID 6, Sequence ID 13, Sequence ID No. 32, Sequence ID No. 35, Sequence ID No. 41, Sequence ID No. 44, Sequence ID No. 47, and functional analogues thereof.

Functional analogues of a nucleotides sequence, as referred to herein, are in particular nucleotide sequences encoding the same amino acid sequence as that nucleotide sequence or encoding a homologue of that nucleotide sequence. In particular, preferred functional analogues are nucleotide sequence having a similar, the same or a better level of expression in a host cell of interest as the nucleotide sequence of which it is referred to as being a functional analogue of.

The invention further relates to a polynucleotide or vector comprising a nucleic acid sequence as identified in any Sequence ID selected from the group of Sequence ID 3, Sequence ID 6, Sequence ID 13, Sequence ID No. 32, Sequence ID No. 35, Sequence ID No. 41, Sequence ID No. 44, Sequence ID No. 47 and non-wild-type functional analogues thereof. Such polynucleotide or vector is in particular advantageous for providing a host cell, especially an *E. coli* host cell, or another host cell which is capable of catalysing at least one reaction step in the conversion of AKP to 6-ACA with a high yield, compared to a corresponding wild-type gene.

Optionally, the polynucleotide or vector comprises one or more nucleic acid sequences encoding one or more other biocatalysts suitable for catalysing a reaction step in a method according to the invention, in particular such one or more of the biocatalyst referred to in above.

The invention further relates to a method for preparing alpha-aminopimelic acid (AAP), comprising converting AKP into AAP, which conversion is catalysed by a biocatalyst.

For such method in particular a biocatalyst may be used having aminotransferase activity or reductive amination activity as described above.

As indicated above, the AAP may thereafter be used for the preparation of 6-ACA. Alternatively, AAP may be used as such, e.g. as a chemical for biochemical research or as a pH-buffer compound, e.g. for use in an preparative or analytical separation technique such as liquid chromatography or capillary electrophoresis.

Further, AAP prepared in a method of the invention may further be used in the preparation of another compound, for instance, AAP may be converted into caprolactam. As described above, and illustrated in an example, below. AAP can be chemically converted in caprolactam, e.g. by exposure to a high temperature. Without being bound by theory, it is contemplated that also in this reaction 6-ACA may be formed as a short-lived intermediate.

Next, the invention will be illustrated by the following examples.

EXAMPLES

General Methods
Molecular and Genetic Techniques
Standard genetic and molecular biology techniques are generally known in the art and have been previously described (Maniatis et al. 1982 "Molecular cloning: a laboratory manual". Cold Spring Harbor Laboratory, Cold Spring Harbor, N.Y.; Miller 1972 "Experiments in molecular genetics", Cold Spring Harbor Laboratory, Cold Spring Harbor; Sambrook and Russell 2001 "Molecular cloning: a laboratory manual" (3rd edition), Cold Spring Harbor Laboratory, Cold Spring Harbor Laboratory Press; F. Ausubel et al, eds., "Current protocols in molecular biology", Green Publishing and Wiley Interscience, New York 1987).

Plasmids and Strains
pBAD/Myc-His C was obtained from Invitrogen (Carlsbad, Calif., USA). Plasmid pBAD/Myc-His-DEST constructed as described in WO2005/068643, was used for protein expression. *E. coli* TOP10 (Invitrogen, Carlsbad, Calif., USA) was used for all cloning procedures and for expression of target genes.

Media

LB medium (10 g/l tryptone, 5 g/l yeast extract, 5 g/l NaCl) was used for growth of *E. coli*. Antibiotics (50 µg/ml carbenicillin) were supplemented to maintain plasmids. For induction of gene expression under control of the $P_{BAD}$ promoter in pBAD/Myc-His-DEST derived plasmids, L-arabinose was added to a final concentration of 0.2% (w/v).

Identification of Plasmids

Plasmids carrying the different genes were identified by genetic, biochemical, and/or phenotypic means generally known in the art, such as resistance of transformants to antibiotics, PCR diagnostic analysis of transformant or purification of plasmid DNA, restriction analysis of the purified plasmid DNA or DNA sequence analysis.

HPLC-MS Analysis Method for the Determination of 5-FVA

5-FVA was detected by selective reaction monitoring (SRM)-MS, measuring the transition m/z 129→83. Concentrations for 5-FVA were calculated by measuring the peak area of the 5-FVA peak eluting at approximately 6 min. Calibration was performed by using an external standard procedure. All the LC-MS experiments were performed on an Agilent 1200 LC system, consisting of a quaternary pump, autosampler and column oven, coupled with an Agilent 6410 QQQ triple quadrupole MS.

LC Conditions:
Column: 50×4.6 mm Nucleosil C18, 5 µm (Machery & Nagel) pre column coupled to a 250×4.6 mm id. Prevail C18, 5 µm (Alltech)
Column temperature: room temperature
Eluent: A: water containing 0.1% formic acid
B: acetonitrile containing 0.1% formic acid
Gradient:

| time (min) | % eluent B |
|---|---|
| 0 | 10 |
| 6 | 50 |
| 6.1 | 10 |
| 11 | 10 |

Flow: 1.2 ml/min, before entering the MS the flow is split 1:3
Injection volume: 2 µl
MS Conditions:
Ionisation: negative ion electrospray
source conditions: ionspray voltage: 5 kV
temperature: 350° C.
fragmentor voltage and collision energy optimized
Scan mode: selective reaction mode: transition m/z 129→83
HPLC-MS Analysis for the Determination of AAP AAP was detected by selected ion monitoring (SIM)-MS, measuring the protonated molecule for AAP with m/z 176. Concentrations for AAP were calculated by measuring the peak area of the AAP peak eluting at a retention time of 2.7 minutes in the samples. Calibration was performed by using an external standard procedure. All the LC-MS experiments were performed on an Agilent 1100 LC system consisting of a quaternary pump, degasser, autosampler and column oven, coupled with an API 2000 triple quadrupole MS (Applied Biosystems).

LC conditions were as follows:
Column: 50*4 Nucleosil C18, 5 µm (Macherey-Nagel)+250× 4.6 Prevail C18, 5 µm (Alltech), both at room temperature (RT)
Eluent: A=0.1% (v/v) formic acid in ultrapure water
B=0.1% (v/v) formic acid in acetonitrile (pa, Merck)
Flow: 1.2 ml/min, before entering the MS the flow was split 1:3
Gradient: The gradient was started at t=0 minutes with 90% (v/v) A and changed within 6 minutes to 50% (v/v) A. At 6.1 minutes the gradient was changed to the original condition.
Injection volume: 2 µl
MS conditions: Positive ion electrospray was used for ionization
Detection: in SIM mode on m/z 176, with a dwell time of 100 msec.
HPLC-MS Analysis for the Determination of 6-ACA
Calibration:

The calibration was performed by an external calibration line of 6-ACA (m/z 132→m/z 114, Rt 7.5 min). All the LC-MS experiments were performed on an Agilent 1100, equipped with a quaternary pump, degasser, autosampler, column oven, and a single-quadrupole MS (Agilent, Waldbronn, Germany). The LC-MS conditions were:
Column: 50*4 Nucleosil (Mancherey-Nagel)+250×4.6 Prevail C18 (Alltech), both at room temperature (RT)
Eluent: A=0.1 (v/v) formic acid in ultrapure water
B=Acetonitrile (pa, Merck)
Flow: 1.0 ml/min, before entering the MS the flow was split 1:3
Gradient: The gradient was started at t=0 minutes with 100% (v/v) A, remaining for 15 minutes and changed within 15 minutes to 80% (v/v) B (t=30 minutes). From 30 to 31 minutes the gradient was kept at constant at 80% (v/v) B.
Injection volume: 5 µl
MS detection: ESI(+)–MS
The electrospray ionization (ESI) was run in the positive scan mode with the following conditions; m/z 50-500, 50 V fragmentor, 0.1 m/z step size, 350° C. drying gas temperature, 10 L $N_2$/min drying gas, 50 psig nebuliser pressure and 2.5 kV capillary voltage.
Cloning of Target Genes
Design of Expression Constructs attB sites were added to all genes upstream of the ribosomal binding site and start codon and downstream of the stop codon to facilitate cloning using the Gateway technology (Invitrogen, Carlsbad, Calif., USA).

Gene Synthesis and Construction of Plasmids

Synthetic genes were obtained from DNA2.0 and codon optimised for expression in *E. coli* according to standard procedures of DNA2.0. The aminotransferase genes from *Vibrio fluvialis* JS17 [SEQ ID No. 1] and *Bacillus weihenstephanensis* KBAB4 [SEQ ID No. 4] encoding the amino acid sequences of the *V. fluvialis* JS17 ω-aminotransferase [SEQ ID No. 2] and the *B. weihenstephanensis* KBAB4 aminotransferase (ZP_01186960) [SEQ ID No. 5], respectively, were codon optimised and the resulting sequences [SEQ ID No. 3] and [SEQ ID No. 6] were obtained by DNA synthesis.

The decarboxylase genes from *Escherichia coli* [SEQ ID No. 30], *Saccharomyces cerevisiae* [SEQ ID No. 33], *Zymomonas mobilis* [SEQ ID No. 36], *Lactococcus lactis* [SEQ ID No. 39], [SEQ ID No. 42], and *Mycobacterium tuberculosis* [SEQ ID No. 45], the *Escherichia coli* diaminopimelate decarboxylase LysA [SEQ ID No. 31], the *Saccharomyces cerevisiae* pyruvate decarboxylase Pdc [SEQ ID No. 34], the *Zymomonas mobilis* pyruvate decarboxylase PdcI472A [SEQ ID No. 37], the *Lactococcus lactis* branched chain alpha-keto acid decarboxylase KdcA [SEQ ID No. 40] and alpha-ketoisovalerate decarboxylase KivD [SEQ ID No. 43], and the *Mycobacterium tuberculosis* alpha ketoglutarate decarboxylase Kgd [SEQ ID No. 46], respectively, were also codon optimised and the resulting sequences [SEQ ID No. 32], [SEQ ID No. 35], [SEQ ID No. 38], [SEQ ID No. 41], [SEQ ID No. 44], and [SEQ ID No. 47] were obtained by DNA synthesis, respectively.

The gene constructs were cloned into pBAD/Myc-His-DEST expression vectors using the Gateway technology (Invitrogen) via the introduced attB sites and pDONR201 (Invitrogen) as entry vector as described in the manufacturer's protocols (www[dot]invitrogen[dot]com). This way the expression vectors pBAD-Vfl_AT and pBAD-Bwe_AT were obtained, respectively. The corresponding expression strains were obtained by transformation of chemically competent *E. coli* TOP10 (Invitrogen) with the respective pBAD-expression vectors.

Cloning by PCR

Various genes encoding a biocatalyst were amplified from genomic DNA by PCR using PCR Supermix High Fidelity (Invitrogen) according to the manufacturer's specifications, using primers as listed in the following table.

TABLE 2

| origin of gene | gene Sequence ID | enzyme Sequence ID | primer Sequence ID's |
|---|---|---|---|
| *Pseudomonas aeruginosa* | 7 | 8 | 9&10 |
| *Pseudomonas aeruginosa* | 26 | 27 | 60&61 |
| *Pseudomonas aeruginosa* | 66 | 67 | 72&73 |
| *Pseudomonas aeruginosa* | 68 | 69 | 74&75 |
| *Bacillus subtilis* | 14 | 15 | 48&49 |
| *Bacillus subtilis* | 16 | 17 | 50&51 |
| *Bacillus subtilis* | 64 | 65 | 70&71 |
| *Rhodobacter sphaeroides* | 18 | 19 | 52&53 |
| *Legionella pneumophilia* | 20 | 21 | 54&55 |
| *Nitrosomas europaea* | 22 | 23 | 56&57 |
| *Neisseria gonorrhoeae* | 24 | 25 | 58&59 |
| *Rhodopseudomonas palustris* | 28 | 29 | 62&63 |

PCR reactions were analysed by agarose gel electrophoresis and PCR products of the correct size were eluted from the gel using the QIAguick PCR purification kit (Qiagen, Hilden, Germany). Purified PCR products were cloned into pBAD/Myc-His-DEST expression vectors using the Gateway technology (Invitrogen) via the introduced attB sites and pDONR-zeo (Invitrogen) as entry vector as described in the manufacturer's protocols. The sequence of genes cloned by PCR was verified by DNA sequencing. This way the expression vectors pBAD-Pae-_gi9946143_AT, pBAD-Bsu_gi16078032_AT, pBAD-Bsu_gi16080075_AT, pBAD-Bsu_gi16077991_AT, pBAD-Rsp_AT, pBAD-Lpn_AT, pBAD-Neu_AT, pBAD-Ngo_AT, pBAD-Pae_gi9951299_AT, pBAD-Pae_gi9951072_AT, pBAD-Pae_gi9951630_AT and pBAD-Rpa_AT were obtained. The corresponding expression strains were obtained by transformation of chemically competent *E. coli* TOP10 (Invitrogen) with the pBAD constructs.

Growth of *E. coli* for Protein Expression

Small scale growth was carried out in 96-deep-well plates with 940 μl media containing 0.02% (w/v) L-arabinose. Inoculation was performed by transferring cells from frozen stock cultures with a 96-well stamp (Kühner, Birsfelden, Switzerland). Plates were incubated on an orbital shaker (300 rpm, 5 cm amplitude) at 25° C. for 48 h. Typically an $OD_{620nm}$ of 2-4 was reached.

Preparation of Cell Lysates
Preparation of Lysis Buffer
The lysis buffer contained the following ingredients:

TABLE 3

| 1M MOPS pH 7.5 | 5 ml |
|---|---|
| DNAse I grade II (Roche) | 10 mg |
| Lysozyme | 200 mg |
| $MgSO_4 \cdot 7H_2O$ | 123.2 mg |
| dithiothreitol (DTT) | 154.2 mg |
| $H_2O$ (MilliQ) | Balance to 100 ml |

The solution was freshly prepared directly before use.
Preparation of Cell Free Extract by Lysis Cells from small scales growth (see previous paragraph) were harvested by centrifugation and the supernatant was discarded. The cell pellets formed during centrifugation were frozen at −20° C. for at least 16 h and then thawed on ice. 500 μl of freshly prepared lysis buffer were added to each well and cells were resuspended by vigorously vortexing the plate for 2-5 min. To achieve lysis, the plate was incubated at room temperature for 30 min. To remove cell debris, the plate was centrifuged at 4° C. and 6000 g for 20 min. The supernatant was transferred to a fresh plate and kept on ice until further use.

Preparation of Cell Free Extract by Sonification

Cells from medium scales growth (see previous paragraph) were harvested by centrifugation and the supernatant was discarded. 1 ml of potassium phosphate buffer pH7 was added to 0.5 g of wet cell pellet and cells were resuspended by vigorously vortexing. To achieve lysis, the cells were sonicated for 20 min. To remove cell debris, the lysates were centrifuged at 4° C. and 6000 g for 20 min. The supernatant was transferred to a fresh tube and frozen at −20° C. until further use.

Preparation of 5-Formylpentanoic Acid by Chemical Hydrolysis of Methyl 5-Formylpentanoate The substrate for the aminotransferase reaction i.e. 5-formylpentanoic acid was prepared by chemical hydrolysis of methyl 5-formylpentanoate as follows: a 10% (w/v) solution of methyl 5-formylpentanoate in water was set at pH 14.1 with NaOH. After 24 h of incubation at 20° C. the pH was set to 7.1 with HCl.

Enzymatic Reactions for Conversion of 5-Formylpentanoic Acid to 6-ACA

Unless specified otherwise, a reaction mixture was prepared comprising 10 mM 5-formylpentanoic acid, 20 mM racemic α-methylbenzylamine, and 200 μM pyridoxal 5'-phosphate in 50 mM potassium phosphate buffer, pH 7.0. 100 μl of the reaction mixture were dispensed into each well of the well plates. To start the reaction, 20 μl of the cell free extracts were added, to each of the wells. Reaction mixtures were incubated on a shaker at 37° C. for 24 h. Furthermore, a chemical blank mixture (without cell free extract) and a biological blank (*E. coli* TOP10 with pBAD/Myc-His C) were incubated under the same conditions. Samples were analysed by HPLC-MS. The results are summarised in the following table.

TABLE 4

6-ACA formation from 5-FVA in the presence of aminotransferases

| Biocatalyst | 6-ACA concentration [mg/kg] |
|---|---|
| E. coli TOP10/pBAD-Vfl_AT | 43* |
| E. coli TOP10/pBAD-Pae_AT | 930 |
| E. coli TOP10/pBAD-Pae_AT | 25* |
| E. coli TOP10/pBAD-Bwe_AT | 24* |
| E. coli TOP10/pBAD-Bsu_gi16077991_AT | 288 |
| E. coli TOP10/pBAD-Pae_gi9951072_AT | 1087 |
| E. coli TOP10/pBAD-Pae_gi9951630_AT | 92 |
| E. coli TOP10 with pBAD/Myc-His C (biological blank) | 0.6 |
| None (chemical blank) | n.d. | n.d.: not detectable
*method differed in that 10 μl cell free extract was used instead of 20 μl, the pyridoxal-5'-phosphate concentration was 50 μM instead of 200 μM and the reaction mixture volume in the wells was 190 μl instead of 100 μl.

It is shown that 6-ACA is formed from 5-FVA in the presence of an aminotransferase.

Enzymatic Reactions for Conversion of AKP to 5-Formylpentanoic Acid

A reaction mixture was prepared comprising 50 mM AKP, 5 mM magnesium chloride, 100 μM pyridoxal 5'-phosphate (for LysA) or 1 mM thiamine diphosphate (for all other enzymes) in 100 mM potassium phosphate buffer, pH 6.5. 4 ml of the reaction mixture were dispensed into a reaction vessel. To start the reaction, 1 ml of the cell free extracts obtained by sonification were added, to each of the wells. In case of the commercial oxaloacetate decarboxylase (Sigma-Aldrich product number 04878), 50 U were used. Reaction mixtures were incubated with a magnetic stirrer at 37° C. for 48 h. Furthermore, a chemical blank mixture (without cell free extract) and a biological blank (E. coli TOP10 with pBAD/Myc-His C) were incubated under the same conditions. Samples from different time points during the reaction were analysed by HPLC-MS. The results are summarised in the following table.

TABLE 5

5-FVA formation from AKP in the presence of decarboxylases

| Biocatalyst | 5-FVA concentration [mg/kg] | | |
|---|---|---|---|
| | 3 h | 18 h | 48 h |
| E. coli TOP10/pBAD-LysA | 150 | 590 | 720 |
| E. coli TOP10/pBAD-Pdc | 1600 | 1700 | 1300 |
| E. coli TOP10/pBAD-PdcI472A | 2000 | 2000 | 1600 |
| E. coli TOP10/pBAD-KdcA | 3300 | 2300 | 2200 |
| E. coli TOP10/pBAD-KivD | 820 | 1400 | 1500 |
| Oxaloacetate decarboxylase | n.d. | 6 | 10 |
| E. coli TOP10 with pBAD/Myc-His C (biological blank) | n.d. | n.d. | n.d. |
| None (chemical blank) | n.d. | n.d. | n.d. | n.d.: not detectable

It is shown that 5-FVA is formed from AKP in the presence of a decarboxylase.

Enzymatic Reactions for Conversion of AKP to 6-ACA in Presence of Recombinant Decarboxylase A reaction mixture was prepared comprising 50 mM AKP, 5 mM magnesium chloride, 100 μM pyridoxal 5'-phosphate (for LysA) or 1 mM thiamine diphosphate (for all other tested biocatalysts) in 100 mM potassium phosphate buffer, pH 6.5. 4 ml of the reaction mixture were dispensed into a reaction vessel. To start the reaction, 1 ml of the cell free extracts were added, to each of the wells. Reaction mixtures were incubated with a magnetic stirrer at 37° C. for 48 h. Furthermore, a chemical blank mixture (without cell free extract) and a biological blank (E. coli TOP10 with pBAD/Myc-His C) were incubated under the same conditions. Samples from different time points during the reaction were analysed by HPLC-MS. The results are summarised in the following table.

TABLE 6

6-ACA formation from AKP in the presence of decarboxylases

| Biocatalyst | 6-ACA concentration [mg/kg] | | |
|---|---|---|---|
| | 3 h | 18 h | 48 h |
| E. coli TOP10/pBAD-LysA | n.a. | 0.01 | 0 |
| E. coli TOP10/pBAD-Pdc | 0.1 | 0.3 | n.a. |
| E. coli TOP10/pBAD-PdcI472A | 0.03 | 0.1 | 0.2 |
| E. coli TOP10/pBAD-KdcA | 0.04 | 0.1 | 0.3 |
| E. coli TOP10/pBAD-KivD | n.a. | 0.3 | 0.6 |
| E. coli TOP10 with pBAD/Myc-His C (biological blank) | n.d. | n.d. | n.d. |
| None (chemical blank) | n.d. | n.d. | n.d. | n.a. = not analysed
n.d. = not detectable

It is shown that 6-ACA is formed from AKP in the presence of a decarboxylase. It is contemplated that the E. coli contained natural 5-FVA aminotransferase activity.

Enzymatic Reactions for Conversion of AKP to 6-ACA in Presence of Recombinant Decarboxylase and Recombinant Aminotransferase A reaction mixture was prepared comprising 50 mM AKP, 5 mM magnesium chloride, 100 μM pyridoxal 5'-phosphate, 1 mM thiamine diphosphate and 50 mM racemic α-methylbenzylamine in 100 mM potassium phosphate buffer, pH 6.5. 1.6 ml of the reaction mixture were dispensed into a reaction vessel. To start the reaction, 0.2 ml of the decarboxylase containing cell free extract and 0.2 ml of the aminotransferase containing cell free extract were added, to each of the reaction vessels. Reaction mixtures were incubated with a magnetic stirrer at 37° C. for 48 h. Furthermore, a chemical blank mixture (without cell free extract) and a biological blank (E. coli TOP10 with pBAD/Myc-His C) were incubated under the same conditions. Samples from different time points during the reaction were analysed by HPLC-MS. The results are summarised in the following table.

TABLE 7

6-ACA formation from AKP in the presence of a recombinant decarboxylase and a recombinant aminotransferase

| | 6-ACA concentration [mg/kg] after 48 hours AT | | |
|---|---|---|---|
| DC | E. coli TOP10/ pBAD-Vfl-AT | E. coli TOP10/ pBAD-Bwe-AT | E. coli TOP10/ pBAD-PAE_gi9946143_AT |
| E. coli TOP10/ pBAD-Pdc | 183.4 | 248.9 | 117.9 |
| E. coli TOP10/ pBAD-PdcI472A | 458.5 | 471.6 | 170.3 |
| E. coli TOP10/ pBAD-KdcA | 497.8 | 497.8 | 275.1 |
| E. coli TOP10/ pBAD-KivD | 510.9 | 510.9 | 314.4 |

AT = aminotransferase
DC = decarboxylase

In the chemical blank and in the biological blank no 6-ACA was detectable.

Further, the results show that compared to the example wherein a host-cell with only recombinant decarboxylase (and no recombinant aminotransferase) the conversion to 6-ACA was improved.

Construction of Plasmids for Expression of Aminotransferases and Decarboxylases in S. cerevisiae The aminotransferase gene from Vibrio fluvialis JS17 encoding the amino acid sequence of the V. fluvialis JS17 ω-aminotransferase [SEQ ID No. 2] was amplified by PCR from pBAD-Vfl_AT [SEQ ID No. 3] using Phusion DNA polymerase (Finnzymes) according to the manufacturers specifications and using specific primers [SEQ ID No. 76 & 77].

The aminotransferase gene from Pseudomonas aeruginosa [SEQ ID No. 7] coding for P. aeruginosa aminotransferase [SEQ ID No. 8] was amplified from pBAD-Pae_AT by PCR using Phusion DNA polymerase (Finnzymes) according to the manufacturers specifications and using specific primers [SEQ ID No. 78 & 79].

The resulting PCR products were cloned into vector pAKP-41 using SpeI and BamHI restriction enzymes resulting in vectors pAKP-79 and pAKP-80 respectively, which now contain the aminotransferase gene under the S. cerevisiae gal10 promoter and the S. cerevisiae adh2 terminator.

The decarboxylase gene from Saccharamyces cerevisiae [SEQ ID No. 33] coding for Saccharamyces cerevisiae pyruvate decarboxylase Pdc [SEQ ID No. 34] was amplified from pBAD-Pdc by PCR using Phusion DNA polymerase (Finnzymes) according to the manufacturers specifications and using specific primers [SEQ ID No 80 & 81].

The decarboxylase gene from Lactococcus lactis [SEQ ID No. 39] coding for Lactococcus lactis branched chain alpha-keto acid decarboxylase KdcA [SEQ ID No. 40] was amplified from pBAD-KdcA by PCR using Phusion DNA polymerase (Finnzymes) according to the manufacturers specifications and using specific primers [SEQ ID No 82 & 83].

The resulting PCR products were cloned into vector pAKP-44 using AscI and BamHI restriction enzymes resulting in vectors pAKP-81 and pAKP-82 respectively, which now contain the decarboxylase gene under the S. cerevisiae gal2 promoter and the S. cerevisiae pma1 terminator.

Plasmids pAKP-79 and pAKP-80 were restriction enzyme digested with SacI and XbaI and plasmids pAKP-81 and pAKP-82 were restriction enzyme digested with SalI and XbaI. A SacI/XbaI aminotransferase fragment was combined with a SalI/XbaI decarboxylase fragment into the S. cerevisiae low copy episomal vector pRS414, which was restriction enzyme digested with SalI and SacI.

The resulting plasmids were obtained:
pAKP-85: Pgal10-Pae_AT-Tadh2 Pgal2-Pdc_DC-Tpma1
pAKP-86: Pgal10-Pae_AT-Tadh2 Pgal2-KdcA_DC-Tpma1
pAKP-87: Pgal10-Vfl_AT-Tadh2 Pgal2-Pdc_DC-Tpma1
pAKP-88: Pgal10-Vfl_AT-Tadh2 Pgal2-KdcA_DC-Tpma1

Transformation and Growth of S. cerevisiae

S. cerevisiae strain CEN.PK113-3C was transformed with 1 μg of plasmid DNA according to the method as described by Gietz and Woods (Gietz, R. D. and Woods, R. A. (2002). Transformation of yeast by the Liac/SS carrier DNA/PEG method. Methods in Enzymology 350: 87-96). Cells were plated on agar plates with 1× Yeast Nitrogen Base without amino acids and 2% glucose.

The resulting strains were grown aerobically at 30° C. for 48 hour in Verduyn minimal medium containing 0.05% glucose and 4% galactose.

Preparation of Cell Free Extract 1 ml of potassium phosphate buffer (pH 7) was added to 0.5 g of the cell pellet. This mixture was added to a 2 ml eppendorf tube which contained 0.5 g of glassbeads with a diameter of 0.4-0.5 mM. Samples were vigorously shaken with an eppendorf shaker (IKA VIBRAX-VXR) for 20 s. The resulting cell free extract was centrifuged for 5 minutes at 14000 rpm and 4° C. The supernatant was used for enzyme activity assays.

Enzymatic Reactions for Conversion of AKP to 6-ACA in Presence of Decarboxylase and Aminotransferase Co-Expressed in S. cerevisiae A reaction mixture was prepared comprising 50 mM AKP, 5 mM magnesium chloride, 100 μM pyridoxal 5'-phosphate, 1 mM thiamine diphosphate and 50 mM racemic α-methylbenzylamine in 100 mM potassium phosphate buffer, pH 6.5. 1.6 ml of the reaction mixture were dispensed into a reaction vessel. To start the reaction, 0.4 ml of the cell free extract from S. cerevisiae containing decarboxylase and aminotransferase were added, to each of the reaction vessels. Reaction mixtures were incubated with a magnetic stirrer at 37° C. Furthermore, a chemical blank mixture (without cell free extract) and a biological blank (S. cerevisiae) were incubated under the same conditions. Samples, taken after 19 hours of incubation, were analysed by HPLC-MS. The results are summarised in the following table.

TABLE 8

6-ACA formation from AKP using a micro-organism as a biocatalyst

| Biocatalyst | 6-ACA concentration [mg/kg] |
|---|---|
| S. cerevisiae pAKP-85 | 63 |
| S. cerevisiae pAKP-86 | 226 |
| S. cerevisiae pAKP-87 | 1072 |
| S. cerevisiae pAKP-88 | 4783 |
| S. cerevisiae (biological blank) | 3.9 |
| None (chemical blank) | 1.3 |

Enzymatic Reactions for Conversion of Alpha-Ketopimelic Acid to Alpha-Aminopimelic Acid A reaction mixture was prepared comprising 10 mM alpha-ketopimelic acid, 20 mM L-alanine, and 50 μM pyridoxal 5'-phosphate in 50 mM potassium phosphate buffer, pH 7.0. 800 μl of the reaction mixture were dispensed into each well of the well plates. To start the reaction, 200 μl of the cell lysates were added, to each of the wells. Reaction mixtures were incubated on a shaker at 37° C. for 24 h. Furthermore, a chemical blank mixture (without cell free extract) and a biological blank (E. coli TOP10 with pBAD/Myc-His C) were incubated under the same conditions. Samples were analysed by HPLC-MS. The results are summarised in the following table.

TABLE 9

AAP formation from AKP in the presence of aminotransferases

| Biocatalyst | AAP concentration [mg/kg] (after 24 hrs) |
|---|---|
| E. coli TOP10/pBAD-Vfl_AT | 3.7 |
| E. coli TOP10/pBAD-Psy_AT | 15.8 |
| E. coli TOP10/pBAD-Bsu_gi16078032_AT | 11.2 |
| E. coli TOP10/pBAD-Rsp_AT | 9.8 |
| E. coli TOP10/pBAD-Bsu_gi16080075_AT | 4.6 |

TABLE 9-continued

AAP formation from AKP in the presence of aminotransferases

| Biocatalyst | AAP concentration [mg/kg] (after 24 hrs) |
|---|---|
| E. coli TOP10/pBAD-Lpn_AT | 5.4 |
| E. coli TOP10/pBAD-Neu_AT | 7.7 |
| E. coli TOP10/pBAD-Ngo_AT | 5.1 |
| E. coli TOP10/pBAD-Pae_gi9951299_AT | 5.6 |
| E. coli TOP10/pBAD-Rpa_AT | 5.4 |
| E. coli TOP10 with pBAD/Myc-His C (biological blank) | 1.4 |
| None (chemical blank) | 0 |

It is shown that the formation of AAP from AKP is catalysed by the biocatalyst.

Chemical Conversion of AAP to Caprolactam

To a suspension of 1.5 grams of D,L-2-aminopimelic acid in 21 ml cyclohexanone, 0.5 ml of cyclohexenone was added. The mixture was heated on an oil bath for 20 h at reflux (approximately 160° C.). After cooling to room temperature the reaction mixture was decanted and the clear solution was evaporated under reduced pressure. The remaining 2 grams of brownish oil were analyzed by $^1$H-NMR and HPLC and contained 0.8 wt % caprolactam and 6 wt % of cyclic oligomers of caprolactam.

The invention claimed is:

1. A recombinant host cell comprising a nucleic acid sequence containing the nucleic acid sequence of SEQ ID NO:3.

2. A recombinant host cell according to claim 1, wherein the host cell is selected from the group of *Aspergillus, Penicillium, Saccharomyces, Kluyveromyces, Pichia, Candida, Hansenula, Bacillus, Corynebacterium*, and *Escherichia*.

3. Polynucleotide comprising SEQ ID NO:3.

* * * * *